US008975294B2

(12) United States Patent
Chevion et al.

(10) Patent No.: US 8,975,294 B2
(45) Date of Patent: Mar. 10, 2015

(54) DESFERRIOXAMINE-METAL COMPLEXES FOR THE TREATMENT OF IMMUNE-RELATED DISORDERS

(75) Inventors: Mordechai Chevion, Mevasseret Zion (IL); Vladimir Vinokur, BeerSheeva (IL); Eduard Berenshtein, Jerusalem (IL); Ron Eliashar, Har-Adar (IL); Baruch Bulvik, Elazar (IL)

(73) Assignees: Hadasit Medical Research Services and Development Ltd., Jerusalem (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 122 days.

(21) Appl. No.: 13/390,838

(22) PCT Filed: Aug. 19, 2010

(86) PCT No.: PCT/IL2010/000681
§ 371 (c)(1),
(2), (4) Date: Feb. 16, 2012

(87) PCT Pub. No.: WO2011/021203
PCT Pub. Date: Feb. 24, 2011

(65) Prior Publication Data
US 2012/0220651 A1      Aug. 30, 2012

Related U.S. Application Data

(60) Provisional application No. 61/347,617, filed on May 24, 2010, provisional application No. 61/298,596, filed on Jan. 27, 2010, provisional application No. 61/235,062, filed on Aug. 19, 2009.

(51) Int. Cl.
*A61K 31/28*     (2006.01)
*A61K 31/315*    (2006.01)

(52) U.S. Cl.
CPC ............... *A61K 31/28* (2013.01); *A61K 31/315* (2013.01)
USPC .......................................... 514/492; 514/494

(58) Field of Classification Search
CPC ............................ A61K 31/28; A61K 31/315
USPC .................................................. 514/492, 494
See application file for complete search history.

(56) References Cited

U.S. PATENT DOCUMENTS

| | | | |
|---|---|---|---|
| 5,227,405 A | 7/1993 | Fridovich et al. | |
| 6,269,818 B1 * | 8/2001 | Lui et al. | 128/898 |
| 2008/0085866 A1 | 4/2008 | Greenberg et al. | |

FOREIGN PATENT DOCUMENTS

| | | |
|---|---|---|
| EP | 0 284 645 | 10/1988 |
| EP | 0 409 452 | 1/1991 |
| WO | 94/26263 | 11/1994 |
| WO | 95/00140 | 1/1995 |
| WO | 02/102345 | 12/2002 |
| WO | 2004/060490 | 7/2004 |
| WO | 2005/000224 | 1/2005 |

OTHER PUBLICATIONS

Banin, et al., Gallium-Desferrioxamine Protects the Cat Retina Against Injury After Ischemia and Reperusion, Free Radical Biology and Medicine, 2000, pp. 315-323, vol. 28, No. 3.
Banin et al., The potential of desferrioxamine-gallium as an anti-Pseudomonas therapeutc agent, PNAS, Oct. 28, 2008, pp. 16761-16766, vol. 105, No. 43.
Bar-On, et al., Hyperlipoproteinemia in Streptozotocin-treated Rats, Diabetes, Jun. 1976, pp. 509-515, vol. 25.
Chevion, A Site-Specific Mechanism for Free Radical Induced Biological Damage: The Essential Role of Redox-Active Transition Metals, Free Radical Biology & Medicine, 1988, pp. 27-37, vol. 5.
Chevion, Protection Against Free Radical-Induced and Transition Metal-Mediaed Damage: The Use of "Pul" and "Push" Mechanisms, Free Rad. Res. Comms., 1991, pp. 691-696, vols.12-13.
Chevion, et al., Copper and iron are mobilized following myocardial ischemia: Possible predictive criteria for tissue injury, Proc. Natl. Acad. Sci. USA, Feb. 1993, pp. 1102-1106, vol. 90.
Chevion, et al., The Role of Transition Metal Ions in Free Radical-Mediated Damage, Reactive Oxygen Species in Biological Systems, 1999, pp. 103-131, Colton, G.A. (ed.) Plenum Press, New York.
Kennedy, et al., Objective and Subjective Outcomes in Surgery for Chronic Sinusitis, Laryngoscope, Mar. 2000, pp. 29-31, vol. 110.
Kostopanagiotou, et al., Desferrioxamine attenuates minor lung injury following surgical acute liver failure, Eur. Respir. J., 2009, pp. 1429-1436, vol. 33.
Kung, et al., Characterization of a Murine Model of Allergic Pulmonary Inflammation, Int Arch Allergy Immunol, 1994, pp. 83-90, vol. 105.
Lalonde, et al., Aerosolized deferoxamine prevents lung and systemic injury caused by smoke inhalation, Journal of Applied Physiology, 1994, pp. 2057-2064, vol. 77, No. 5.
Lund, et al., Staging in rhinosinusitus, Rhinology, 1993, pp. 183-184, vol. 31.
Matsui, et al., The Effect of Antioxidants on Ozone-induced Airway Hyperresponsiveness in Dogs, The American Review of Respiratory Disease, 1991, pp. 1287-1290, vol. 144, No. 6.
Meltzer, et al., Rhinosinusitis: Establishing definitions for clinical research and patient care, Supplement to The Journal of Allergy and Clinical Immunology, Dec. 2004, pp. S155-S212, vol. 114, No. 6.

(Continued)

*Primary Examiner* — Kevin E Weddington
(74) *Attorney, Agent, or Firm* — Browdy and Neimark, PLLC

(57) ABSTRACT

The present invention relates to methods kits and combined compositions using DFO-metal complexes, specifically, Zinc-desferrioxamine (Zn-DFO), gallium-desferrioxamine (Ga-DFO) complexes and any combinations thereof for preventing, treating, ameliorating or inhibiting an immune-related disorder, specifically, a skin-related inflammatory disorder such as psoriasis, an inflammatory respiratory condition such as asthma, and an autoimmune disease such as diabetes and any immune-related disorder.

4 Claims, 19 Drawing Sheets

(56) References Cited

OTHER PUBLICATIONS

Misawa, et al., Airway inflammation induced by xanthine/xanthine oxidase in guinea pigs, Agents Actions, 1993, pp. 19-26, vol. 38, No. 1-2.

Moskovitz, et al., Methionine sulfoxide reductase (MsrA) is a regulator of antioxidant defense and lifespan in mammals, PNAS, Nov. 6, 2001, pp. 12920-12925, vol. 98, No. 23.

Moskovitz, et al., The yeast peptide-methionine sulfoxide reductase functions as an antioxidant in vivo, Proc. Natl. Acad. Sci. USA, Sep. 1997, pp. 9585-9589, vol. 94.

Muluk, et al., Role of Vascular Endothelial Growth Factor in the Pathogenesis of Nasal Polyps, The Journal of Otolaryngology, Dec. 2007, pp. 357-366, vol. 36, No. 6.

Ophir, et al., Protection of the Transiently Ischemic Cat Retina by Zinc-Desferrioxamine, Invest Ophthalmol Vis Sci., 1994, pp. 1212-1222, vol. 35.

Reagan-Shaw, et al., Dose translation from animal to human studies revisited, The FASEB Journal, 2007, pp. 659-661, vol. 22.

Renstrom, et al., Allergic sensitization is associated with increased bronchial responsiveness: a prospective study of allergy to laboratory animals, Eur Respir J, 1995, pp. 1514-1519, vol. 8.

Siganos, et al., Topical Use of Zinc Desferrioxamine for Corneal Alkali Injury in a Rabbit Model, Cornea, 1998, pp. 191-195, vol. 17(2).

Author unknown, Psoriasis, U.S. National Institutes of Health Medical Encyclopedia, www.nlm.nih.gov/medlineplus/ency/article/000434.htm, 2013, pp. 1-4.

Wei, et al., The Streptozotocin-Diabetic Rat as a Model of the Chronic Complications of Human Diabetes, Heart, Lung and Circulation, 2003, pp. 44-50, vol. 12.

Wu, et al., Desferrioxamine modulates chemically induced T helper 2-mediated autoimmunity in the rat, Clin Exp Immunol, 2004, pp. 194-199, vol. 135.

International Search Report for PCT/IL2010/000681, mailing date Mar. 2, 1011.

* cited by examiner

DESFERRIOXAMINE-METAL COMPLEXES FOR THE TREATMENT OF IMMUNE-RELATED DISORDERS

FIELD OF THE INVENTION

The present invention concerns method and uses of DFO-metal complexes in the treatment or prevention of immune-related disorders. More specifically, the invention relates to Zinc-desferrioxamine (Zn-DFO), gallium-desferrioxamine (Ga-DFO) complexes and any combinations thereof for treating chronic or acute inflammatory-related skin pathologic conditions, respiratory diseases, and diabetes.

BACKGROUND OF THE INVENTION

All publications mentioned throughout this application are fully incorporated herein by reference, including all references cited therein.

Zinc-desferrioxamine (Zn-DFO) and gallium-desferrioxamine (Ga-DFO) are metal complexes, previously shown by the inventors to inhibit the catalysis of iron (and copper) in the formation of free radicals. Their protective activity can be visualized through the "pulling" out of available and redox active iron that is responsible for the production of the hydroxyl radicals via chelation by the DFO component. At the same time, the relatively inert zinc (or gallium) ion, that is liberated during the exchange of iron within the complex, further acts as a secondary antioxidant, by "pushing" out an additional iron ion from a binding site [Chevion, M. (1988) Free Radic Biol Med 5, 27-37; Chevion, M. (1991) Free Radic Res Commun 12-13, 691-6]. The spatial structure of these complexes is markedly different from that of DFO alone, allowing for enhanced infiltration into cells and tissues [Chevion et al. (1991), ibid]. There has been a report that high dose DFO can inhibit lymphproliferation, IgE production and IL-4 gene expression in $HgCl_2$-induced autoimmunity in BN rats [Zu et al (2004), Clin. Exp. Immunol 135, 194-199]. In addition, DFO was reported to attenuate minor lung injury following surgical acute liver failure [Kostopanagiotou et al, (2009) Eur. Respir. J. 33:1429-1436]. In previous studies, the inventors have shown that systemic treatment with Zn-DFO and Ga-DFO reduced damage to the retina subjected to ischemia and reperfusion, in accord with their enhanced infiltration through the blood-retinal barrier [Ophir, A. et al. (1994) Invest. Ophthalmol. Vis. Sci. 35, 1212-22; Banin, E. et al. (2000) Free Radic Biol. Med. 28, 315-23]. Likewise, topical application of Zn-DFO reduced corneal damage following alkali burn [Siganos, C. et al. (1998) Cornea 17, 191-5]. A previous publication of the inventors, WO 2004/060490, concerns the use of topical application of Zn-DFO and Ga-DFO in reducing ocular damage following exposure to nitrogen and other mustard gases, as well as other warfare agent, e.g. Sarin, which inflict injury through different mechanism. In the present invention, the inventors surprisingly demonstrate the beneficial effects imparted by Zn-DFO and Ga-DFO in the treatment of different immune-related disorders including asthma, diabetes mellitus type II and I, and psoriasis.

Asthma

Asthma is a chronic inflammation of the lungs in which the airways (bronchi) are reversibly narrowed. Asthma affects 7% of the population, and 300 million worldwide. During attacks (exacerbations), the smooth muscle cells in the bronchi constrict, the airways become inflamed and swollen, leading to breathing difficulties. The frequency of acute asthmatic attacks depends on asthma severity. Acute asthma exacerbations cause 4,000 deaths a year in the U.S. Attacks can be prevented by avoiding triggering factors and by drug treatment. Drugs are used for acute attacks, commonly inhaled beta-2 agonists. In more serious cases, drugs are used for long-term prevention, starting with inhaled corticosteroids, and then long-acting β2-agonists if necessary. Leukotriene antagonists are less effective than corticosteroids but have no side effects. Monoclonal antibodies such as mepolizumab and omalizumab are sometimes effective According to several reports, asthma attacks are associated with a significant increase in production of reactive oxygen-derived species (ROS) and aggravation of inflammatory condition. Currently, asthma treatment is based on long-term control medications as corticosteroids or leukotrienes modifiers that often cause serious side effects with a considerable price.

The present invention now demonstrates that treatment with the metal complexes of the invention and combinations thereof, reduces the buildup of ferritin-bound labile iron in asthma-related inflamed tissues accumulation of tissue ferritin and the total amount of ferritin-bound iron. The invention further demonstrates reduction of eosinophils and lymphocytes numbers in the peribronchial and alveolar regions, attenuation of the damage to the airway epithelium and mucus overproduction, reduction in neutrophils in bronchoalveolar fluid, reduction of mucous content score, reduction of peribronchial infiltrate value, reduction of epithelial cells metaplasia, reduction of fibrous connective tissue, down-regulation of lungs-ferritin content and its saturation with iron Diabetes Mellitus Diabetes is a disease characterized by failure of insulin feedback and secretion in the beta cells of the pancreatic islets of Langerhans and is one of the most common endocrine diseases across all age groups and populations. The most obvious metabolic effect in diabetes is chronic, erratic elevation of the blood glucose level which is associated with progressive damage to blood vessels. This may lead to heart attack, stroke, blindness, peripheral nerve dysfunction, and kidney failure.

Presently there are 18.2 million people in the United States alone, and 171 millions worldwide who have diabetes. In addition to the clinical morbidity and mortality, the economic cost of diabetes is huge, exceeding US$90 billion per year in the United States alone, and the prevalence of diabetes is expected to increase more than two-fold by the year 2030.

There are two major forms of diabetes mellitus: insulin-dependent (Type I) diabetes mellitus which accounts for 5 to 10% of all cases, and non-insulin dependent (Type-II) diabetes mellitus which comprises roughly 90 to 95% of cases. Type I diabetes mellitus is an autoimmune disease characterized by progressive destruction of pancreatic beta-cells and most often occurring in children and young adults. The disease is associated with high rate of severe irreversible complications occurring despite the availability of insulin replacement, usually through injections administered 1-4 times daily.

Most therapeutic strategies for treatment or prevention of type I diabetes mellitus are directed to suppression of the autoimmune response in order to prevent beta-cell destruction. Accordingly, various immunosuppressive agents have been considered for preventing the destruction of pancreatic beta-cells and have been attempted, such as glucocorticoids, cyclophosphamide, cyclosporin A, rapamycin, FKS06 and prodigiosin. However, the use of such immunosuppressive agents may cause severe side effects such as drug-related toxicity to liver or kidney and to increased incidence of infectious complications, particularly in patients with diabetes mellitus that are already susceptible to infections as part of their disease.

Type II-diabetes results from a compromised insulin production combined with insulin resistance which reflects the inability to properly use insulin. Type II is oftentimes associated with aging. These diabetes, patients typically begin therapy by following a regimen of an optimal diet, weight reduction and exercise. Drug therapy is initiated when these measures no longer provide adequate metabolic control. Initial drug therapy includes sulfonylureas (for example, tolbutamide, chlorpropamide and glibenclamide), biguanides (for example, metformin and buformin), peroxisome proliferator-activated receptors (PPAR) activators (for example, pioglitazone and rosglitazone) and alpha-glucosidase inhibitors (for example, acarbose and voglibose). However, over 50% of all diabetics treated by presently available drugs demonstrate poor glycemic control and, within six years, require insulin replacement therapy as the last resort.

Although many of the symptoms of diabetes mellitus may be controlled by insulin therapy, the long-term-complications of both type I and type II diabetes mellitus are severe and may reduce life expectancy by as much as one third. Over time, elevated blood glucose levels damage blood vessels, the heart, eyes, kidneys, the nervous system, skin, connective tissue, and white blood cell function.

Moreover, insulin therapy may result in insulin allergy, insulin resistance, atrophy of the subcutaneous fat at the site of insulin injection (i.e., lipoatrophy), enlargement of subcutaneous fat deposit (i.e., lipohypertrophy) due to lipogenic action of high local concentration of insulin, and insulin edema.

The present invention surprisingly shows that treatment with the metal complexes of the invention prevents the development of key diabetes type II pathologies, including hyperglycemia, increased protein oxidation and degradation, decreased protein activity, and cataract formation. Moreover, although the metal complexes of the invention cannot restore destroyed pancreatic beta cells lost due to diabetes type I, the complexes appear to ameliorate physiological manifestations of the disease.

Psoriasis

According to the US National Institutes of Health Medical Encyclopedia, website http://www.nlm.nih.gov/medlineplus/ency/article/000434.htm, psoriasis affects about 2.7% of the people of the world. In the United States, about 3 million people show symptoms of psoriasis at any given time. Psoriasis may affect any or all parts of the skin, but it is more commonly seen on the skin of the trunk, elbows, knees and/or scalp, on skin folds, or in the fingernails and/or toenails. Psoriasis may be aggravated by injury or irritation, such as cuts, burns, rashes or insect bites. It is particularly severe in immuno-suppressed people, like those with AIDS or undergoing chemotherapy for cancer, and in people who have other autoimmune disorders, such as rheumatoid arthritis. In psoriatic arthritis, both a joint and the skin are affected.

When the skin is healthy, it takes about a month for new skin cells to move up from the lower layers to the surface of the skin. In psoriasis, this process takes only a few days, and it results in the build-up of dead skin cells and formation of thick scales.

Keratinocyte proliferation is characteristic of psoriasis. Symptoms of psoriasis include patches of skin that can (a) be dry and/or red; and/or (b) be covered with silvery scales; and/or (c) be raised; and/or (d) have red borders; and/or (e) crack and/or become painful; and/or (f) be discrete and/or demarcated. Additional symptoms may include, for example, (a) skin lesions, such as pustules; and/or (b) cracking of skin; and/or (c) skin redness and/or inflammation; and/or (d) itching; and/or (e) small scaling dots on the skin, especially in children; and/or (f) joint pain or aching, which may be associated with psoriatic arthritis. Further abnormalities in psoriasis may include, for example, nail abnormalities; genital lesions in males; and burning, itching, discharge or increased tearing of the eye.

Psoriasis is considered to be an immune disease. It is classified in many recent publications as an autoimmune disease, a class of diseases in which the immune system targets the body's own cells. Publications suggest that psoriasis is a type I autoimmune disease, mediated, for example, by interferon (IFN) gamma and/or other inflammatory cytokines, and/or by T-lymphocytes. For example, IFN-gamma-producing CD4+ Th1-lymphocytes are considered to be of importance in the pathogenesis of psoriasis, as they influence differentiation and functioning of antigen presenting cells, mast cells, neutrophils and endothelial cells. The inflammatory cascade provokes neo- angiogenesis in the dermis and proliferation of keratinocytes. It has been recently reported that CD11c+cells with markers of dendritic cells are a major cell type in the skin lesions of psoriasis. These CD11c+cells, which are evident in both epidermis and dermis, are sites for expression of two mediators of inflammation in diseased skin, inducible nitric oxide synthase (iNOS) and TNF-alpha These cells also express HLA-DR, CD40, and CD86 and the dendritic cell maturation markers DCLAMP and CD83.

Mild psoriasis is currently treated with non-steroidal anti-inflammatory drugs (NSAIDs), exemplified by topically applied salicylic acid and its orally taken derivative, aspirin (known to inhibit NF-.kappa.B); topically applied coal tar; orally taken vitamin D derivatives, like calcipotriol; UV-B phototherapy; and topically applied glucocorticosteroids, like betametasone, known to down-regulate CCL27. Combinations of these are often used. Traditional treatments of severe psoriasis include systemic, orally taken, disease-modifying anti-rheumatic immunosuppressive drugs (DMARDs), like methotrexate, cyclosporin, psoralen plus UVA (PUVA), oral retinoids and fumaric acid esters, gold salts and leflunomide. More recently, biological drugs were introduced to treat severe psoriasis. These include (a) T-cell count lowering AMEMIVE® (alefacept), a recombinant protein binding to CD2 on memory-effector T lymphocytes, inhibiting their activation and reducing the number of these cells. It is a fusion protein composed of leukocyte function-associated antigen type 3 (LFA-3) protein and human IgG1 Fc domains, systemically administered by intramuscular injection. (b) RAPTIVA® (efalizumab), which is a humanized monoclonal antibody against the CD11a subunit of leukocyte function-associated antigen-1 (LFA-1). CD11a is a T-cell surface molecule, important in T-cell activation, T-cell migration into skin, and cytotoxic T-cell function. RAPTIVA® (efalizumab) binds to the CD11a on T-cells and reversibly blocks the interaction between LFA-1 and its adhesion partner molecule ICAM-1. Weekly systemic injections of RAPTIVA® (efalizumab) must continue indefinitely to maintain improvement. (c) ENBREL® (etanercept), a human TNF-alpha receptor, made by fusing two natural TNF-receptors. Its affinity for TNF-alpha is greater than that of the natural monomeric TNF-alpha receptor of the immune system. ENBREL® (etanercept) is systemically administered, and deactivates TNF-alpha upon binding. (d) HUMIRA® (adalimumab), a human IgG1 monoclonal TNF-alpha-binding and inactivating antibody, is used for treating psoriatic arthritis. Unlike the other TNF-alpha inhibitors, it is locally injected. (e) REMICADE® (infliximab), a chimeric (mouse-human) IgG1 monoclonal antibody, which binds to and inactivates TNF-.alpha., and administered by systemic injection.

There is a need for a safe, less expensive, topically applied drug for psoriasis management. The biological drugs ameliorate the symptoms of, but do not cure, psoriasis. All five biological drugs listed above are injected, and the injections must continue indefinitely. Topically applied compositions are needed, as these could be safer than the injected or otherwise systemically, e.g. orally, administered drugs, injected and otherwise systemically administered drugs being more likely to affect also organs other than the targeted psoriatic skin. There is also a need to reduce the heavy financial burden associated with treating psoriasis. The annual cost of treating psoriasis with any of the five biological drugs in the USA is between about $15,000 and about $20,000 to $30,000, an amount representing about half of the annual income of many U.S. wage earners. The price of cyclosporine is also high, the drug costing annually about $10,000.

Although the non-biological drug cyclosporin and the biological drugs are generally safe at their dermatological dosage, side effects have been reported. Cyclosporin increases the risk of squamous cell carcinoma of the skin. Adalimumab increases the incidence of serious infections by two-fold, its most notable complication being reactivation of tuberculosis, and also depression syndrome. Among the infliximab treated patients a small percentage reported pneumonia, tuberculosis, lymphoma, drug-induced lupus and hepatotoxicity. Anti-efalizumab antibodies developed in approximately 5% of the subjects who were treated with efalizumab. Immune-mediated thrombocytopenia platelet counts at or below 52,000 cells/microliter have been observed in 0.3% of the efalizumab treated patients and four patients developed hemolytic anemia. The overall incidence of hospitalization for infections was 1.6 per 100 patient-years for efalizumab-treated patients compared with 1.2 per 100 patient-years for placebo-treated patients.

The present invention demonstrates that treatment with the metal complexes of the invention is not dermatoxic and significantly reduces psoriasis symptoms, as well as other skin inflammation disorders.

Thus, it is one object of the invention to provide methods using different desferrioxamine-metal complexes, specifically, at least one of Zn-DFO and Ga-DFO for preventing and treating an immune-related disorder, for example, chronic or acute inflammatory-related skin pathologic conditions, respiratory disease, and diabetes.

Another object of the invention concerns combined compositions comprising Zn-DFO and Ga-DFO complexes for treating immune related disorders.

In another object, the invention provides kits combining DFO and metals, specifically, at least one of Zn and Ga, for treating chronic or acute inflammatory-related skin pathologic conditions, respiratory disease, and diabetes.

These and other objects of the invention will become apparent as the description proceeds.

SUMMARY OF THE INVENTION

In the first aspect, the invention relates to a method of preventing, treating, ameliorating or inhibiting an immune-related disorder, specifically, an inflammatory disorder, particularly psoriasis, asthma, diabetes and any immune-related disorder. The method of the invention comprises the step of administering to a subject in need thereof a therapeutically effective amount of at least one desferrioxamine-metal complex (DFO-metal complex), or any combination thereof or any pharmaceutical composition comprising the same.

In a second aspect, the invention contemplates the use of a therapeutically effective amount of at least one desferrioxamine-metal complex (DFO-metal complex), or any combination thereof in the preparation of a composition for the prophylaxis, treatment, amelioration or inhibition of an immune related disorder, specifically, psoriasis, asthma, diabetes and any immune-related disorder.

In a third aspect, the invention is directed to a composition comprising a combination of a therapeutically effective amount of at least two desferrioxamine-metal complexes (DFO-metal complexes), the composition optionally further comprises at least one pharmaceutically acceptable carrier, diluent, excipient and/or additive. Specific embodiments of the invention relate to combined compositions comprising a combination of Zn-DFO complex with Ga-DFO complex.

In another aspect, the invention provides a kit for achieving a therapeutic effect in a subject in need thereof, specifically, a subject suffering of an immune related disorder, for example, psoriasis, asthma, diabetes and any immune-related disorder. The kit of the invention comprises at least one of:

(I) compounds for Zn-DFO complex formation comprising:
  (i) Zinc ions (Zn(II)) in any form of salts, amides or esters thereof, or a pharmaceutically acceptable derivative thereof and a pharmaceutically acceptable carrier or diluent, optionally, in a first unit dosage form;
  (ii) DFO, or a pharmaceutically acceptable derivative thereof and a pharmaceutically acceptable carrier or diluent, optionally, in a second unit dosage form; and
  (iii) optionally solutions, buffers and components which provide suitable conditions for complex formation; and/or compounds required for extension of the shelf-life of the preparations;

(II) compounds for Ga-DFO complex formation comprising:
  (i) Gallium ions (Ga(III)) in any form of salts, amides or esters thereof, or a pharmaceutically acceptable derivative thereof and a pharmaceutically acceptable carrier or diluent, optionally, in a third unit dosage form;
  (ii) DFO, or a pharmaceutically acceptable derivative thereof and a pharmaceutically acceptable carrier or diluent, optionally, in a fourth unit dosage form; and
  (iii) optionally solutions, buffers and components which provide suitable conditions for complex formation and/or for extension of the shelf-life of the preparations;

(III) compounds for Mn-DFO complex formation comprising:
  (i) Manganese ions, in any valency state, including but not limited to Mn(II), Mn(III) and Mn(IV), in any form of salts, amides or esters thereof, or a pharmaceutically acceptable derivative thereof and a pharmaceutically acceptable carrier or diluent, optionally, in a fifth unit dosage form;
  (ii) DFO, or a pharmaceutically acceptable derivative thereof and a pharmaceutically acceptable carrier or diluent, optionally, in a sixth unit dosage form; and
  (iii) optionally solutions, buffers and components which provide suitable conditions for complex formation and/or for extension of the shelf-life of the preparations;

(IV) container means for containing the unit dosage forms.

These and other aspects of the invention will become apparent by the hand of the following figures.

Figure 1A:
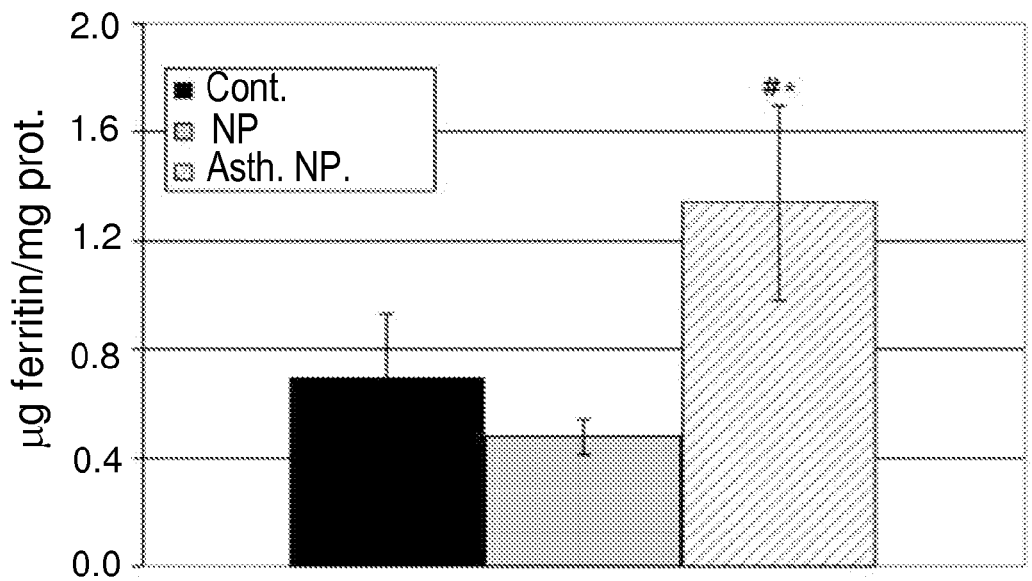
FIG. 1A-1B

Ferritin Concentration and Total Ferritin-Bound Iron in Nasal Polyps and Turbinates from Human Subjects FIG. 1A. Tissue samples of inferior turbinates from control group patients (n=11), and nasal polyps from non-asthmatic (n=15) or asthmatic (n=10) patients were collected and ferritin concentration was quantified by ELISA.

Figure 1B:
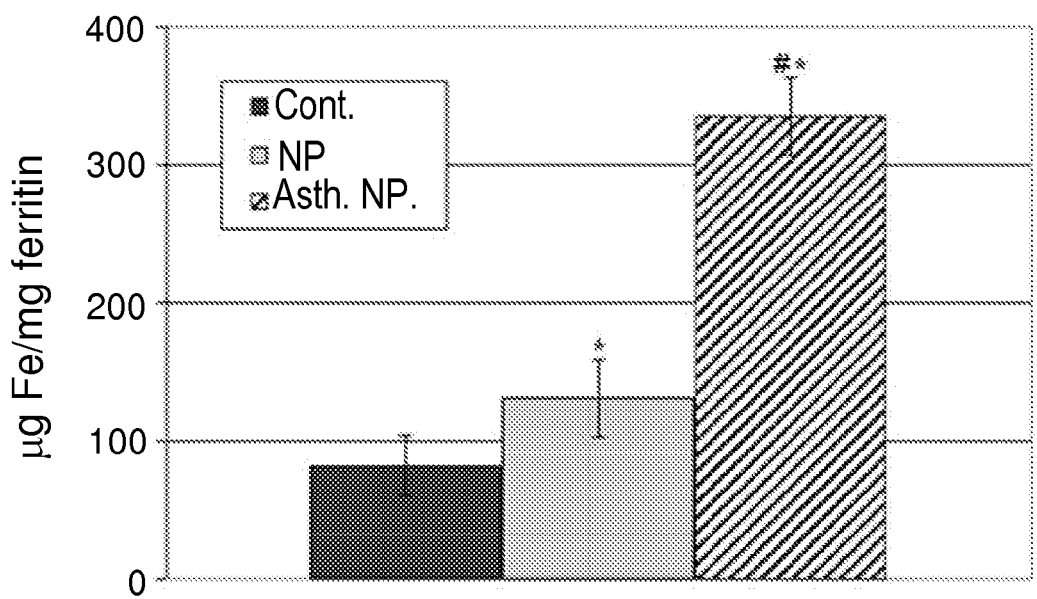

FIG. 1B. Ferritin saturation by iron was measured by spectrophotometric analysis of dissolved immunoprecipitated ferritin. Mean±S.E.M values are shown; *—denotes $p \leq 0.05$ vs. the control; #—denotes $p \leq 0.05$ between the polyps subgroups.

Abbreviations: Asth.NP. (asthma and nasal polyps); NP (nasal polyps); prot. (protein); Cont. (control).

FIG. 2

Treatment of Asthmatic Mice with a Mixture of Zn-DFO/Ga-DFO (3:1) Reduces BAL Neutrophils Infiltration Calculated density of bronchoalveolar lavages (BAL) neutrophils. Mean±S.E.M values are shown. * denotes $p<0.05$ vs. the control; # denotes $p<0.05$ vs. the asthmatic non-treated group.

Abbreviations: Asth. (asthma); Cont. (control); neut. (neutrophils).

FIG. 3A-3C

Figure 3A:
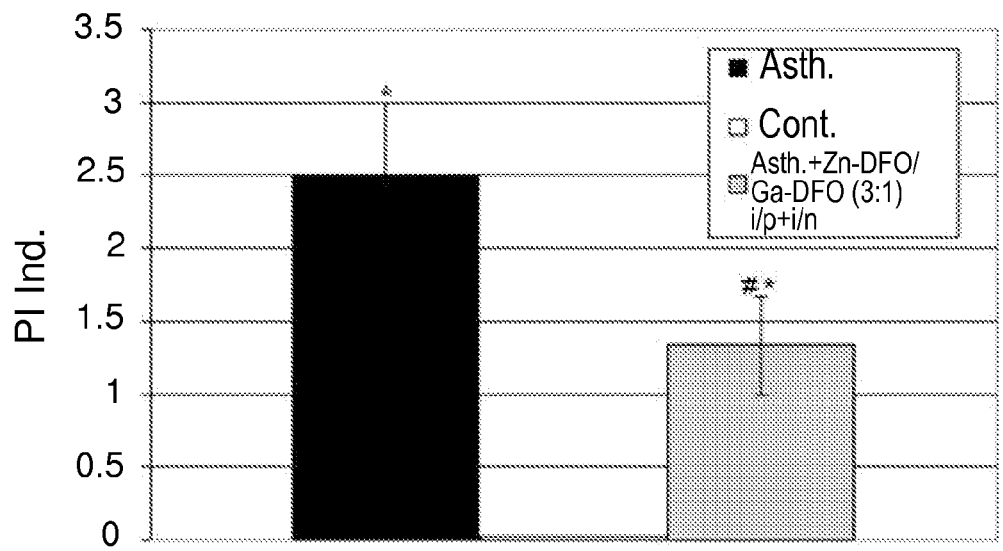

Treatment of Asthmatic Mice with a Mixture of Zn-DFO/Ga-DFO (3:1) Ameliorates Tissue Inflammation Score FIG. 3A. Average score of Peribronchial infiltrate as evaluated by haematoxylin-eosine stained histological sections.

Figure 3B:
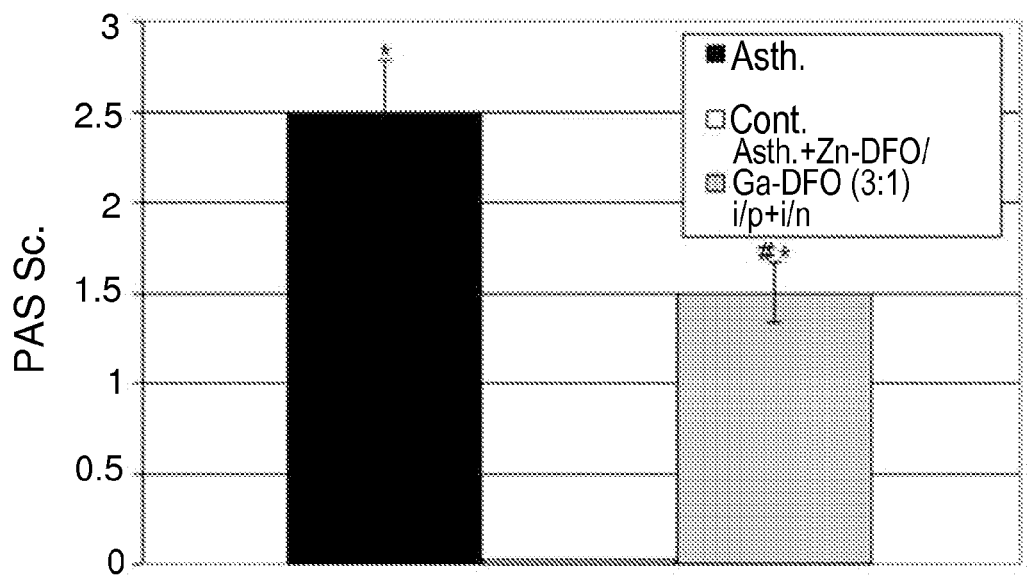

FIG. 3B. Average score of PAS staining for bronchi epithelial cells metaplasia.

Figure 3C:
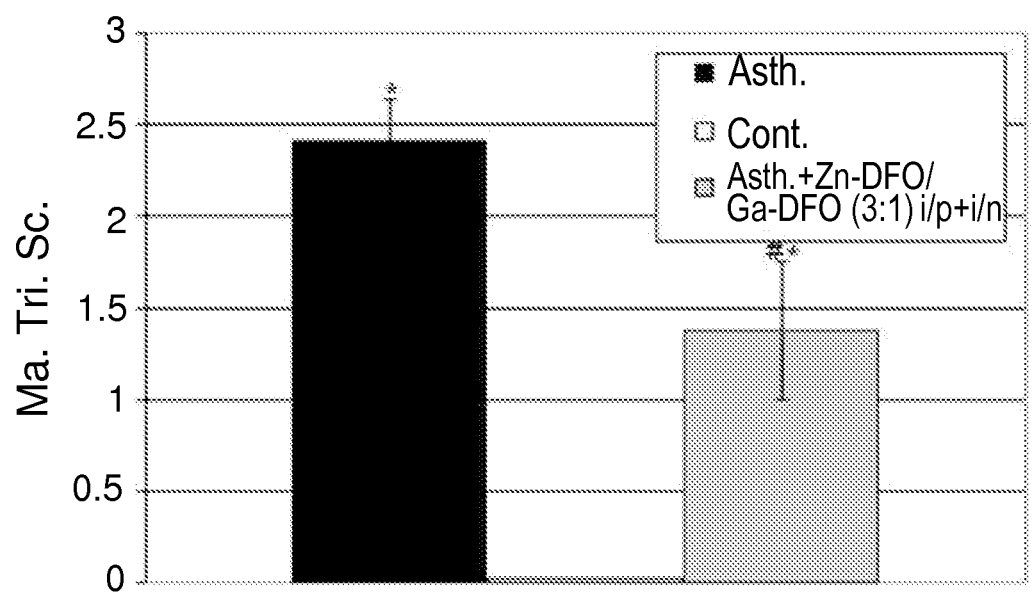

FIG. 3C. Mason's trichrome staining score for fibrous connective tissue. Mean±S.E.M values are shown. * denotes $p<0.05$ vs. the control; # denotes $p<0.05$ vs. the asthmatic non-treated group.

Abbreviations: Asth. (asthma); Cont. (control); PI. Ind. (peribronchial infiltrate index); PAS Sc. (periodic acid-Schiff score); Ma. Tr. Sc. (Mason's trichrome staining score).

FIG. 4A-4B

Figure 4A:
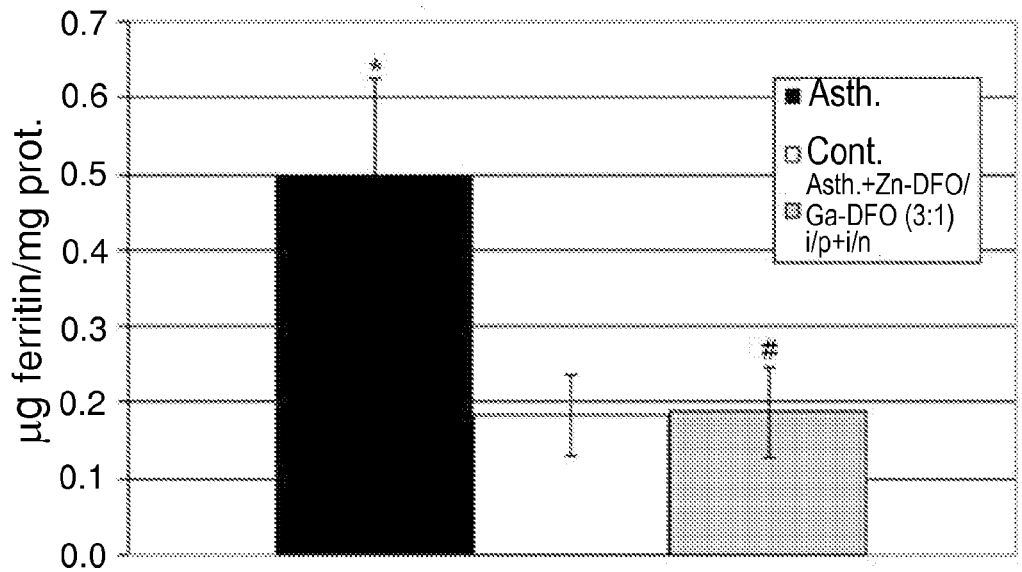

Treatment of Asthmatic Mice with a Mixture of Zn-DFO/Ga-DFO (3:1) Inhibits Ferritin Accumulation and Iron Accumulation in the Lungs FIG. 4A. Tissue ferritin concentration.

Figure 4B:
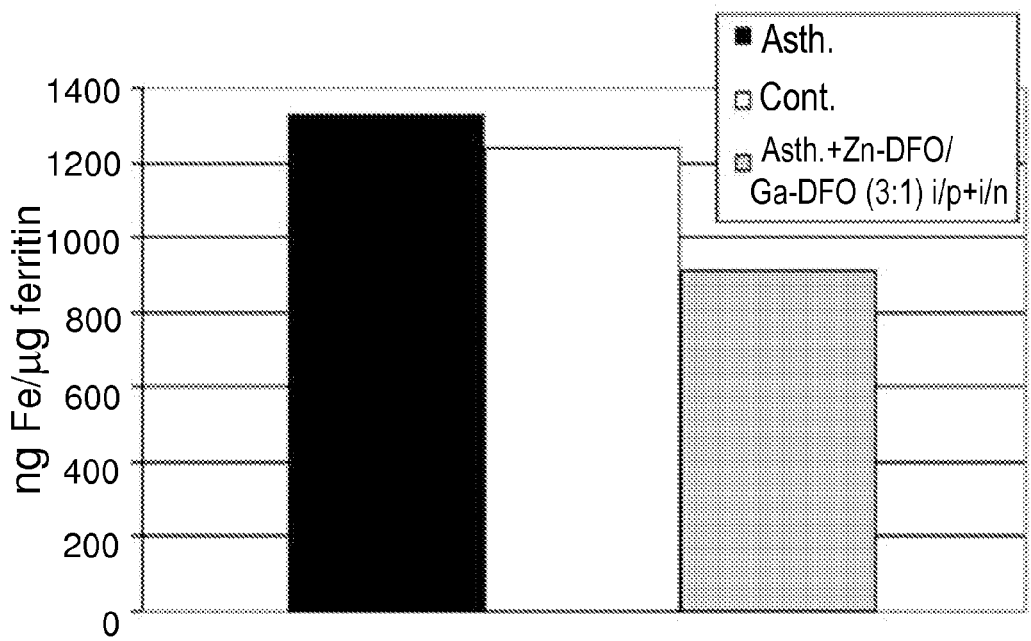

FIG. 4B. Ferritin-bound iron. Mean±S.E.M values are shown. # denotes $p<0.05$ vs. the asthmatic non-treated group.

Abbreviations: Asth. (asthma); Cont. (control); prot. (protein).

FIG. 5A-5B

Figure 5A:
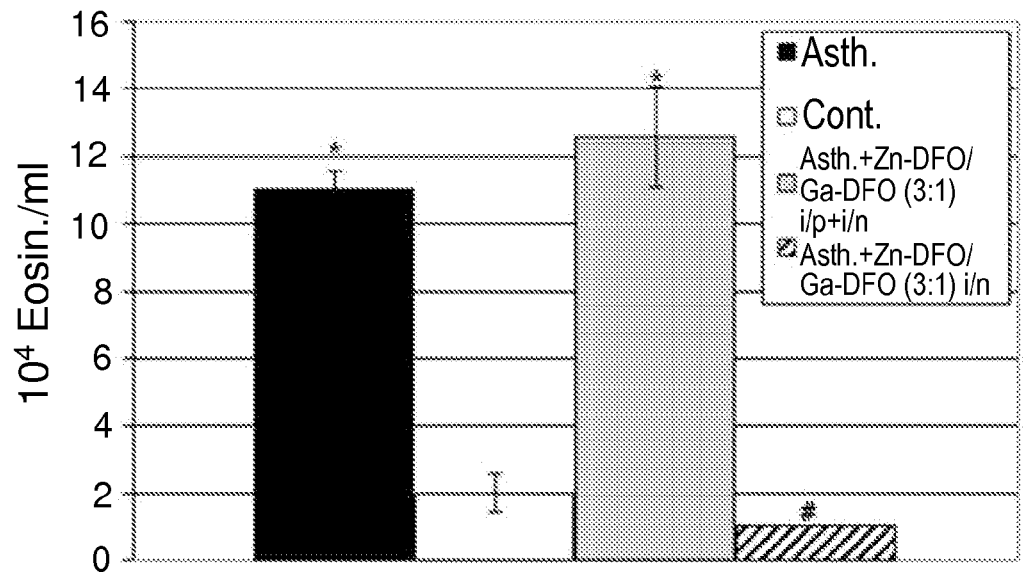

Treatment of Asthmatic Mice with a Mixture of Zn-DFO/Ga-DFO (3:1) by Intranasal Administration Reduces BAL Neutrophils and Eosinophils Infiltration in the Lungs FIG. 5A. Calculated density of BAL eosinophils.

Figure 5B:
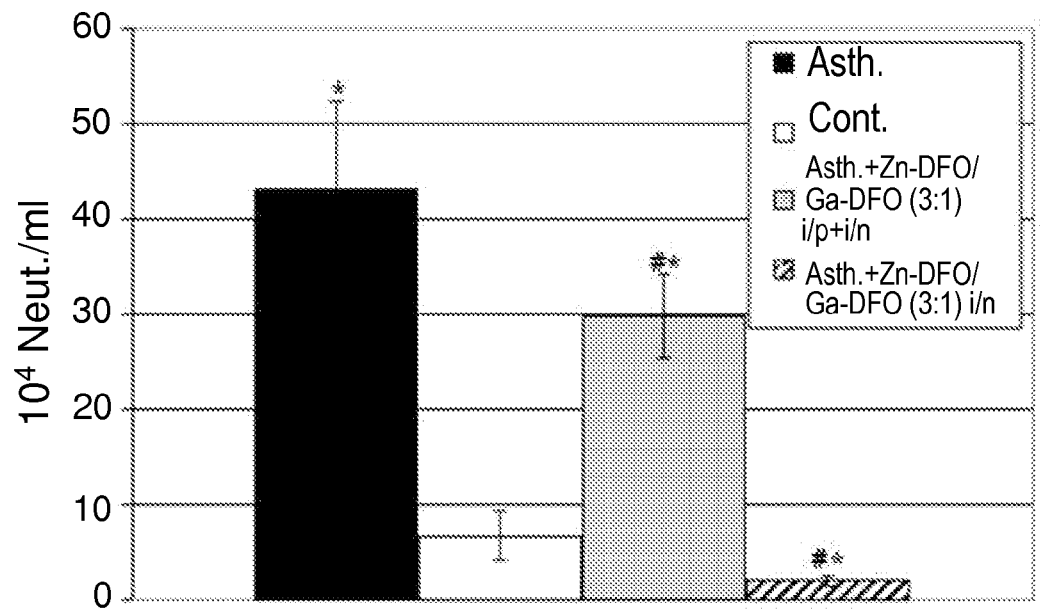

FIG. 5B. Calculated density of BAL neutrophils. Mean±SE values are shown. * denotes $p<0.05$ vs. the control; # denotes $p<0.05$ vs. the asthmatic non-treated group.

Abbreviations: Asth. (asthma); Cont. (control); Neut. (neutrophils); Eosin. (eosinophils).

FIG. 6A-6C

Figure 6A:
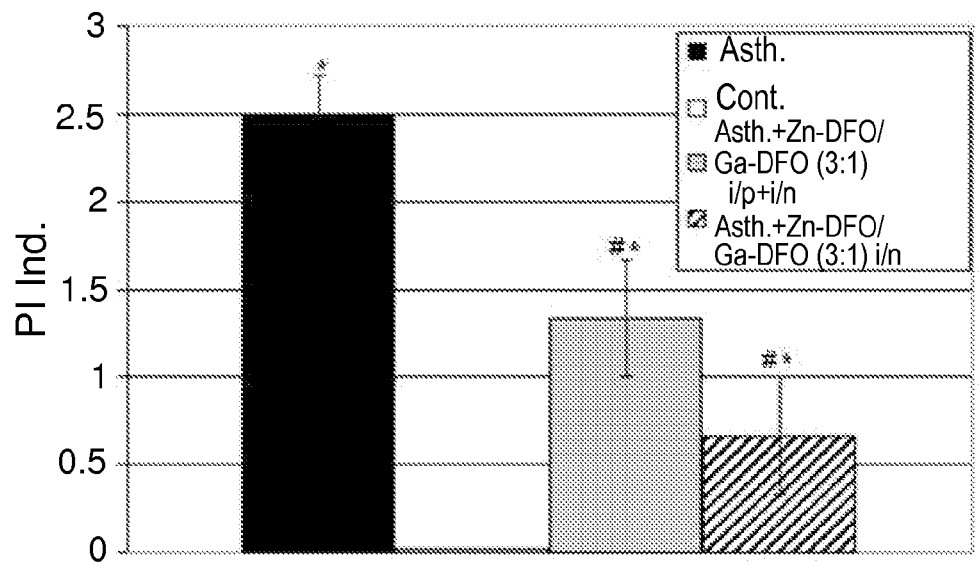

Treatment of Asthmatic Mice with a Mixture of Zn-DFO/Ga-DFO (3:1) by Intranasal Administration Ameliorates Lung Inflammation Score FIG. 6A. Peribronchial infiltrate average score.

Figure 6B:
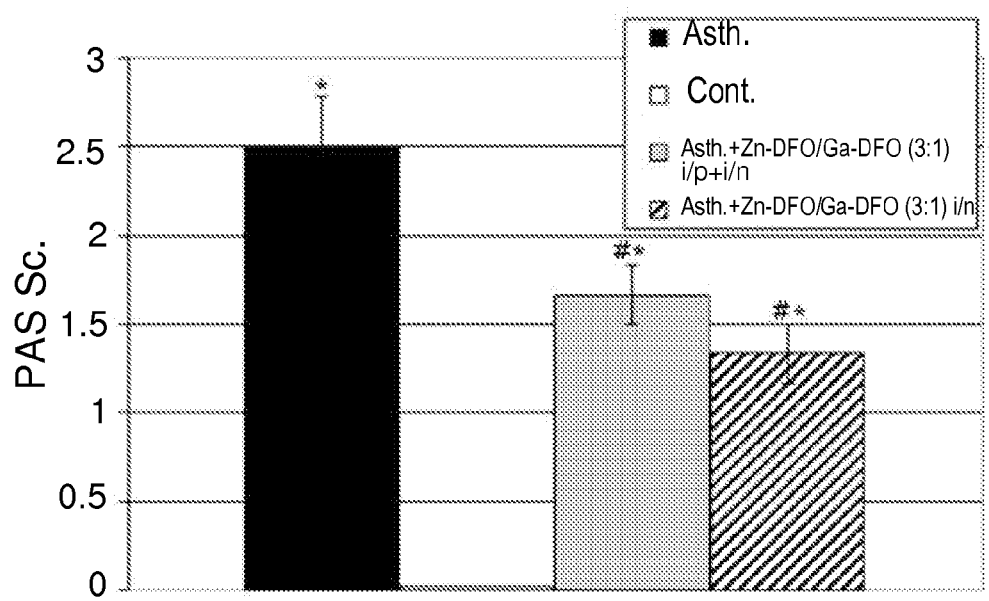

FIG. 6B. PAS staining average score for epithelial cells metaplasia.

Figure 6C:
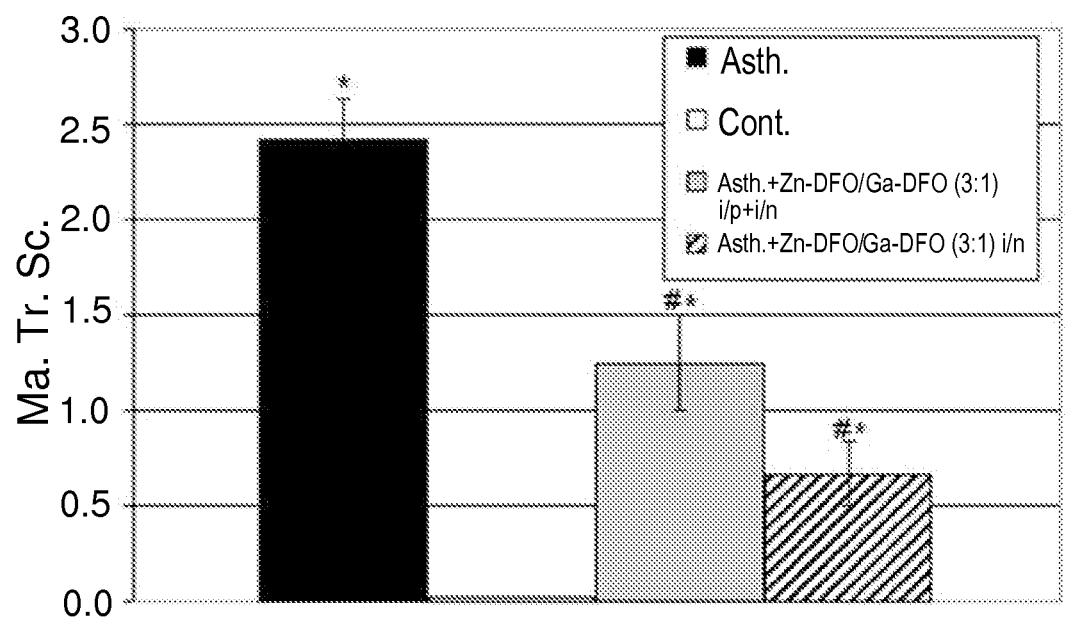

FIG. 6C. Mason's trichrome staining average score for fibrous connective tissue. Means ±SE are shown. * denotes $p<0.05$ vs. the control; # denotes $p<0.05$ vs. the asthmatic non-treated group.

Abbreviations: Asth. (asthma); Cont. (control); PI Ind. (peribronchial infiltrate index); PAS Sc. (periodic acid-Schiff score); Ma. Tr. Sc. (Mason's trichrome staining score).

FIG. 7A-7B

Figure 7A:
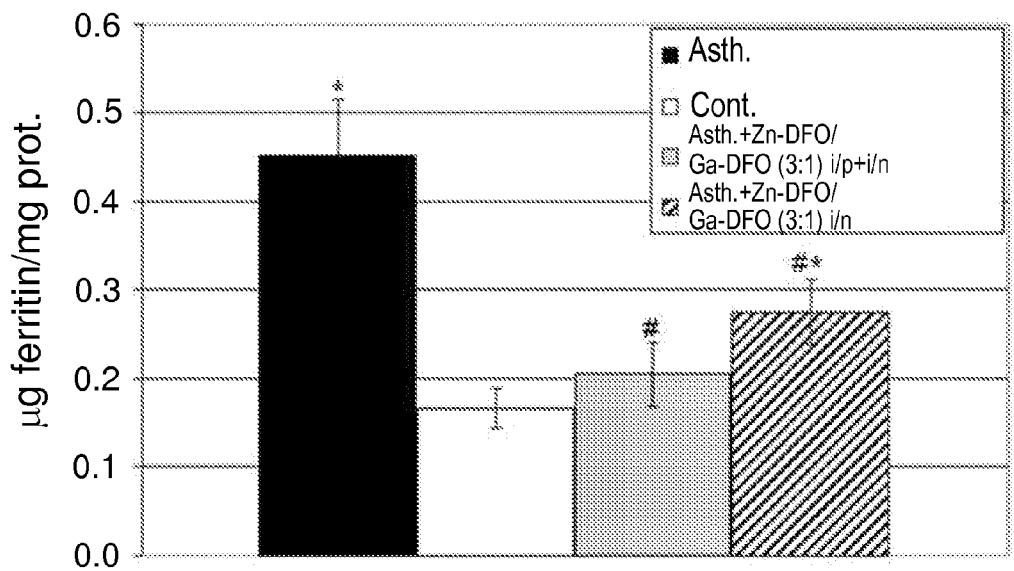

Treatment of Asthmatic Mice with a Mixture of Zn-DFO/Ga-DFO (3:1) by Intranasal Administration Inhibits Ferritin Accumulation and Iron Accumulation in the Lungs FIG. 7A. Tissue ferritin concentration.

Figure 7B:
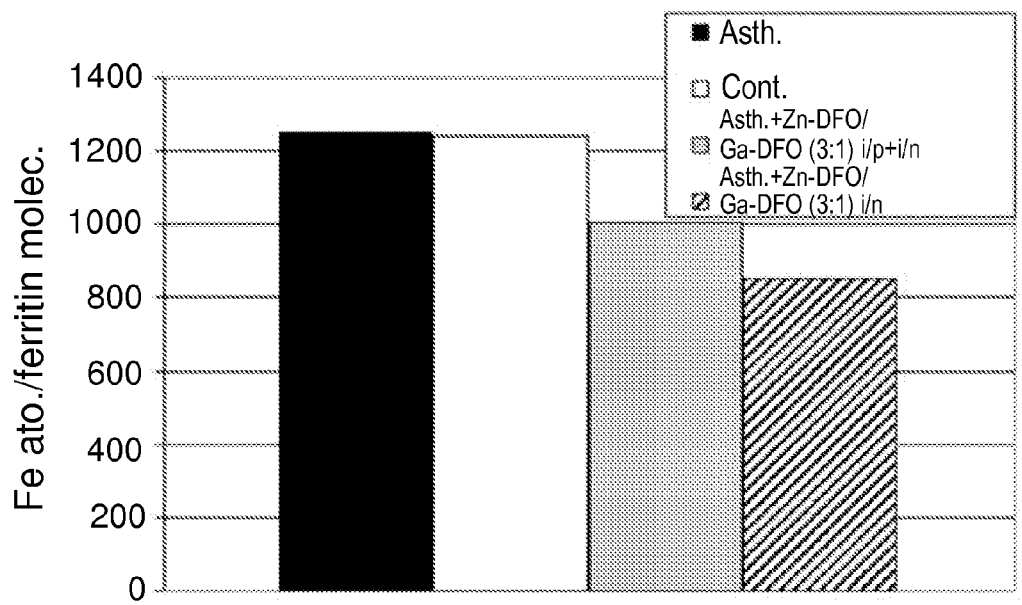

FIG. 7B. Ferritin-bound iron concentration. Mean±SE values are shown. * denotes $p<0.05$ vs. the control; # denotes $p<0.05$ vs. the asthmatic non-treated group.

Abbreviations: Asth. (asthma); Cont. (control); prot. (prot), Ato. (atoms); molec. (molecule).

FIG. 8

Treatment of Diabetic Sand Rats with Either $Zn^{2+}$, $Ga^{3+}$ or their Respective DFO Complexes Prevent an Increase in their Blood Glucose Levels Cumulative (integrated) three hours response to a 200 mg glucose dose, given orally, per 100 g body weight is shown. The result of the standard diet Group I (control; non diabetic) is considered as baseline (zero) value.

Abbreviations: Diab. (diabetes); GTT (glucose tolerance test).

FIG. 9

Treatment with Zn-DFO/Ga-DFO Mixture (3:1) Attenuates Weight Gain in High-energy Diet Fed Sand Rats Body weight of Zn-DFO/Ga-DFO treated and non-treated high-energy diet fed sand rats.

Mean±S.E.M values are shown.

Abbreviations: Bod. Wei. (body weight); D.Exp. (day of experiment); Diab. (diabetes); Cont. (control); g (grams).

FIG. 10A-10B

Figure 10A:
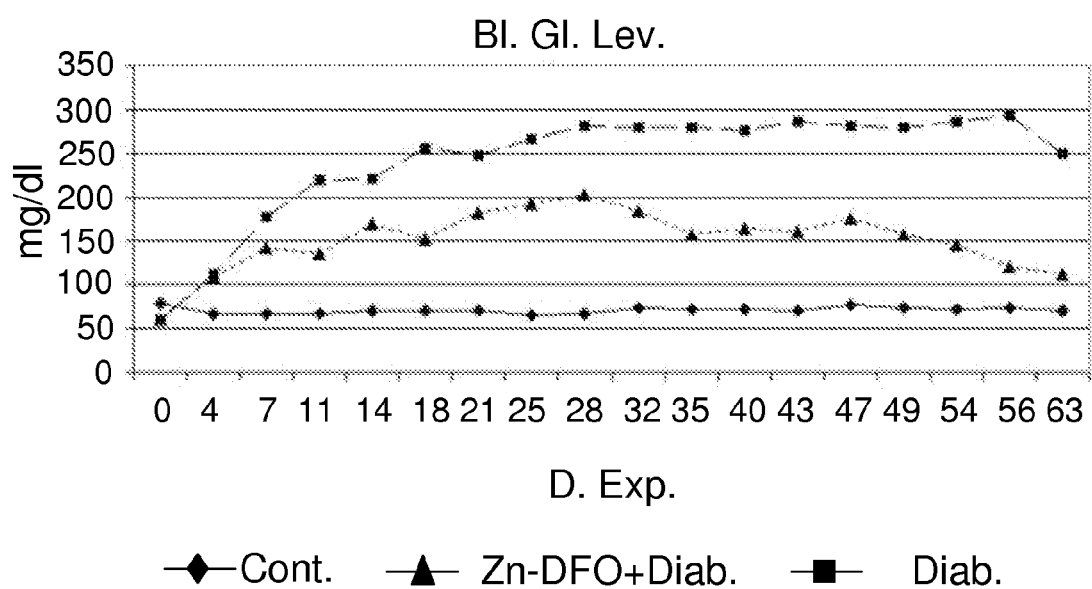

Treatment of Sand Rats Fed on High-energy Diet with Zn-DFO/Ga-DFO Mixture (3:1 Ratio) Attenuates the Rise in Blood Glucose Levels and Improves their Glucose Tolerance FIG. 10A. Blood glucose levels of Zn-DFO/Ga-DFO treated and non-treated high-energy diet fed sand rats. Mean values are shown.

Figure 10B:
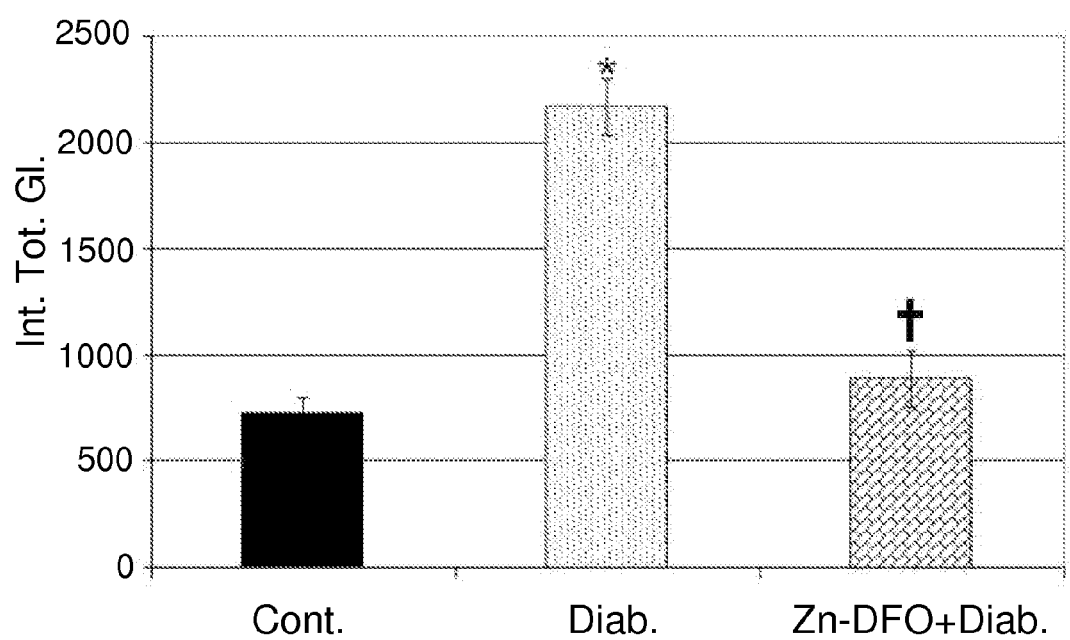

FIG. 10B. Integrated (cumulative) total blood glucose levels during 3 h glucose tolerance test. Mean±S.E.M values are shown *—difference is significant in comparison with Control (normal diet; non-diabetic); †—difference is significant in comparison with diabetics (high-energy diet, treated with vehicle, without the complexes).

Abbreviations: D.Exp. (day of experiment); Diab. (diabetes); Cont. (control); Bl. Gl. Lev. (blood glucose level); Int. Tot. Gl. (integrated total glucose).

FIG. 11

Zn-DFO Inhibits Accumulation of 2,3-Dhabi in High-energy Diet Fed Sand Rats

Blood 2,3-DHBA levels from Zn-DFO treated or non-treated high-energy diet fed sand rats. Mean±S.E.M values are shown *—difference is significant in comparison with Control (normal diet; non-diabetic); †—difference is significant in comparison with diabetics (high-fat diet, treat with vehicle).

Abbreviations: Diab. (diabetes); Cont. (control).

FIG. 12

Zn-DFO Inhibits Cataract Formation in High-energy Diet Fed Sand Rats

Average cataract score for treated or non-treated high-energy diet fed sand rats. Mean±S.E.M values are shown *—difference is significant in comparison with Control (normal diet; non-diabetic); †—difference is significant in comparison with diabetics (high-energy diet, treated with vehicle, without the complexes).

Abbreviations: Diab. (diabetes); Cont. (control); Cat. Sc. (cataract score); Sc. (score).

Figure 13:
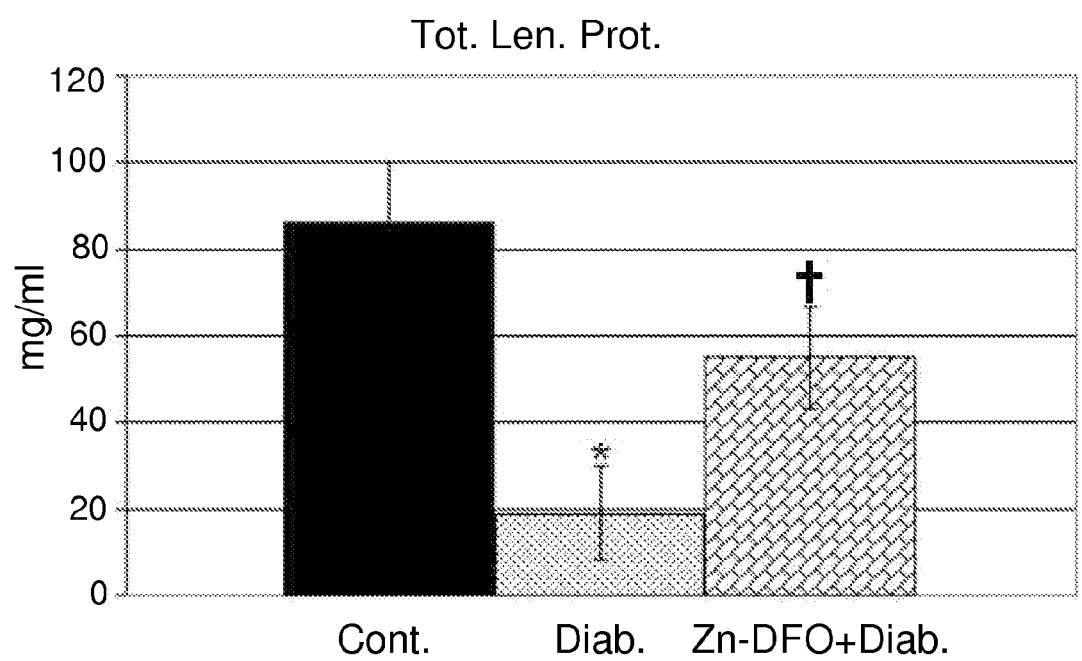

FIG. 13
Zn-DFO Moderates Lens Protein Degradation in High-energy Diet Fed Sand Rats Average lens total protein level in treated and non-treated high-energy diet fed sand rats. Mean±S.E.M values are shown *—difference is significant in comparison with Control (normal diet; non-diabetic); †—difference is significant in comparison with diabetics (high-energy diet, treated with vehicle).

Abbreviations: Diab. (diabetes); Cont. (control); Tot. Len. Prot. (total lens protein).

Figure 14A:
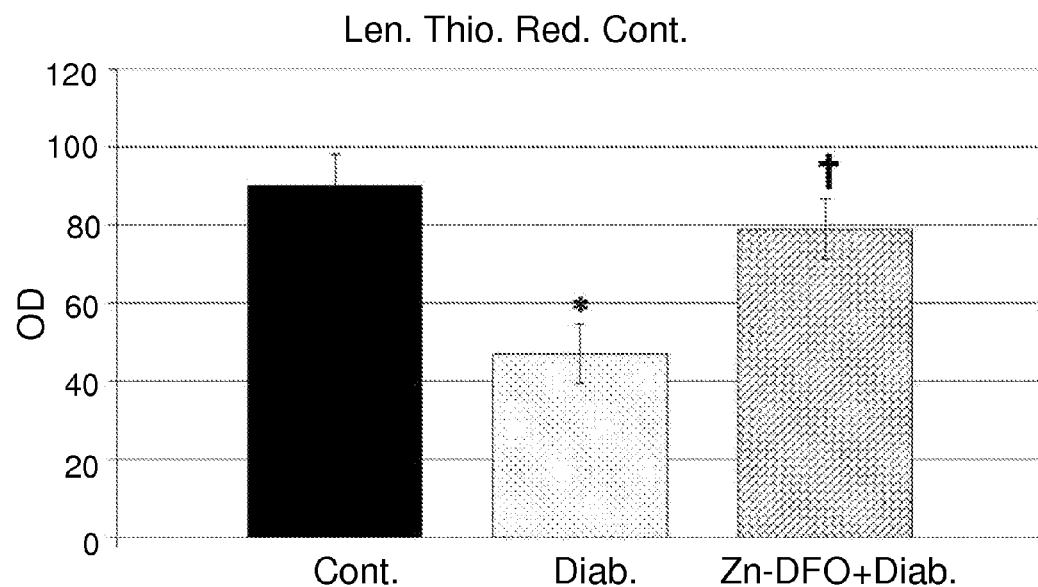
Figure 14B:
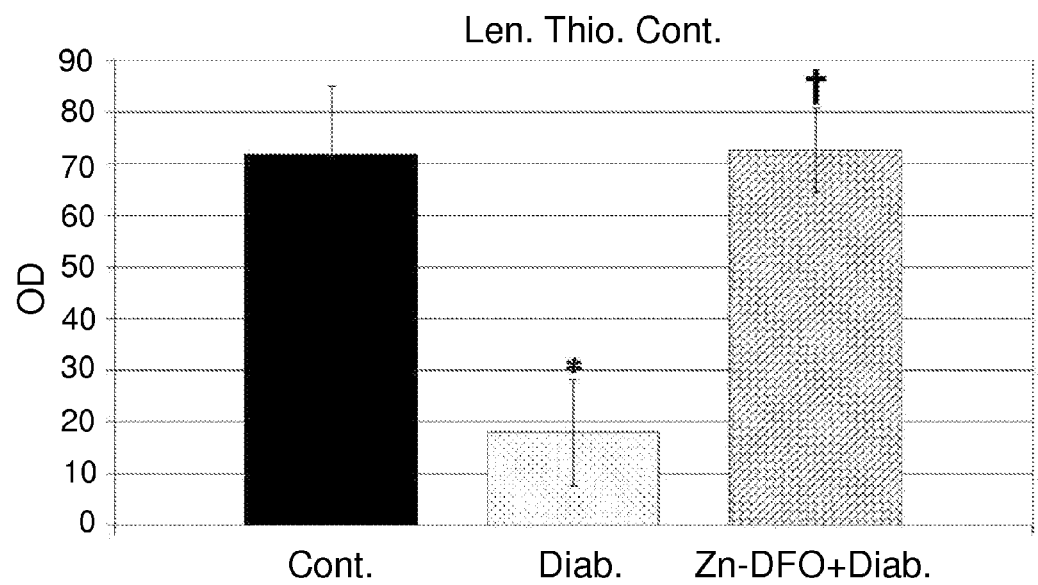

FIG. 14A-14B
Zn-DFO Prevents a Decrease on Thioredoxin Reductase in High-energy Diet Fed Sand Rats FIG. 14A. Average lens thioredoxin reductase levels in treated and non-treated high-energy diet fed sand rats.

FIG. 14B. Average lens thioredoxin concentration in treated and non-treated high-energy diet fed sand rats. Mean±S.E.M values are shown *—difference is significant in comparison with Control (normal diet; non-diabetic); \—difference is significant in comparison with diabetics (high-energy diet, treated with vehicle).

Abbreviations: Diab. (diabetes); Cont. (control); Len. Thio. Red. Cont. (lens thioredoxin reductase content); Len. Thio. Cont. (lens thioredoxin content) OD (optical density).

Figure 15A:
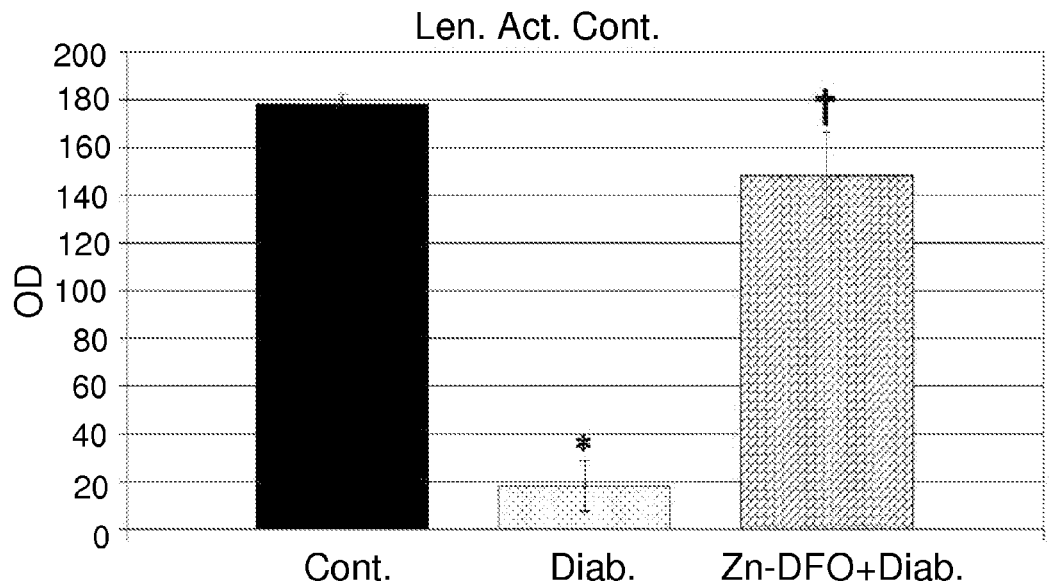
Figure 15B:
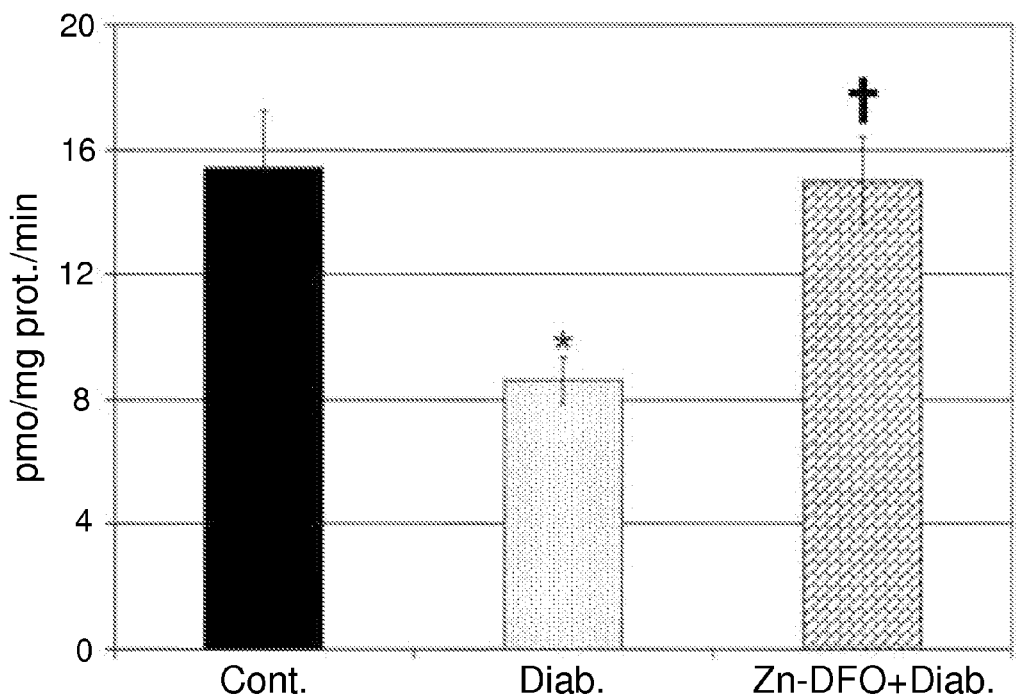

FIG. 15A-15B
Zn-DFO Prevents Actin Degradation and Maintains Msr Activity in High-energy Diet Fed Rats FIG. 15A. Average lens actin concentration in treated and non-treated high-energy diet fed sand rats.

FIG. 15B. Average lens methionine sulfoxide reductase A (Msr) activity in treated and non-treated high-energy diet fed sand rats. Mean±S.E.M values are shown.*—difference is significant in comparison with Control (normal diet; non-diabetic); \—difference is significant in comparison with diabetics (high-energy diet, treated with vehicle).

Abbreviations: Diab. (diabetes); Cont. (control); Len. Act. Cont. (lens actin content); prot. (protein).

Figure 16:
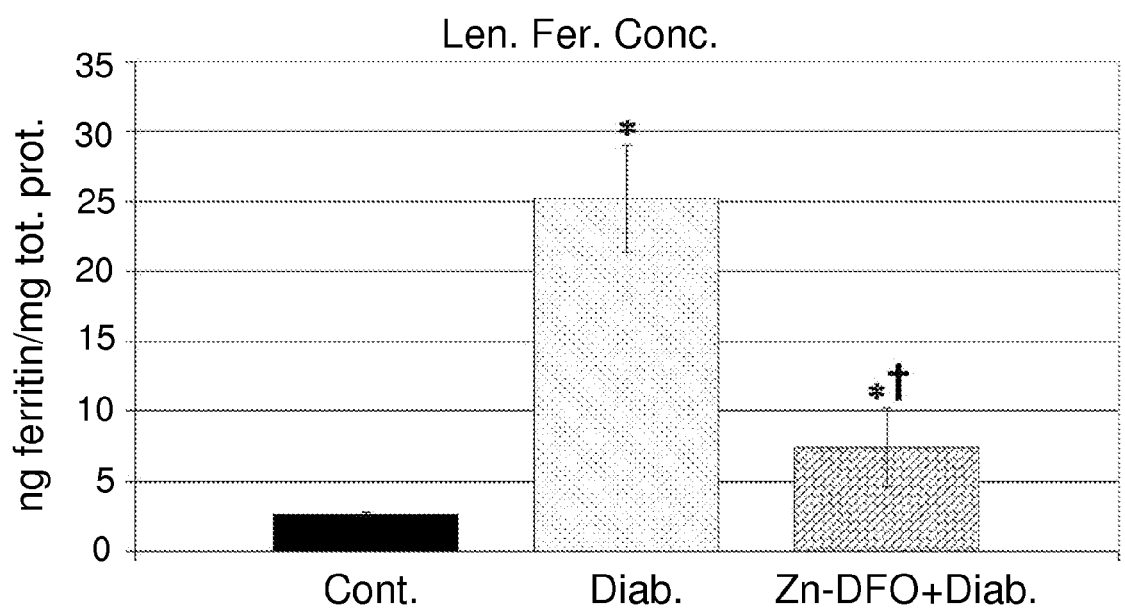

FIG. 16
Zn-DFO Inhibits Ferritin Accumulation in High-energy Diet Fed Sand Rats

Average lens ferritin concentration in treated and non-treated high-energy diet fed sand rats. Mean±S.E.M values are shown *—difference is significant in comparison with Control (normal diet; non-diabetic); †—difference is significant in comparison with diabetics (high-energy diet, treated with vehicle).

Abbreviations: Diab. (diabetes); Cont. (control); Len. Fer. Conc. (lens ferritin concentration); tot. prot. (total protein).

DETAILED DESCRIPTION OF THE INVENTION

The inventors have previously studied the damage caused by caustic burn and the protection provided by topical application of Zn/DFO to the cornea [Siganos, C. et al. (1998) Cornea 17,191-5]. The inventors further previously established the use of such DFO-metal complexes as a topical agent that alleviates the symptoms of exposure to mustard and other chemical warfare agents such as chlorine, phosgene oximine, lewisite, Tabun, Sarin or Soman, which act by mechanisms similar to that of mustard.

Without being bound by any theory, it has been postulated by the inventors that the protective effect of the complexes used in the present invention is the result of suppressed formation of ROS (Reactive Oxygen Species). The ability of the DFO-metal complexes to act via a combined "push-pull" mechanism to achieve such a reduction in free radical formation is supported by both theoretical considerations and previously reported experimental findings. In the Fenton reaction or in the metal-mediated Haber-Weiss mechanism, the conversion of low reactive species to the highly reactive hydroxyl radicals apparently depends on the availability of trace amounts of the redox-active and labile iron or copper ions which serve as essential catalysts [Chevion, M. (1988) id ibid.; Chevion, M. et al. (1993) Proc Natl Acad Sci USA 90, 1102-6; Chevion, M. et al. In: Reactive Oxygen Species in Biological Systems, Colton, G. A. (ed.) (1998) Plenum Press, New York, pp. 103-131]. It is hypothesized that the complex, particularly Zn-DFO or Ga-DFO, exerts its protective effect by intervening in this critical step of hydroxyl radical formation. The two components of each of these complexes, and possibly also of Mn-DFO, when present at or near the site of injury, will reduce the availability and catalytic activity of the redox-active metal ions via the "Push-Pull" mechanisms [Chevion, M. (1991) id ibid.].

The present invention now demonstrates the beneficial effects of treatment with Zn-DFO and Ga-DFO for amelioration or prophylaxis of immune-related pathologies. More specifically, the present invention demonstrates that treatment with the metal complexes of the invention significantly reduces psoriasis symptoms, as well as other skin inflammation disorders. Another example for inflammatory disorder demonstrated by the invention is asthma. The present invention shows that treatment with the DFO-metal complexes of the invention and combinations thereof, reduces the tissue level of ferritin and the total amount of ferritin-bound iron in asthma-related inflamed tissues. The invention further demonstrates reduction of eosinophils and lymphocytes numbers in the peribronchial and alveolar regions, attenuation of the damage to the airway epithelium and mucus overproduction, reduction in neutrophils in bronchoalveolar fluid, reduction of mucous content score, reduction of peribronchial infiltrate value, reduction of epithelial cells metaplasia, reduction of fibrous connective tissue. The invention further demonstrates the beneficial effect of the DFO-metal complexes and combinations thereof in treating diabetes, as an example of immune-related, specifically, inflammatory disorder with possible autoimmune background. More specifically, the invention shows that treatment with the DFO-metal complexes and combinations of the invention prevents the development of key diabetes type II pathologies, including hyperglycemia, increased protein oxidation and degradation, decreased protein activity, and cataract formation. Moreover, although the metal complexes of the invention cannot restore destroyed pancreatic beta cells lost due to diabetes type I, the complexes appear to ameliorate physiological manifestations of the disease.

Thus, in the first aspect, the invention relates to a method of preventing, treating, ameliorating or inhibiting an immune-related disorder, specifically, an inflammatory disorder. The method of the invention comprises the step of administering to a subject in need thereof a therapeutically effective amount of at least one desferrioxamine-metal complex (DFO-metal complex), or any combination thereof or any pharmaceutical composition comprising the same.

It should be appreciated that some of the useful effects exerted by DFO in the context of inhibition of ROS formation is achieved through its actions as a chelator. Chelation is the formation or presence of two or more separate bindings between a polydentate (multiple bonded) ligand and a single central atom. These ligands are called chelants, chelators, chelating agents, or sequestering agents. The ligand forms a chelate complex with the substrate. Chelate complexes are contrasted with coordination complexes with monodentate ligands, which form only one bond with the central atom. Chelants are chemicals that form soluble, complex molecules with certain metal ions, inactivating the ions so that they cannot normally react with other elements or ions.

These chelates often have chemical and biological properties that are markedly different from those of the chelator alone and the metal ion, alone. Desferrioxamine, is a molecule that assumes a noodle-like structure, and can sparingly infiltrates into cells. In contrast, its chelates, like the gallium or iron or zinc, assume a globular structure and infiltrate into cells, for example, crossing the blood-retinal-barrier [Banin and Chevion, 2000, FRBM]. Also, the ferric iron chelate (ferrioxamine) is an inert complex where the iron cannot redox cycle.

The terms "DFO", "desferrioxamine", "Desferal", "deferoxamine B", "desferoxamine B", "DFO-B", "DFOA" or "DFB" as used herein refer to an iron chelating compound of the formula N'-{5-[acetyl (hydroxy)amino]pentyl}-N-[5-({4-[(5-aminopentyl)(hydroxy)amino]-4-oxobutanoyl}amino)pentyl]-N-hydroxy-succinamide. Desferrioxamine (also known as deferoxamine B, desferoxamine B, DFO-B, DFOA, DFB or desferal) is a bacterial siderophore produced by the actinobacter *Streptomyces pilosus*. It has medical applications as a chelating agent used to remove excess iron from the body. The mesylate salt of DFO-B is commercially available. More specifically, the desferrioxamine molecule is made up from six basic units. In this form, when it is not bound to metals, it is a linear molecule that cannot easily penetrate into most cells. Upon metal bindings (such as in ferrioxamine) it forms a globular complex. In addition to iron, desferrioxamine forms tight complexes with—zinc. Based on the similarity of the ligand chemistry between iron or copper, on one hand, and zinc on the other, it is reasonable to assume that the structure of zinc-desferrioxamine is also spherical (rather than linear). In addition, metal binding to the negatively charged desferrioxamine renders the molecule less polar. These considerations might explain why the complexes more easily penetrate through cellular membranes and biological barriers, and more effectively bind intracellular metals that are redox active and mediate tissue damage. In this process two steps provide antioxidant protection: a) the removal of redox-active iron and copper by their chelation, and b) the controlled release of "free" zinc, that in itself possesses anti-oxidant activity.

The relative stability constants for the complexes of desferrioxamine with Fe(III), Cu(II), Zn(II), and Ga(III) are $10^{31}$, $10^{14}$, $10^{11}$, and $10^{28}$ respectively. Thus, based on these thermodynamic considerations, upon penetration into cells, with high abundance of low molecular weight and redox-active complexes of iron or copper, the Zn-desferrioxamine complex exchanges the Zn with iron or copper. In addition to the exchange of zinc for iron or copper, the newly released zinc could have an additional beneficial anti-oxidant effect.

Contemplated DFO-metal-complexes comprise zinc, gallium, manganese, silver, gold, cobalt, indium and lanthanides complexes, specifically, europium (Eu)-DFO complexes, and/or their combinations, preferably zinc-DFO and gallium-DFO.

Thus, some embodiments of the invention relate to the method according to the invention, wherein the metal is selected from any one of zinc, gallium, manganese, indium, silver, gold, cobalt and lanthanides and any combination thereof.

Specific DFO-metal complexes include for example, DFO-Zn, DFO-Ga, DFO-Mn, and the like.

It should be noted that the metal complexes of the invention, specifically, the DFO-metal complexes may use as a metal element, lanthanide Lanthanide or lanthanoid series as used herein comprises the fourteen elements with atomic numbers 58 through 71, including Lanthanum, Cerium, Praseodymium, Neodymium, Promethium, Samarium, Europium, Gadolinium, Terbium, Dysprosium, Holmium, Erbium, Thulium, Ytterbium and Lutetium. In one specific embodiment, the complex used by the invention may be Europium-DFO, and any combinations thereof.

More specifically, in some particular embodiments, the invention relates to a method of treatment, wherein the method comprises the step of administering to a subject in need thereof a therapeutically effective amount of at least one of zinc-desferrioxamine complex (Zn-DFO), gallium-desferrioxamine complex (Ga-DFO), any combination thereof or any composition or combined composition comprising the same.

It should be appreciated that the metal-DFO complexes used by the methods of the invention as well as in the combined compositions and kits of the invention that will be described herein after, may be in any DFO-metal, specifically, Zn or Ga, in any ratio to DFO, specifically, stoichiometric ratio. More specifically, between 1:1 to 0.01:100, more specifically, 0.1:10, even more specifically, 0.1:1.

Some illustrative and non-limiting examples for different ratios of metals, specifically, Zn or Ga to DFO complex are indicated herein below. More particularly, according to certain embodiments, the complex used by the methods of the invention, as well as in the combined compositions and kits of the invention (described herein after) may be prepared as described in Experimental procedures. Alternatively, such complexes may be prepared by mixing 10 mM solution of DFO with an equal volume of 10 mM solution of $ZnCl_2$ solution, titrated to pH between about 5.3 to 5.5, but not over 6.1. The mixture is heated for 30 min. to 45° C., and cooled forming a Zn-DFO complex having a Zn:DFO ratio of 1.0:1.0.

Alternatively, such 1.0:1.0 Zn-DFO complex for the use of the methods, combined compositions and kits of the invention, may be prepared by drying the contents of 1 vial (500 mg, 0.76 mmole) of Desferal®, by adding 168 mg of dry zinc acetate anhydrous (0.76 mmole). Doubly distilled water is added until the contents fully dissolve (~10 ml). The solution is warmed to 40° C. for 45 minutes, cooled down and the complex Zn-DFO (1.0:1.0) is ready to be used.

According to some embodiments, the complex used by the methods, combined compositions and kits of the invention may be prepared by mixing 10 mM solution of DFO with an equal volume of 6 mM of $ZnCl_2$ solution, titrated to pH between about 5.3 to 5.5, but not over 6.1. The mixture is heated for 30 min. to 45° C., and cooled forming a Zn-DFO complex with a stoichiometric ratio of Zn:DFO of 0.6:1.0.

The complex used by the methods, combined compositions and kits of the invention may also be prepared by mixing 10 mM DFO solution with an equal volume of 12.5 mM of $ZnCl_2$ solution and with 10 ml of 5.5 mM Histidine, titrated to pH between about 5.3 to 5.5, but not over 6.1. The mixture is heated for 30 min. to 45° C., and cooled forming the Zn-DFO complex having a Zn:DFO ratio of 1.25:1.0.

Other such embodiments contemplate the complex used by the methods, combined compositions and kits of the invention, may be prepared by mixing 50 mM DFO solution with ⅕ the volume of 50 mM solution of $ZnSO_4$. The mixture is heated to for 45 min to 40° C. and cooled to form the resultant Zn/DFO (5 nM) complex having a Zn:DFO ratio of 0.2:1.0.

It should be recognized that complexes having other Zn:DFO ratios may be used for the methods, combined compositions and kits of the invention.

In some embodiments, the complex used by the methods, combined compositions and kits of the invention, may be prepared by the mixing of 10 mM solution of DFO with an equal volume of 10 mM of $GaCl_3$ solution, titrating to pH 5.0 with HCl and then with NaOH (1M) to pH between about 5.4 to 5.6, but not over 5.6, forming a Ga-DFO complex having a Ga:DFO ratio of 1.0:1.0.

Other embodiments consider the complex used by the methods, combined compositions and kits of the invention, may be prepared by mixing 5 mM solution of DFO with an equal volume of 3 mM solution of $GaCl_3$ solution and titrating to pH between about 5.4 to 5.6, but not over 5.6 forming a Ga-DFO complex having a Ga:DFO of 0.6:1.0.

It should be appreciated that complexes having any other Ga:DFO ratios may be used for the methods, combined compositions and kits of the invention.

In more specific embodiments, the method of the invention may optionally further comprise the step of administering at least one additional therapeutic agents including reduced dose of currently used drugs, enhancers of absorption, and other therapeutic agents as detailed herein.

These additional therapeutic agents, specifically, any immunomodulatory agent or known medicament, may be either combined with at least one of the metal-DFO complexes used by the invention or may be administered separately in an additional separate step having an optional different mode of administration.

In more specific embodiments, the method optionally further comprises the step of administering at least one additional therapeutic agent including currently available medicines e.g. montelukast and/or any other therapeutic agent with similar mode of action, omazulimab and/or any other therapeutic agent with similar mode of action, salmeterol and/or any other therapeutic agent with similar mode of action, fluticasone and/or any other therapeutic agent with similar mode of action, nedocromil and/or any other therapeutic agent with similar mode of action, epinephrine and/or any other therapeutic agent with similar mode of action, ipatropium and/or any other therapeutic agent with similar mode of action, tolbutamide and/or any other therapeutic agent with similar mode of action, glipizide and/or any other therapeutic agent with similar mode of action, meglitinide and/or any other therapeutic agent with similar mode of action, rosiglitazone and/or any other therapeutic agent with similar mode of action, metformin and/or any other therapeutic agent with similar mode of action, miglitol and/or any other therapeutic agent with similar mode of action, exenatide and/or any other therapeutic agent with similar mode of action, vildagliptin and/or any other therapeutic agent with similar mode of action, pramlintide and/or any other therapeutic agent with similar mode of action, aleglitazar and/or any other therapeutic agent with similar mode of action, imeglimin and/or any other therapeutic agent with similar mode of action, insulin and/or insulin analogues and/or any other therapeutic agent with similar mode of action, analpram and/or any other therapeutic agent with similar mode of action, clobex and/or any other therapeutic agent with similar mode of action, deltasone and/or any other therapeutic agent with similar mode of action, dovonex and/or any other therapeutic agent with similar mode of action, enbrel and/or any other therapeutic agent with similar mode of action, humira and/or any other therapeutic agent with similar mode of action, neoral and/or any other therapeutic agent with similar mode of action and/or any other agents, improving medicine activity e.g. salycilate, aspirin, vitamin C, lipoic acid, vitamin B12 and/or percutaneous penetration enhancers e.g. azone and/or any other therapeutic agent with similar mode of action, benzalkonium chloride and/or any other therapeutic agent with similar mode of action, polyethylene glycol and/or any other therapeutic agent with similar mode of action, menthol and/or any other therapeutic agent with similar mode of action, ketoprofen and/or any other therapeutic agent with similar mode of action, 4-Decyloxazolidin-2-one and/or any other therapeutic agent with similar mode of action, S,S-dimethyl-N-(5-nitro-2-pyridyl) iminosulfurane and/or any other therapeutic agent with similar mode of action.

The methods of the invention disclose the use of DFO-metal complexes, specifically, Zn-DFO, Ga-DFO, any combination thereof or any DFO-metal complex described herein before for preventing, treating, ameliorating or inhibiting an immune-related disorder. In yet more specific embodiments, the immune-related disorder according to the method of treatment of the invention is any one of an inflammatory disease and an autoimmune disease. The findings presented herein indicate clear advantages concurrent with low toxicity of Zn-DFO and Ga-DFO in treatment of psoriasis, asthma, diabetes and any immune-related disorders.

In certain specific embodiments the methods of the invention are particularly applicable for treating immune-related disorders such as inflammatory disease, for example, a chronic or acute inflammatory-related skin pathologic condition or a respiratory disease, and immune-related disorders having an autoimmune background, such as diabetes. Specifically, diabetes type II, diabetes type I or any diabetes related condition. More specifically, the present invention relates to uses of Zn-DFO, Ga-DFO and any combination thereof for treating such immune-related disorders.

As shown by Examples 9-12, the complexes of the invention exhibit beneficial effect when topically applied on skin of psoriasis patients. In psoriasis, one or more of the immune system's signaling molecules trigger events leading to a local excess of free radical and other reactive oxygen-derived and nitrogen-derived species. The production of excess reactive species, in particular the highly deleterious hydroxyl radical, is catalyzed by redox-active and labile iron. Signaling molecules, released by skin cells altered or damaged by these reactive cytotoxic species, are causative agents leading to psoriasis. Thus, in psoriasis, an amplified skin cell-altering or damaging feedback loop may result. In psoriasis, proliferating psoriatic keratinocytes are in need for iron. Limiting the availability of labile iron will halt the rapidly proliferation of skin cells, and will limit the psoriatic inflammation.

Therefore, in particularly specific embodiments, the invention provides methods for treating chronic or acute inflammatory-related skin pathologic condition, specifically, psoriasis, using metal-DFO complexes and any combinations, composition, combined compositions and kits thereof.

More particularly, psoriasis is a common skin condition that features patchy, raised, red areas of skin inflammation with scaling. Psoriasis often affects the tips of the elbows and knees, the scalp, the navel, and the area surrounding the genitals or anus. It occurs when the immune system sends out faulty signals that speed up the growth cycle of skin cells. The scaly patches commonly caused by psoriasis, called psoriatic plaques, are areas of inflammation and excessive skin production. Skin rapidly accumulates at these sites which gives it a silvery-white appearance. Plaques frequently occur on the skin of the elbows and knees, but can affect any area including the scalp, palms of hands and soles of feet, and genitals. In contrast to eczema, psoriasis is more likely to be found on the outer side of the joint. The disorder is a chronic recurring condition that varies in severity from minor localized patches to complete body coverage. Fingernails and toenails are frequently affected (psoriatic nail dystrophy) and can be seen as an isolated symptom. Psoriasis can also cause inflammation of the joints, which is known as psoriatic arthritis. Ten to fifteen percent of people with psoriasis develop psoriatic arthritis. There are many treatments available, but because of its chronic recurrent nature psoriasis is a challenge to treat. The symptoms of psoriasis can manifest in a variety of forms. Variants include plaque, pustular, guttate and flexural psoriasis. Psoriasis may be classified into nonpustular and pustular types. It should be noted that the methods of the invention contemplate the treatment of Nonpustular as well as Pustular psoriasis.

More specifically, Nonpustular psoriasis includes Psoriasis vulgaris and Psoriatic erythroderma. Psoriasis vulgaris (also known as Chronic stationary psoriasis or Plaque-like psoriasis), is the most common form of psoriasis. It affects 80 to 90% of people with psoriasis. Plaque psoriasis typically appears as raised areas of inflamed skin covered with silvery white scaly skin. These areas are called plaques.

Psoriatic erythroderma (Erythrodermic psoriasis) involves the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. This form of psoriasis can be fatal, as the extreme inflammation and exfoliation disrupt the body's ability to regulate temperature and for the skin to perform barrier functions.

In yet another specific embodiment, the methods of the invention may be used for treating Pustular psoriasis. Pustular psoriasis appears as raised bumps that are filled with non-infectious pus (pustules). The skin under and surrounding the pustules is red and tender. Pustular psoriasis can be localized, commonly to the hands and feet (palmoplantar pustulosis), or generalized with widespread patches occurring randomly on any part of the body. Pustular psoriasis subtypes include Generalized pustular psoriasis (Pustular psoriasis of von Zumbusch), Pustulosis palmaris et plantaris (Persistent palmoplantar pustulosis, Pustular psoriasis of the Barber type, Pustular psoriasis of the extremities), Annular pustular psoriasis, Acrodermatitis continua and Impetigo herpetiformis.

It should be appreciated that the methods of the invention may be also applicable for treating any additional types of psoriasis, for example, Drug-induced psoriasis, Inverse psoriasis, or flexural psoriasis, appears as smooth inflamed patches of skin. It occurs in skin folds, particularly around the genitals (between the thigh and groin), the armpits, under an overweight stomach (pannus), and under the breasts (inframammary fold). It is aggravated by friction and sweat, and is vulnerable to fungal infections.

Still further, the method of the invention may be used for treating Guttate psoriasis. This type pf psoriasis is characterized by numerous small, scaly, red or pink, teardrop-shaped lesions. These numerous spots of psoriasis appear over large areas of the body, primarily the trunk, but also the limbs, and scalp. Guttate psoriasis is often preceded by a streptococcal infection, typically streptococcal pharyngitis.

Nail psoriasis that may be also treated by the method of the invention produces a variety of changes in the appearance of finger and toe nails. These changes include discoloring under the nail plate, pitting of the nails, lines going across the nails, thickening of the skin under the nail, and the loosening (onycholysis) and crumbling of the nail.

In yet another embodiment, the method of the invention may be used for treating psoriatic arthritis. Psoriatic arthritis involves joint and connective tissue inflammation. Psoriatic arthritis can affect any joint but is most common in the joints of the fingers and toes. This can result in a sausage-shaped swelling of the fingers and toes known as dactylitis. Psoriatic arthritis can also affect the hips, knees and spine (spondylitis). About 10-15% of people who have psoriasis also have psoriatic arthritis.

In some embodiments, treatment of a subject suffering from psoriasis may improve the physiological state of the subject, for example, smoothing skin that was rough due to the disease. In preferred embodiments, topical application of the metal-complexes of the invention does not irritate the skin and does not promote inflammation.

In specific embodiments, an exemplary concentration of the complex/es in water, effective for treatment of psoriasis and other contemplated inflammatory skin disorders, such as that of the exemplary Ga-DFO or Zn-DFO, may range typically between about 0.01% weight/volume and about 5.0% weight/volume, more specifically, between about 0.10% weight/volume and about 2.5%, between about 0.10% weight/volume and about 1.0% weight/volume, and more specifically, 0.1, 0.2, 0.3, 0.4, 0.5, 0.6, 0.7, 0.8, 0.9 and 1.0%. One specific embodiment such concentration may range between about 0.2% weight/volume and about 0.6% weight/volume. In the organic matrices the concentration of the complex/es is typically greater than about 0.03% weight/volume and less than about 5.0% weight/volume; the preferred concentration being greater than about 0.05 weight %, more specifically, greater than 0.09 weight % and less than 0.45 weight %, as shown in Example 9.

It should be appreciated that other chronic or acute inflammatory-related skin pathologic conditions may be treated by the method of the invention. Such additional conditions include dermatitis, acne, cold bites, mechanical injuries, insect bites, inflammatory skin injuries, inflammatory-related disturbances of skin pigmentation, for example, Vitiligo and eczemas.

More specifically, certain embodiments of the invention relates to method of treating dermatitis. The term "dermatitis" refers to inflammation of the skin, in general. The different kinds usually have in common an allergic reaction to specific allergens. The term may be used to refer to eczema, which is also known as dermatitis eczema or eczematous dermatitis. A diagnosis of eczema often implies atopic dermatitis (childhood eczema), but without proper context, it means nothing more than a "rash", i.e. a transient skin inflammation. In some languages, "dermatitis" and eczema are synonyms, while in other languages "dermatitis" implies an acute condition and "eczema" a chronic one. The two conditions are often classified together.

Acne is another non-limiting example for skin inflammatory disorders that may be treated by the method of the invention. Acne is a general term used for eruptive disease of the skin. It is sometimes used as a synonym for Acne vulgaris. However, there are several different types of acne. These include Acne vulgaris, Acne conglobata, Acne miliaris necrotica, Tropical acne, Infantile acne/Neonatal acne, Excoriated acne, Acne fulminans, Drug-induced acne/Acne medicamentosa (Steroid acne), Halogen acne (Iododerma, Bromoderma, Chloracne), Oil acne, Tar acne, Acne cosmetica, Occupational acne, Acne aestivalis, Acne keloidalis nuchae, Acne mechanica, Acne with facial edema, Pomade acne, Acne necrotica, Blackhead, and Lupus miliaris disseminatus faciei.

Inflammatory-related skin disorder that may be treated by the method of the invention may include also insect bites and stings. Insect bites occur when an insect is agitated and seeks to defend itself through its natural defense mechanisms, or when an insect seeks to feed off the bitten person. Insects inject formic acid, which can cause an immediate skin reaction often resulting in redness and swelling in the injured area. The sting from fire ants, bees, wasps and hornets are usually painful, and may stimulate a dangerous allergic reaction called anaphylaxis for at-risk patients, and some wasps can also have a powerful bite along with a sting. Bites from mosquitoes, fleas, and mites are more likely to cause itching than pain. The skin reaction to insect bites and stings usually lasts for up to a few days. However, in some cases the local reaction can last for up to two years. The reaction to a sting is of three types. The normal reaction involves the area around the bite with redness, itchiness, and pain. A large local reaction occurs when the area of swelling is greater than five cm. Systemic reactions are when symptoms occur in areas besides that of the bites.

In yet another embodiment, the method of the invention may be applicable for treating Vitiligo. Vitiligo as used herein is a chronic disorder that causes depigmentation of patches of skin. It occurs when melanocytes, die or are unable to function. The cause of vitiligo is unknown, but research suggests that is may arise from autoimmune, genetic, oxidative stress, neural, or viral causes. The incidence worldwide is less than 1%, with the most common form being non-segmental vitiligo. Symptoms usually begin between ages 10 years and age 30 years, including whitening or graying of hair, loss of skin color inside the mouth and loss of eye color. The most notable symptom of vitiligo is depigmentation of patches of skin that occurs on the extremities. In non-segmental vitiligo (NSV), there is usually some form of symmetry in the location of the patches of depigmentation. New patches also appear over time and can be generalised over large portions of the body or localised to a particular area. Vitiligo where little pigmented skin remains is referred to as vitiligo universalis. NSV can come about at any age, unlike segmental vitiligo which is far more prevalent in teenage years. Classes of non-segmental Vitiligo include Generalized Vitiligo, Universal Vitiligo, Focal Vitiligo, Acrofacial Vitiligo and Muscosal Vitiligo. Segmental vitiligo (SV) differs in appearance, aetiology and prevalence from associated illnesses. Its treatment is different from that of NSV. It tends to affect areas of skin that are associated with dorsal roots from the spine. It spreads much more rapidly than NSV and, without treatment, it is much more stable/static in course and not associated with autoimmune diseases and a very treatable condition that responds to topical treatment.

It should be noted that in certain embodiments the methods, compositions, combined compositions and kits of the invention may be applicable in treating any inflammatory skin disorder provided that such disorder is not induced following exposure to nitrogen and other mustard gases, as well as other warfare agent, e.g. Sarin.

As indicated above, the method of the invention may be suitable for treating inflammatory skin disorders. The invention has further demonstrated methods that may be also applicable for treating and preventing inflammatory respiratory disease. More specifically, Examples 1-4 clearly disclose the beneficial effect of the metal-DFO complexes of the invention in treating asthma. Thus, in specific embodiments, the method of the invention may be used for the prophylaxis, treatment and/or amelioration of respiratory disorders, specifically, asthma.

Asthma is a common chronic inflammatory disease of the airways characterized by variable and recurring symptoms, airflow obstruction, and bronchospasm. Symptoms include wheezing, coughing, chest tightness, and shortness of breath.

Asthma is clinically classified according to the frequency of symptoms, forced expiratory volume in one second (FEV1), and peak expiratory flow rate. Asthma may also be classified as atopic (extrinsic) or non-atopic (intrinsic), based on whether symptoms are precipitated by allergens (atopic) or not (non-atopic).

Asthma is controlled by environmental and genetic factors. These factors influence how severe asthma is and how well it responds to medication. The interaction is complex and not fully understood.

Prevention of the development of asthma is different from prevention of asthma episodes. Aggressive treatment of mild allergy with immunotherapy has been shown to reduce the likelihood of asthma development. In controlling symptoms, the first step is establishing a plan of action to prevent episodes of asthma by avoiding triggers and allergens, regularly testing for lung function, and using preventive medications.

Medications used to treat asthma are divided into two general classes: quick-relief medications used to treat acute symptoms and long-term control medications used to prevent further exacerbation.

Fast acting medications include short-acting, selective beta2-adrenoceptor agonists, such as salbutamol (albuterol USAN), levalbuterol, terbutaline and bitolterol. Older, less selective adrenergic agonists, such as inhaled epinephrine and ephedrine tablets, have also been used; the brand Primatene Mist, for example. When used solely as a relief medication, inhaled epinephrine has been shown to be an effective agent to terminate an acute asthmatic exacerbation. Anticholinergic medications, such as ipratropium bromide may be used instead.

Long term control medications include inhaled glucocorticoids, mainly considered as preventive medications, while oral glucocorticoids are often used to supplement treatment of emergent moderate to severe attacks. Long-acting $\beta$2-agonists (LABD) are similar in structure to short-acting selective beta2-adrenoceptor agonists, but have much longer side chains resulting in a 12-hour effect.

Importantly, the metal-chelator, specifically, metal-DFO complexes of the invention provide an additional therapeutic dimension to the current available medications, as they do not only serve as preventive measures against the development of the described respiratory disorder pathologies, but also diminish the ensuing tissue damage.

It should be noted that medications for asthma and other repiratory-associated disorders are typically provided as metered-dose inhalers (MDIs) in combination with an asthma spacer or as a dry powder inhaler. The spacer is a plastic cylinder that mixes the medication with air, making it easier to receive a full dose of the drug. A nebulizer may also be used. The metal-DFO complexes of the invention may be therefore administered using such MDIs, and may be also combined with any other asthma medications, specifically those indicated above.

As indicated above, the present invention contemplates methods for the treatment of different immune-related respiratory diseases. In addition to asthma, such respiratory diseases may include any other acute allergy manifestations in airways, chronic rhinosinusitis (CRS), allergic rhinitis, COPD, nasal polyposis (NP), vasomotor rhinitis, airways hyper-responsiveness, cystic fibrosis and lung fibrosis, or allergic sinusitis. The invention therefore provides methods, combined compositions and kits for preventing, treating, ameliorating or inhibiting any of the respiratory diseases described above.

Thus, in certain embodiments, the invention provides methods, combined compositions and kits for treating sinusitis. Sinusitis is inflammation of the paranasal sinuses, which may be due to infection, allergy or autoimmune issues. Most cases are due to a viral infection and resolve over the course of 10 days. It is a common condition with more than 24 million cases occurring in the United States annually.

Chronic sinusitis, by definition, lasts longer than three months and can be caused by many different diseases that share chronic inflammation of the sinuses as a common symptom. Chronic sinusitis cases are subdivided into cases with polyps and cases without polyps. When polyps are present, the condition is called chronic hyperplastic sinusitis; however, the causes are poorly understood and may include allergy, environmental factors such as dust or pollution, bacterial infection, or fungus (either allergic, infective, or reactive). Non-allergic factors, such as vasomotor rhinitis, can also cause chronic sinus problems.

Allergic rhinitis, pollenosis or hay fever that may be treated by the method of the invention, is an allergic inflammation of the nasal airways. It occurs when an allergen such as pollen or dust is inhaled by an individual with a sensitized immune system, and triggers antibody production. These antibodies mostly bind to mast cells, which contain histamine. When the mast cells are stimulated by pollen and dust, histamine (and other chemicals) is released. This causes itching, swelling and mucus production. Symptoms vary in severity between individuals. Very sensitive individuals can experience hives or other rashes.

Chronic obstructive pulmonary disease (COPD), also known as chronic obstructive lung disease (COLD), chronic obstructive airway disease (COAD), chronic airflow limitation (CAL) and chronic obstructive respiratory disease (CORD), refers to chronic bronchitis and emphysema, a pair of commonly co-existing diseases of the lungs in which the airways become narrowed. This leads to a limitation of the flow of air to and from the lungs causing shortness of breath. In contrast to asthma, the limitation of airflow is poorly reversible and usually gets progressively worse over time. COPD is caused by noxious particles or gas, most commonly from tobacco smoking, which triggers an abnormal inflammatory response in the lung. The inflammatory response in the larger airways is known as chronic bronchitis, which is diagnosed clinically when people regularly cough up sputum. In the alveoli, the inflammatory response causes destruction of the tissues of the lung, a process known as emphysema. The natural course of COPD is characterized by occasional sudden worsening of symptoms called acute exacerbations, most of which are caused by infections or air pollution. The methods, combined compositions and kits of the invention are applicable for treating COAD and COPD.

Still further, the method of the invention may be used for treating Nasal polyps. Nasal polyps are polypoidal masses arising mainly from the mucous membranes of the nose and paranasal sinuses. They are overgrowths of the mucosa that frequently accompany allergic rhinitis. They are freely moveable and non-tender. Nasal polyps are usually classified into antrochoanal polyps and ethmoidal polyps. Antrochoanal polyps arise from the maxillary sinuses and are the much less common, ethmoidal polyps arise from the ethmoidal sinuses. Antrochoanal polyps are usually single and unilateral whereas ethmoidal polyps are multiple and bilateral.

Non-allergic rhinitis refers to runny nose that is not due to allergy. Non-allergic rhinitis can be classified as either non-inflammatory or inflammatory rhinitis. One very common type of non-inflammatory, non-allergic rhinitis that is sometimes confused with allergy is called vasomotor rhinitis, in which certain non-allergic triggers such as smells, fumes, smoke, dusts, and temperature changes, cause rhinitis. It is thought that these non-allergic triggers cause dilation of the blood vessels in the lining of the nose, which results in swelling, and drainage. Vasomotor rhinitis can coexist with allergic rhinitis, and this is called "mixed rhinitis" Vasomotor rhinitis appears to be significantly more common in women than men, leading some researchers to believe that hormones play a role. In general, age of onset occurs after 20 years of age, in contrast to allergic rhinitis which can be developed at any age. Individuals suffering from vasomotor rhinitis typically experience symptoms year-round, though symptoms may exacerbate in the spring and autumn when rapid weather changes are more common. An estimated 17 million United States citizens have vasomotor rhinitis. The antihistamine azelastine has been shown to be effective for allergic, mixed and vasomotor rhinitis.

Airway hyperresponsiveness (or other combinations with bronchial or hyperreactivity) is a state characterized by easily triggered bronchospasm (contraction of the bronchioles or small airways). Airway hyperresponsiveness can be assessed with a bronchial challenge test. This most often uses products like metacholine or histamine. These chemicals trigger bronchospasm in normal individuals as well, but people with bronchial hyperresponsiveness have a lower threshold. Bronchial hyperresponsiveness is a hallmark of asthma but also occurs frequently in people suffering from chronic obstructive pulmonary disease (COPD). In the Lung Heart Study, bronchial hyperresponsiveness was present in approximately two-thirds of patients with non-severe COPD, and this predicted lung function decline independently of other factors. In asthma it tends to be reversible with bronchodilator therapy, while this is not the case in COPD.

Cystic fibrosis (also known as CF) that is another example for conditions that may be treated by the method of the invention is a common disease which affects the entire body, causing progressive disability and often early death. The name cystic fibrosis refers to the characteristic scarring (fibrosis) and cyst formation within the pancreas. Difficulty breathing is the most serious symptom and results from frequent lung infections that are treated, though not cured, by antibiotics and other medications. A multitude of other symptoms, including sinus infections, poor growth, diarrhea, and infertility result from the effects of CF on other parts of the body. CF is caused by a mutation in the gene for the protein cystic fibrosis transmembrane conductance regulator (CFTR), and is considered as an autosomal recessive disease.

Pulmonary fibrosis is the formation or development of excess fibrous connective tissue (fibrosis) in the lungs. It can be described as "scarring of the lung". Pulmonary fibrosis involves gradual replacement of normal lung parenchyma with fibrotic tissue. Thickening of scar tissue causes irreversible decrease in oxygen diffusion capacity. In addition, decreased compliance makes pulmonary fibrosis a restrictive lung disease. It is the main cause of restrictive lung disease that is intrinsic to the lung parenchyma.

In particular embodiments, treatment of the respiratory immune-related disorder by the method of the invention leads to beneficial effect in many parameters improving the diseased subject's symptoms. In certain embodiments, such improvement may be demonstrated by at least one of reduction in tissue ferritin concentration, reduction in total ferritin-bound iron in nasal polyps and/or lungs, reduction of eosinophils and lymphocytes numbers in the peribronchial and alveolar regions, attenuation of the damage to the airway epithelium and mucus overproduction, reduction in neutrophils in Bronchoalveolar fluid, reduction of mucous content score, reduction of peribronchial infiltrate value, reduction of epithelial cells metaplasia, reduction of fibrous connective tissue, in a subject suffering of a respiratory diseases, specifically, asthma.

Some embodiments of the invention contemplate a treatment of a subject suffering from respiratory diseases, specifically, asthma, with the metal-DFO complexes of the invention, specifically, the Zn-DFO, and/or Ga-DFO, wherein the treatment results in the inhibition of respiratory diseases-induced increase in tissue ferritin by about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%, specifically, about 30% to about 50%, more specifically, about 35% to about 45%, for example, any one of 35, 36, 37, 38, 39, 40, 41, 42, 43, 44 and 45% as illustrated by Example 4.

Specific embodiments of the invention contemplate a treatment of a subject suffering from respiratory diseases, such as asthma, with the metal-DFO complexes of the invention, wherein the treatment results in the inhibition of respiratory diseases-induced increase in total ferritin-bound iron in nasal polyps and/or lungs by about 5% to about 100%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%, more specifically, about 98% to about 100%, as illustrated by Example 4.

Other embodiments of the invention consider a treatment of a subject suffering from respiratory diseases, specifically asthma, with the metal-DFO complexes of the invention, wherein the treatment results in the inhibition of respiratory diseases-induced increase in eosinophils, and lymphocytes numbers in the peribronchial and alveolar regions and neutrophils in bronchoalveolar fluid by about 5% to about 100%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%, more specifically, about 98% to about 100%, as illustrated by Example 4.

Some embodiments of the invention consider a treatment of a subject suffering from respiratory diseases, specifically asthma, with the metal-DFO complexes of the invention, wherein the treatment results in the reduction of infiltration of inflammatory cells to the lungs, as judged by integer-graded histological sections evaluation, by about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95% or about 95% to about 99.9%.

Some embodiments of the invention contemplate a treatment of a subject suffering from respiratory diseases, specifically asthma, with the metal-DFO complexes of the invention, wherein the treatment results in the reduction of structural damage to the airway epithelium and goblet cell metaplasia and hyperplasia, as judged by integer-graded histological sections evaluation, by about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95% or about 95% to about 99.9%.

Some embodiments of the invention consider a treatment of a subject suffering from respiratory diseases, specifically asthma, with the metal-DFO complexes of the invention, wherein the treatment results in the reduction of mucus overproduction, as judged by integer-graded histological sections evaluation, by about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95% or about 95% to about 99.9%.

Some embodiments of the invention consider a treatment of a subject suffering from respiratory diseases, specifically from systemic or lung paraquat poisoning, with the metal-DFO complexes of the invention, wherein the treatment results in the reduction of scarring of the airways, by about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95% or about 95% to about 99.9%.

Some embodiments of the invention consider a treatment of a subject suffering from respiratory diseases, specifically from asthma, with the metal-DFO complexes of the invention, wherein the treatment results in the reduction of scarring of the airways, by about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95% or about 95% to about 99.9%.

It should be noted that in certain embodiments the methods, compositions, combined compositions and kits of the invention may be applicable in treating any inflammatory respiratory disorder provided that such disorder is not induced following exposure to nitrogen and other mustard gases, as well as other warfare agent, e.g. Sarin.

The mechanism of action of the invention affects a wide spectrum of pathological conditions, as it inhibits the production of ROS, which play an important role in immune-related disorders in general. The present invention clearly show in Examples 5-8 in the first time that the DFO-metal complexes of the invention are also applicable for treating another immune-related condition, for example, an autoimmune disorder such as diabetes.

Thus, in specific embodiments, the method of the invention also relates to the prophylaxis, treatment and/or amelioration of diabetes type II, diabetes type I or any diabetes related condition.

Diabetes mellitus is a syndrome characterized by disordered metabolism and inappropriately high blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision, these symptoms are likely absent if the blood sugar is only mildly elevated.

There are three main forms of diabetes: type I, type II and gestational diabetes (occurs during pregnancy). Type I diabetes mellitus is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type I diabetes. Most affected people are otherwise healthy and of a healthy weight when onset occurs. Sensitivity and responsiveness to insulin are usually normal, especially in the early stages. Type I diabetes can affect children or adults and was traditionally termed "juvenile diabetes" as it represents a majority of cases of diabetes affecting children.

The principal treatment of type I diabetes, even from the earliest stages, is replacement of insulin combined with careful monitoring of blood glucose levels using blood testing monitors. Without insulin, diabetic ketoacidosis can develop and may result in coma or death. Emphasis is also placed on lifestyle adjustments (diet and exercise) though these cannot reverse the loss. Apart from the common subcutaneous injections, it is also possible to deliver insulin by a pump, which allows continuous infusion of insulin 24 hours a day at preset levels, and the ability to program doses (a bolus) of insulin as needed at meal times.

As shown in Example 8, treatment of animals suffering of type I diabetes with the metal-DFO complexes of the invention and combinations thereof, improved general health status of the treated subjects. Therefore, according to one embodiment, the method of the invention is applicable for preventing, treating, ameliorating or inhibiting diabetes type I. In some embodiments, treatment of a subject suffering from diabetes type I with the metal-DFO complexes of the invention inhibits the appearance of skin blemishes and localized pigmentation changes. In other embodiments, said treatment ameliorates at least one of frequent micturition, increased sweating and ketone odor, typical to diabetes type I.

The terms "inhibition", "moderation" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

Diabetes mellitus type II—formerly non-insulin-dependent diabetes mellitus (NIDDM) or adult-onset diabetes—is a metabolic disorder that is characterized by high blood glucose in the context of insulin resistance and relative insulin deficiency.

Insulin resistance means that body cells do not respond appropriately when insulin is present. Unlike type I diabetes mellitus, insulin resistance is generally "post-receptor", meaning it is a problem with the cells that respond to insulin rather than a problem with the production of insulin. This is a more complex problem than type I, but is sometimes easier to treat, especially in the early years when insulin is often still being produced internally. Severe complications can result from improperly managed type II diabetes, including renal failure, erectile dysfunction, blindness, slow healing wounds (including surgical incisions), and arterial disease, including coronary artery disease. The onset of type II has been most common in middle age and later life, although it is being more frequently seen in adolescents and young adults due to an increase in child obesity and inactivity.

Diabetes is often initially managed by increasing exercise and dietary modification. As the condition progresses, medications may be needed. Unlike type I diabetes, there is very little tendency toward ketoacidosis though it is not unknown. One effect that can occur is nonketotic hyperglycemia. Long term complications from high blood sugar include an increased risk of heart attacks, strokes, amputation, and kidney failure.

There are many factors which can potentially give rise to or exacerbate type II diabetes. These include obesity, hypertension, elevated cholesterol (combined hyperlipidemia), and with the condition often termed metabolic syndrome (it is also known as Syndrome X, Reavan's syndrome, or CHAOS). Other causes include acromegaly, Cushing's syndrome, thyrotoxicosis, pheochromocytoma, chronic pancreatitis, cancer and drugs. Additional factors found to increase the risk of type II diabetes include aging, high-fat diets and a less active lifestyle. There is also a strong inheritable genetic connection in type II diabetes.

There are an estimated 23.6 million people in the United States (7.8% of the population) with diabetes with 17.9 million being diagnosed, 90% of whom are type II. With prevalence rates doubling between 1990 and 2005, CDC has characterized the increase as an epidemic. Traditionally considered a disease of adults, type II diabetes is increasingly diagnosed in children in parallel to rising obesity rates due to alterations in dietary patterns as well as in life styles during childhood. About 90-95% of all North American cases of diabetes are type II, and about 20% of the population over the age of 65 has diabetes mellitus type II. The fraction of type II diabetics in other parts of the world varies substantially, almost certainly for environmental and lifestyle reasons, though these are not known in detail. Diabetes affects over 150 million people worldwide and this number is expected to double by 2025.

There are several drugs available for type II diabetics, which fall into several classes and are not equivalent, nor can they be simply substituted one for another. All are prescription drugs. One of the most widely used drugs presently used for type II diabetes is the biguanide metformin. This drug works primarily by reducing liver release of blood glucose from glycogen stores and secondarily by provoking some increase in cellular uptake of glucose in body tissues.

As shown by Examples 5-7, the DFO-metal complexes of the invention, specifically, the Zn-DFO and Ga-DFO complexes and combinations thereof, clearly exhibit beneficial effects as demonstrated in different parameters examined in the diabetes type II model animals. Therefore, according to certain embodiments, the methods of the invention are suitable for preventing, treating, ameliorating or inhibiting diabetes type II. It is appreciated that the method of the invention leads to at least one of reduction in lens ferritin concentration, reduction in diabetes-induced cataract formation, reduction of blood glucose levels, reduction of blood level of 2,3-DHBA and catechols in a subject suffering of diabetes type II following administration of the Zn-DFO and Ga-DFO complexes of the invention.

It should be therefore noted that in particular embodiments, treatment of a subject suffering from diabetes type II with the metal-DFO complexes of the invention inhibits the increase in blood glucose level (above normal) by at least about 5% to about 99.9%, specifically, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or at least about 95%, most preferably about 98%, as demonstrated in Example 6.

Furthermore, in other embodiments, treatment of a subject suffering from diabetes type II with the metal-DFO complexes of the invention inhibits the increase in blood glucose level after glucose tolerance test, i.e., the three hours response to a 200 mg glucose dose per 100 g body weight, given orally, by at least about 5% to about 99.9%, more specifically, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 95, 97, 98, 99, and 100%. More specifically, the metal-DFO complexes of the invention inhibit the increase in blood glucose level after glucose tolerance by at least about 75%, at least about 76%, at least about 77%, specifically, about 78%, as illustrated by Example 7, FIG. 10A. In other embodiments the metal-DFO complexes of the invention inhibit the increase in blood glucose level after glucose tolerance by at least about 80% to 95%. More specifically, 80, 81, 82, 83, 84, 85, 86, 87, 88, 89, 90, 91, 92, 93, 94, and 95%, as illustrated by Example 6, FIG. 8.

In other embodiments, treatment of a subject suffering from insulin resistance, prior to the development of a fully blown diabetes type II, with the metal-DFO complexes of the invention inhibits the increase in blood glucose level, under normal nutrition, albeit the increase in body weight, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, most preferably, about 80%, as illustrated by Example 5—Table 4.

It should be further appreciated that the methods, kits and combined complexes of the invention may be applicable for treating diabetes-related conditions. It is understood that the interchangeably used terms "associated" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology. Such conditions may include for example, eye related complications (cataract, glaucoma, retinopathy), neuropathy, nephropathy, cardiomyopathy, stroke, hyper tension, peripheral arterial disease and sores. In accordance with the present invention the undesired side effect treated or prevented is preferably an undesired side effect related to the eye and/or vision such as cataract.

More specifically, one such diabetes-induced tissue damage prevented by the treatment of a subject suffering from diabetes type II with the metal-DFO complexes and specific combinations of the invention, is contemplated in specific embodiments, wherein the treatment decreases the probability of the subject to develop diabetes-induced cataract by at least about 5% to about 99.9%, specifically, at least about 5% to about 10%, at least about 10% to about 15%, at least about 15% to about 20%, at least about 20% to about 25%, at least about 25% to about 30%, at least about 35% to about 40%, at least about 40% to about 45%, at least about 45% to about 50%, at least about 50% to about 55%, at least about 55% to about 60%, at least about 65% to about 70%, at least about 75% to about 80%, at least about 80% to about 85%, at least about 85% to about 90%, at least about 90% to about 95%, at least about 95% to about 99%, preferably about 67% to about 83%, as illustrated by Example 6.

According to some embodiments, other indicators of tissue damage improve when treated with the metal-DFO complexes and combinations thereof of the invention, are demonstrated in Example 7. Such parameters include, among others, a decrease or increased degradation of tissue proteins comprising thioredoxin reductase, thioredoxin and actin, a decrease in tissue enzymatic activities, such as Msr activity, and an increase in tissue concentration of specific proteins, such as ferritin.

Thus, in specific embodiments, treatment of a subject suffering from diabetes type II with the metal-DFO complexes of the invention inhibits a diabetes-induced decrease in tissue thioredoxin reductase by at least about 5% to about 99.9%, specifically, at least about 5% to about 10%, at least about 10% to about 15%, at least about 15% to about 20%, at least about 20% to about 25%, at least about 25% to about 30%, at least about 35% to about 40%, at least about 40% to about 45%, at least about 45% to about 50%, at least about 50% to about 55%, at least about 55% to about 60%, at least about 65% to about 70%, at least about 75% to about 80%, at least about 80% to about 85%, at least about 85% to about 90%, at least about 90% to about 95%, at least about 95% to about 99.9%, preferably about 75% to 80%, most preferably about 75% to 77%, as demonstrated by Example 7, FIG. 14A.

In alternative embodiments, treatment of a subject suffering from diabetes type II with the metal-DFO complexes of the invention inhibits a diabetes-induced decrease in tissue thioredoxin by at least about 5% to about 99.9%, specifically, at least about 5% to about 10%, at least about 10% to about 15%, at least about 15% to about 20%, at least about 20% to about 25%, at least about 25% to about 30%, at least about 35% to about 40%, at least about 40% to about 45%, at least about 45% to about 50%, at least about 50% to about 55%, at least about 55% to about 60%, at least about 65% to about 70%, at least about 75% to about 80%, at least about 80% to about 85%, at least about 85% to about 90%, at least about 90% to about 95%, at least about 95% to about 99.9%, preferably about 95% to 99.9%, most preferably about 98% to 99.9%, as shown by Example 7, FIG. 14B.

Figure 11:
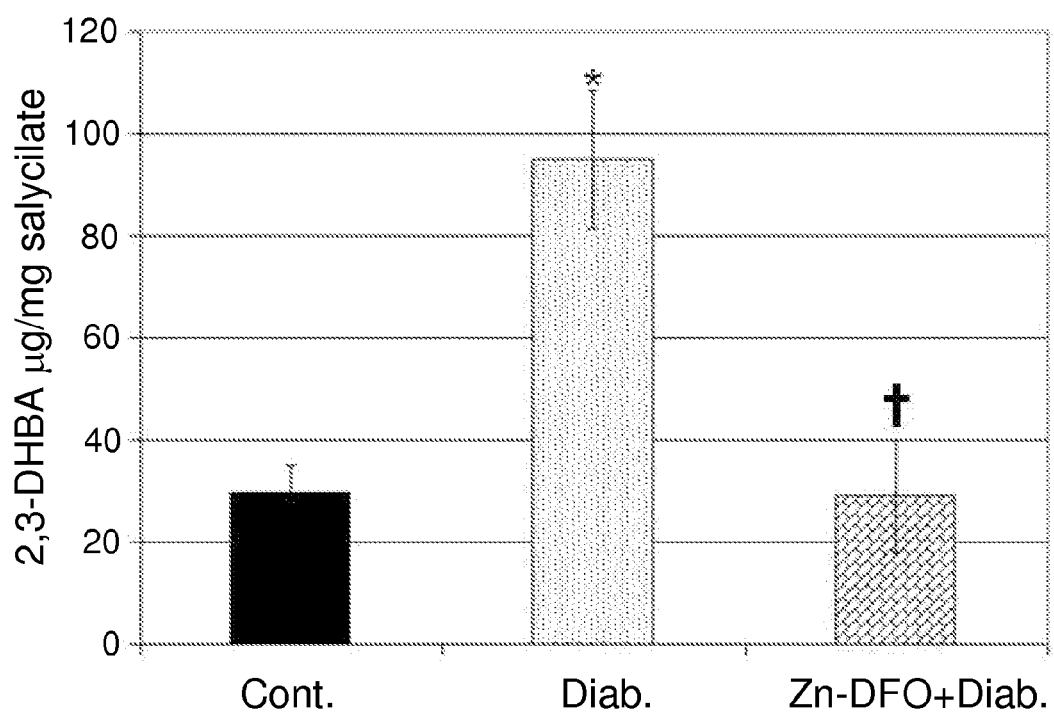

In some embodiments, treatment of a subject suffering from diabetes type II with the metal-DFO complexes of the invention inhibits a diabetes-induced increase in the conversion of salycilate to its free radical metabolites, as indicated by blood 2,3-DHBA by about 5% to about 99.9%, specifically, at least about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%, preferably about 95% to about 9.9%, most preferably about 97% to about 99.9%, as demonstrated by Example 7 (FIG. 11).

In other embodiments, treatment of a subject suffering from diabetes type II with the metal-DFO complexes of the invention inhibits a diabetes-induced decrease in tissue methionine-sulfoxide reductase (Msr) activity by about 5% to about 99.9%, specifically, at least about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%, preferably about 90% to about 95%, most preferably about 91% to about 93%, as seen in Example 7, FIG. 15B.

Some embodiments of the invention contemplate a treatment of a subject suffering from diabetes type II with the metal-DFO complexes of the invention, wherein the treatment results in the inhibition of diabetes-induced increase in tissue ferritin by about 5% to about 99.9%, specifically, at least about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%, preferably about 75% to about 80%, most preferably about 76% to about 78%, as illustrated by Example 7, FIG. 16.

The methods of treatment and uses of the invention may also be utilized for the benefit of subjects suffering from diabetes-related or associated diseases or disorders, comprising hyperinsulinaemia, dyslipidaemia, hypercholesterolemia, impaired glucose tolerance, hypertension, cardiovascular disease, diabetic cardiomyopathy, diabetic cardiac dysrhytmia, atherosclerosis, diabetic nephropathy, glomerulonephritis, glomerular sclerosis, nephrotic syndrome, hypertensive nephrosclerosis, end stage renal disease, microalbuminuria and albuminuria.

Hyperinsulinemia, or hyperinsulinaemia, as used herein, is a condition in which there are excess levels of circulating insulin in the blood. Also known as pre-diabetes, insulin resistance, and syndrome X, it is commonly associated with PCOS (Polycystic Ovarian Syndrome) in females. Hyperinsulinemia is often mistaken for diabetes or hypoglycaemia, both of which are separate conditions. Hyperinsulinemia can develop into diabetes if unmonitored and untreated, and may remain present when diabetes occurs. It is not caused by diabetes, as is commonly believed. Hyperinsulinemia may cause hypoglycaemia in some patients.

Dyslipidemia as used herein is a disruption in the amount of lipids in the blood. In societies of developed countries, most dyslipidemias are hyperlipidemias; that is, an elevation of lipids in the blood, often due to diet and lifestyle. The prolonged elevation of insulin levels can lead to dyslipidemia. Increased levels of O-GlcNAc transferase (OGT) are known to cause dyslipidaemia.

Hypercholesterolemia in accordance with the invention is the presence of high levels of cholesterol in the blood. It is not a disease but a metabolic derangement that can be secondary to many diseases and can contribute to many forms of disease, most notably cardiovascular disease. It is closely related to the terms "hyperlipidemia" (elevated levels of lipids) and "hyperlipoproteinemia" (elevated levels of lipoproteins). Elevated cholesterol in the blood is due to abnormalities in the levels of lipoproteins, the particles that carry cholesterol in the bloodstream. This may be related to diet, genetic factors (such as LDL receptor mutations in familial hypercholesterolemia) and the presence of other diseases such as diabetes and an underactive thyroid. The type of hypercholesterolemia depends on which type of particle (such as low density lipoprotein) is present in excess.

Impaired glucose tolerance (IGT) is a pre-diabetic state of dysglycemia that is associated with insulin resistance and increased risk of cardiovascular pathology. IGT may precede type II diabetes mellitus by many years.

Hypertension (HTN) or high blood pressure as used herein is a chronic medical condition in which the blood pressure in the arteries is elevated. It is the opposite of hypotension. It is classified as either primary (essential) or secondary. About 90-95% of cases are termed "primary hypertension", which refers to high blood pressure for which no medical cause can be found. The remaining 5-10% of cases (Secondary hypertension) are caused by other conditions that affect the kidneys, arteries, heart, or endocrine system. Persistent hypertension is one of the risk factors for strokes, heart attacks, heart failure and arterial aneurysm, and is a leading cause of chronic kidney failure.

Cardiomyopathy, as used herein is deterioration of myocardium functioning e.g. a clinical or sub-clinical condition diagnosed when ventricular dysfunction develops in patients with diabetes in the absence of coronary atherosclerosis and hypertension. It is characterized functionally by ventricular dilation, myocyte hypertrophy, interstitial fibrosis, and decreased or preserved systolic function in the presence of a diastolic dysfunction.

Atherosclerosis (also known as arteriosclerotic vascular disease or ASVD) is a condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

Diabetic nephropathy (nephropatia diabetica), also known as Kimmelstiel-Wilson syndrome, or nodular diabetic glomerulosclerosis and intercapillary glomerulonephritis, is a progressive kidney disease caused by angiopathy of capillaries in the kidney glomeruli. It is characterized by nephrotic syndrome and diffuse glomerulosclerosis. It is due to longstanding diabetes mellitus, and is a prime indication for dialysis in many Western countries.

Glomerulonephritis, also known as glomerular nephritis (GN), is a renal disease characterized by inflammation of the glomeruli, or small blood vessels in the kidneys. It may present with isolated hematuria and/or proteinuria (blood and/or protein presence in the urine); or as a nephrotic syndrome, a nephritic syndrome, acute renal failure, or chronic renal failure. They are categorized into several different pathological patterns, which are broadly grouped into non-proliferative or proliferative types. Primary causes are ones which are intrinsic to the kidney, whilst secondary causes are associated with certain infections (bacterial, viral or parasitic pathogens), drugs, systemic disorders (SLE, vasculitis) or diabetes.

Glomerular sclerosis refers to a hardening of the glomerulus in the kidney. It is a general term to describe scarring of the kidney glomeruli. Proteinuria (large amounts of protein in urine) is one of the signs of glomerulosclerosis. Diabetes is a frequent cause of glomerular sclerosis.

Nephrotic syndrome is a nonspecific disorder in which the kidneys are damaged, causing them to leak large amounts of protein (proteinuria at least 3.5 grams per day per 1.73 $m^2$ body surface area) from the blood into the urine.

Kidneys affected by nephrotic syndrome have small pores in the podocytes, large enough to permit proteinuria (and subsequently hypoalbuminemia, because some of the protein albumin has gone from the blood to the urine) but not large enough to allow cells through (hence no hematuria). By contrast, in nephritic syndrome, RBCs pass through the pores, causing hematuria. Diabetes is often an underlying cause of nephrotic syndrome.

Hypertensive nephropathy, or hypertensive nephrosclerosis, or hypertensive renal disease, is a medical condition referring to damage to the kidney due to chronic high blood pressure. In the kidneys, as a result of benign arterial hypertension, hyaline (pink, amorphous, homogeneous material) accumulates in the wall of small arteries and arterioles, producing the thickening of their walls and the narrowing of the lumina—hyaline arteriolosclerosis. Consequent ischemia will produce tubular atrophy, interstitial fibrosis, glomerular alterations (smaller glomeruli with different degrees of hyalinization—from mild to sclerosis of glomeruli) and periglomerular fibrosis. In advanced stages, renal failure will occur. Functional nephrons have dilated tubules, often with hyaline casts in the lumens. Additional complications often associated with hypertensive nephropathy include glomerular damage resulting in proteinuria and hematuria.

End-stage renal disease is an advanced stage of chronic kidney disease (CKD), also known as chronic renal disease. CKD manifests as a progressive loss in renal function over a period of months or years. The symptoms of worsening kidney function are unspecific, and might include feeling generally unwell and experiencing a reduced appetite. Recent professional guidelines classify the severity of chronic kidney disease in five stages, with stage 1 being the mildest and usually causing few symptoms and stage 5 being a severe illness with poor life expectancy if untreated. Stage 5 CKD is also called established chronic kidney disease and is synonymous with the now outdated terms end-stage renal disease (ESRD), chronic kidney failure (CKF) or chronic renal failure (CRF).

As clearly shown by the Examples, the metal complexes and combinations of the invention are effective in reducing cataract. Therefore, according to another specific embodiment, the invention provides methods, uses combined compositions and kits for preventing, treating, ameliorating or inhibiting cataract, including cataract that is not related to diabetes. A cataract as used herein is a clouding that develops in the crystalline lens of the eye or in its envelope, varying in degree from slight to complete opacity and obstructing the passage of light. Early in the development of age-related cataract the power of the lens may be increased, causing near-sightedness (myopia), and the gradual yellowing and opacification of the lens may reduce the perception of blue colors. Cataracts typically progress slowly to cause vision loss and are potentially blinding if untreated. The condition usually affects both the eyes, but almost always one eye is affected earlier than the other.

A senile cataract, occurring in the elderly, is characterized by an initial opacity in the lens, subsequent swelling of the lens and final shrinkage with complete loss of transparency. Moreover, with time the cataract cortex liquefies to form a milky white fluid in a Morgagnian cataract, which can cause severe inflammation if the lens capsule ruptures and leaks. Untreated, the cataract can cause phacomorphic glaucoma.

Age-related cataract is responsible for 48% of world blindness, which represents about 18 million people, according to the World Health Organization (WHO).

Cataracts develop for a variety of reasons, including long-term exposure to ultraviolet light, exposure to radiation, secondary effects of diseases such as diabetes, hypertension and advanced age, or trauma (possibly much earlier); they are usually a result of denaturation of lens protein. Genetic factors are often a cause of congenital cataracts and positive family history may also play a role in predisposing someone to cataracts at an earlier age, a phenomenon of "anticipation" in pre-senile cataracts. Cataracts may be partial or complete, stationary or progressive, hard or soft. Some drugs can induce cataract development, such as corticosteroids and Seroquel. There are various types of cataracts, e.g. nuclear, cortical, mature, and hyper-mature. Cataracts are also classified by their location, e.g. posterior (classically due to steroid use) and anterior (common (senile) cataract related to aging). It should be therefore appreciated that the metal-DFO complexes of the invention may be applicable for all cataract types indicated herein above.

It should be noted that in certain embodiments the methods, compositions, combined compositions and kits of the invention may be applicable in treating any inflammatory condition in the eyes provided that such disorder is not induced following exposure to nitrogen and other mustard gases, as well as other warfare agent, e.g. Sarin.

According to one embodiment, the method of the invention may be particularly applicable for treating and ameliorating immune inflammation and immune-related disorders, preferably at least one of psoriasis, asthma and diabetes.

It should be noted that an "Immune-related disorder" is a condition that is associated with the immune system of a subject, either through activation or inhibition of the immune system, or that can be treated, prevented or diagnosed by targeting a certain component of the immune response in a subject, such as the adaptive or innate immune response. Such disorder may be any one of an inflammatory disease or an autoimmune disease.

According to one specific embodiment, the method of the invention may be specifically suitable for treating an inflammatory disease or an inflammatory-associated condition.

The terms "inflammatory disease" or "inflammatory-associated condition" refers to any disease or pathologically condition which can benefit from the reduction of at least one inflammatory parameter, for example, induction of an inflammatory cytokine such as IFN-gamma and IL-2. The condition may be caused (primarily) from inflammation, or inflammation may be one of the manifestations of the diseases caused by another physiological cause.

Examples of other immune-related disorders that may be treated by the methods, combined compositions and kits of the invention include, but are not limited to, Ulcerative Colitis, Crohn's Disease, Irritable Bowel Disease (IBD), Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), IgA Nephropathy, Uveitis, Vasculitis, Lichen Planus, and Vitiligo. The DFO-metal complexes described herein can be administered to a subject to treat or prevent disorders associated with an abnormal or unwanted immune response associated the above diseases.

It is understood that the interchangeably used terms "associated", "linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology.

The method of the invention involves administration of therapeutically effective amount of the DFO-metal complexes of the invention. The term "effective amount" as used herein is that determined by such considerations as are known to the man of skill in the art. The amount must be sufficient to prevent or ameliorate tissue damage caused by immune-, inflammation- and autoimmune related disorders treated, specifically, psoriasis, asthma and diabetes. Dosing is dependent on the severity of the symptoms and on the responsiveness of the subject to the active drug. Medically trained professionals can easily determine the optimum dosage, dosing methodology and repetition rates. In any case, the attending physician, taking into consideration the age, sex, weight and state of the disease of the subject to be treated, will determine the dose.

More specifically, the compositions containing the metal-DFO complexes of the present invention, or any combination, mixture or cocktail thereof can be administered for prophylactic and/or therapeutic treatments. In therapeutic application, compositions are administered to a patient already affected by an immune-, inflammation or immune-related disorder (e.g., asthma, diabetes and psoriasis) in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg/Kg, specifically, about 0.01 to about 100, 90, 80, 70, 60, 50, 40, 30, 20 and 10 mg/Kg, more specifically, about 20 mg/Kg of the metal-DFO complexes of the invention per dose, with dosages of from 0.1 to 50, more specifically, 50, 40, 30, 20, 10, 9.5, 9, 8.5, 8, 7.5, 7, 6.5, 6, 5.5, 5, 4.5, 4, 3.5, 3, 2.5, 2, 1.5 and 1 mg per Kg of body weight. Specifically, about 0.01 to about 3.5 mg per Kg of body weight being more commonly used. Single or multiple administrations on a daily, weekly or monthly schedule can be carried out with dose levels and pattern being selected by the treating physician. More specific embodiments relate to the use of typically 2-3 doses per week, containing 0.25 mg per Kg body weight, but not more than a daily dose of 2.5 mg/Kg body weight.

The invention further provides a method for preventing or reducing the risk of developing an immune-related disorder such as skin-inflammatory disorders, respiratory disorders and diabetes-associated disorders, preferably psoriasis, asthma and diabetes. Such method comprises the administration of a prophylactically effective amount of the metal complex, or combination of more than one metal complex according to the invention, or pharmaceutical compositions thereof, to a person at risk of developing an immune-related disorder such as skin-inflammatory disorders, respiratory disorders and diabetes-associated disorders, preferably psoriasis, asthma and diabetes. The term "prophylaxis" refers to prevention or reduction the risk of occurrence of the biological or medical event that is sought to be prevented in a tissue, a system, animal or human by a researcher, veterinarian, medical doctor or other clinician, and the term "prophylactically effective amount" is intended to mean that amount of a pharmaceutical composition that will achieve this goal.

The term "prophylactically effective amount" is intended to mean that amount of a pharmaceutical combined composition that will prevent or reduce the risk of occurrence or recurrence of the biological or medical event that is sought to be prevented in a tissue, a system, animal or human by a researcher, veterinarian, medical doctor or other clinician. In prophylactic applications, compositions containing the metal-complexes of the invention or any combination, mixture or cocktail thereof are administered to a patient who is at risk of developing the disease state to enhance the patient's resistance. Such an amount is defined to be a "prophylactically effective dose". In this use, the precise amounts again depend upon the patient's state of health and general level of immunity, but generally range from 0.1 to 100 mg per dose, especially 0.1 to 10 mg per Kg of body weight per dose, specifically, 0.1, 0.2, 0.3, 0.4, 0.5, 0.6, 0.7, 0.8, 0.9, 1, 2, 3, 4, 5, 6, 7, 8, 9, and 10 mg per Kg of body weight per dose.

Additionally, the administration of the metal complexes of the invention, or pharmaceutical compositions thereof, according to the invention, may be periodic, for example, the periodic administration may be effected twice daily, three time daily, or at least one daily for at least about three days to three months. The advantages of lower doses are evident to those of skill in the art. These include, inter alia, a lower risk of side effects, especially in long-term use, and a lower risk of the patients becoming desensitized to the treatment.

In another embodiment, treatment using the metal complexes of the invention, or pharmaceutical compositions thereof, may be effected following at least 1, 2, 3, 4, 5, 6, 7, 8, 9, 10, 14, 30, 60, 90 days of treatment, and proceeding on to treatment for life.

It should be noted that the treatment of different conditions may indicate the use of different doses or different time periods; these will be evident to the skilled medical practitioner.

It should be further noted that for the method of treatment and prevention provided in the present invention, said therapeutic effective amount, or dosage, is dependent on severity of the disease state to be treated and the responsiveness of the patient, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the combined composition of the invention in bodily fluids or tissues. Following successful treatment, it may be desirable to have the patient undergo maintenance therapy to prevent the recurrence of the disease state, wherein the combined composition of the invention is administered in maintenance doses, once or more daily.

As used herein, "disease", "disorder", "condition" and the like, as they relate to a subject's health, are used interchangeably and have meanings ascribed to each and all of such terms.

The present invention relates to the treatment of subjects, or patients, in need thereof. By "patient" or "subject in need" it is meant any organism who may be affected by the above-mentioned conditions, and to whom the treatment and diagnosis methods herein described is desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal. More specifically, the composition of the invention is intended for mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection, drinking water, feed, spraying, oral gavage and directly into the digestive tract of subjects in need thereof. It should be further noted that particularly in case of human subject, administering of the drug combination to the patient includes both self-administration and administration to the patient by another person.

The term "treatment or prevention" refers to the complete range of therapeutically positive effects of administrating to a subject including inhibition, reduction of, alleviation of, and relief from, psoriasis, asthma or diabetes and illness, psoriasis, asthma or diabetes symptoms or undesired side effects or psoriasis, asthma or diabetes related disorders. More specifically, treatment or 'prevention includes the prevention or postponement of development of the disease, prevention or postponement of development of symptoms and/or a reduction in the severity of such symptoms that will or are expected to develop. These further include ameliorating existing symptoms, preventing—additional symptoms and ameliorating or preventing the underlying metabolic causes of symptoms. It should be appreciated that the terms "inhibition", "moderation", "reduction" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

In a second aspect, the invention contemplates the use of a therapeutically effective amount of at least one desferrioxamine-metal complex (DFO-metal complex), or any combination thereof in the preparation of a composition for the prophylaxis, treatment, amelioration or inhibition of an immune related disorder.

More than a single metal type can be used according to the invention. In fact, in some embodiments of the use of the invention, the metal is selected from any one of zinc, gallium, manganese, indium, silver, gold, cobalt and lanthanides specifically, europium (Eu) and/or their combinations, preferably zinc and gallium.

In more preferable embodiments of the use of the invention, desferrioxamine-metal complex is at least one of zinc-desferrioxamine complex (Zn-DFO), gallium-desferrioxamine complex (Ga-DFO), or any combination thereof, and in further embodiments of the use of the invention, the composition further comprises at least one additional therapeutic agent.

It is noted that in various embodiments the invention provides the use of DFO-metal complexes and specifically, DFO-Zn, DFO-Ga and any combinations thereof for preventing, treating, ameliorating or inhibiting an immune-related disorder, specifically, an inflammatory disease and an autoimmune disease.

Some specific embodiments contemplate the use of the invention, wherein the inflammatory disease may be any one of a chronic or acute inflammatory-related skin pathologic condition, a respiratory disease, and wherein said inflammatory systemic disorder or autoimmune disease is diabetes or any diabetes-related condition.

In more specific embodiments, the use of the invention is contemplated, wherein the chronic or acute inflammatory-related skin pathologic condition is psoriasis.

In other specific embodiments, the use of the invention is contemplated, wherein the respiratory diseases is asthma.

In yet other specific embodiments, the use of the invention is contemplated, wherein the disorder is any one of diabetes type II, diabetes type I or any diabetes-related condition.

The invention further provides at least one desferrioxamine-metal complex (DFO-metal complex), or any combination thereof or any pharmaceutical composition comprising the same for use in preventing, treating, ameliorating or inhibiting an immune-related disorder, specifically, any one of psoriasis, asthma and diabetes.

In a third aspect, the invention is directed to a composition comprising a combination of a therapeutically effective amount of at least two desferrioxamine-metal complexes (DFO-metal complexes), the composition optionally further comprises at least one pharmaceutically acceptable carrier, diluent, excipient and/or additive.

In some embodiments, the metal of the composition of the invention may be selected from any one of zinc, gallium, manganese, indium, silver, gold, cobalt and lanthanides specifically, europium (Eu) and any combination thereof.

In other specific embodiments, the composition of the invention comprises a combination of zinc-desferrioxamine complex (Zn-DFO) and gallium-desferrioxamine complex (Ga-DFO).

Specific embodiments describe compositions of the invention, wherein the zinc-desferrioxamine complex (Zn-DFO) and said gallium-desferrioxamine complex (Ga-DFO) are contained at a quantitative ratio of between 1:0.01 to 1:100.

It is understood that two or more metal-complexes according to the invention may be combined for treatment of immune-related respiratory diseases. According to one embodiment, use of a combination of two or more metal-DFO complexes according to the invention may comprise at least Zn-DFO combined with Ga-DFO at any quantitative ratio of between about 100:1 to 1:100, respectively. It should be appreciated that any quantitative ratio of the combined compounds may be used. As a non-limiting example, a quantitative ratio used between any of the compounds may be: 100:1, 90:1, 80:1, 70:1, 60:1, 50:1, 40:1, 30:1, 20:1, 10:1, 9:1, 8:1, 7:1, 6:1, 5:1, 4:1, 3:, 1 2:, 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100. Typically the ratio of the Zn-DFO: Ga-DFO may range from 20:1-1:20; specifically, a ratio of 4:1 to 1:4, more specifically a ratio of either 1:1 or 3:1, respectively, as shown in Example 2, and preferably a ratio of 1:1. In yet another embodiment, specific DFO-metal ratio used for the a combined composition of the invention be the invention may be 1:1, 3:1, 4:1 and 1:2 (Zn- to Ga-DFO ratio respectively). It should be further noted that where the combination of the invention comprises more than two complexes, the quantitative ratio used may be for example, 1:1:1, 1:2:3, 1:10:50, 1:20:100, 50:10, or 5:50: 12 etc.

Some embodiments contemplate the combined composition of the invention, wherein the composition comprises at least one additional desferrioxamine metal complex.

Other embodiments contemplate the combined composition of the invention, wherein the composition further comprises at least one additional therapeutic agent.

The invention thus provides a combined composition for preventing, treating, ameliorating or inhibiting an immune-related disorder. According to some embodiments, the above immune-related disorder is any one of an inflammatory disease and an autoimmune disease.

In some embodiments the pharmaceutical composition according to the invention is particularly effective in the treatment of any one of an inflammatory disease and an autoimmune disease, wherein these diseases are any one of a chronic or acute inflammatory-related skin pathologic condition, a respiratory disease, and wherein the autoimmune disease is diabetes or any diabetes related condition.

More specific embodiments consider the combined composition of the invention for preventing, treating, ameliorating or inhibiting a chronic or acute inflammatory-related skin pathologic condition, for example, psoriasis. Thus, in one particular embodiment, the combined composition of the invention is used for treating psoriasis.

It should not be overlooked that the composition of the invention, particularly when used for treating inflammatory skin disorders such as psoriasis, may be an acceptable topically applied composition as will be described in more detail herein after. Alternatively, the administration may be systemic such as by sublingual, rectal, vaginal, buccal, parenteral, intravenous, intramuscular, subcutaneous modes transdermal, inrtaperitoneal or intranasal modes of administration. However, oral, transmucosal, intestinal or parenteral delivery, including intramuscular, subcutaneous and intramedullary injections as well as rectal, intrathecal, direct intraventricular, intravenous, intraocular injections or any other medically acceptable methods of administration can be considered as well.

Some embodiments consider the combined composition according to the invention, particularly for treating respiratory diseases such as asthma. According to one embodiment, such combined composition may be particularly adapted for pulmonary delivery by oral or nasal inhalation. More specifically, pulmonary delivery may require the use of liquid nebulizers, aerosol-based metered dose inhalers (MDI's), or dry powder dispersion devices. Alternatively, the administration may be systemic such as by sublingual, vaginal, buccal, parenteral, intravenous, intramuscular, subcutaneous modes transdermal, inrtaperitoneal or intranasal delivery, however, oral, transmucosal, intestinal or parenteral delivery, including intramuscular, subcutaneous and intramedullary injections as well as rectal, intrathecal, direct intraventricular, intravenous, intraocular injections or any other medically acceptable methods of administration can be considered as well.

According to some embodiments, the pharmaceutical combined composition of the invention is effective for the treatment of an autoimmune disorder, specifically, diabetes. More specifically, the combined compositions of the invention may be used for treating diabetes type II, diabetes type I or any diabetes related condition. According to such embodiment, the combined composition of the invention may be specifically adapted for transdermal, intraperitoneal or intranasal delivery, however, oral, transmucosal, intestinal or parenteral delivery, including intramuscular, subcutaneous and intramedullary injections as well as rectal, intrathecal, direct intraventricular, intravenous, or intraocular injections are considered as well or any other medically acceptable methods of administration can be considered as well.

Single or multiple administrations of the combined compositions of the invention are administered depending on the dosage and frequency as required and tolerated by the patient. In any event, the composition should provide a sufficient quantity of the metal-DFO complexes of the invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the metal-DFO complexes of the present invention can be made as implants, oily injections, or as particulate systems or any other medically acceptable methods.

Particulate systems include microspheres, microparticles, microcapsules, nanocapsules, nanospheres, and nanoparticles. Microcapsules contain the therapeutic DFO-metal complexes, specifically, the Zn-DFO, Ga-DFO or any combinations thereof as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly.

Polymers can be used for ion-controlled release of the metal-DFO complexes of the invention or any combined compositions thereof. Various degradable and nondegradable polymeric matrices for use in controlled drug delivery are known in the art.

In yet another embodiment, liposomes are used for controlled release as well as drug targeting of the lipid-capsulated drug.

"Liposome" is to be understood as a vesicle, the wall of which is formed from one or more bilayers of amphiphilic molecules enclosing an internal aqueous cavity, said amphiphilic molecules comprising a polar head and hydrophobic residues which are generally alkyl chains or "hydrophobic tails". The bilayer(s) preferably comprises (comprise) phospholipids. Examples of phospholipids include phosphatidylcholine (PC) and derivatives thereof: egg phosphatidylcholine (Egg-PC), dimyristoyl-phosphatidyl-choline (DMPC), dipalmitoylphosphatidylcholine (DPPC), dioleoylphosphatidylcholine (DOPC), dilauroylphosphatidylcholine (DLPC), distearoylphosphatidylcholine (DSPC), diarachidoylphosphatidylcholine (DAPC) and dilinoleoylphosphatidyl-choline (DLPC).

Other phospholipids including, for example, a glycerol group which is bound to two chains of fatty acids and the polar head of which is different from phosphatidylcholine may also be used according to the process of the invention. Other amphiphilic molecules may also form part of the composition of the liposome bilayers (cholesterol, lipids with a polar head modified by a hydrophilic group, cationic lipids, fluorescent lipids, etc.). The liposomes are preferably predominantly composed of phospholipids. The liposomes may be prepared in accordance with conventional techniques including ultrasound irradiation, phase inversion, extrusion, dialysis, resin absorption or gel filtration of mixed lipid-detergent micelles and the freeze-thaw method. For example, the liposomes may be prepared by hydrating a phospholipid film followed by an extrusion process which is sequenced in order to size the vesicles.

As indicated above, certain embodiments of the invention concern combined compositions comprising combinations of the DFO-metal complexes of the invention for use in preventing, treating, ameliorating or inhibiting immune-related disorders such as inflammatory skin conditions, specifically, psoriasis. It should be noted that DFO-metal complexes, preferably Zn-DFO, Ga-DFO and any combination thereof may be administered to a subject in need thereof, optionally in the form of a pharmaceutical composition, which may comprise the active compound in free form and be administered directly to the subject to be treated. Alternatively, depending on the size of the active molecule, it may be desirable to conjugate it to a carrier prior to administration. Therapeutic formulations may be administered in any conventional dosage formulation. Formulations typically comprise at least one active ingredient, as defined above, together with one or more acceptable carriers thereof.

The term "effective amount" as used herein is that determined by such considerations as are known to the man of skill in the art. The amount must be sufficient to prevent or ameliorate tissue damage caused by immune-, inflammation- and autoimmune related disorders treated, specifically, psoriasis, asthma and diabetes. Dosing is dependent on the severity of the symptoms and on the responsiveness of the subject to the active drug. Medically trained professionals can easily determine the optimum dosage, dosing methodology and repetition rates. In any case, the attending physician, taking into consideration the age, sex, weight and state of the disease of the subject to be treated, will determine the dose.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intraperitoneal (i.p.), intravenous (i.v.) and intradermal) administration or any other medically acceptable methods. In preferred embodiments, the formulations are suitable for oral, nasal, or intraperitoneal (i.p.) administration.

The nature, availability and sources, and the administration of all such complexes including the effective amounts necessary to produce desirable effects in a subject are well known in the art and need not be further described herein. The preparation of pharmaceutical compositions is well known to the skilled man of the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Specific embodiments contemplate skin inflammatory conditions, specifically, psoriasis treatment by topical administration of the affected skin areas of an ointment, cream, suspensions, paste, lotions, powders, solutions, oils, encapsulated gel, liposomes containing the complexes, any nanoparticles containing the complexes of the invention, or sprayable aerosol or vapors containing a combination of these complexes. Conventional pharmaceutical carriers, aqueous, powder or oily bases, thickeners and the like may be necessary or desirable. The term "topically applied" or "topically administered" means that the ointment, cream, emollient, balm, lotion, solution, salve, unguent, or any other pharmaceutical form is applied to some or all of that portion of the skin of the patient skin that is, or has been, affected by, or shows, or has shown, one or more symptoms of psoriasis.

It should be noted that since a topical application of the DFO-metal complexes and combinations by the method of the invention particularly in treating skin inflammatory disorders, any transdermal delivery may be used. As used herein, the term "transdermal" refers to delivery, administration or application of a drug by means of direct contact with tissue, such as skin or mucosa. Such delivery, administration or application is also known as percutaneous, dermal, transmucosal and buccal.

Therapeutic compositions for transdermal administration, or "dermal compositions" are compositions which contain one or more drugs solubilized therein, specifically, any of the DFO-metal complexes or combinations thereof according to the invention. The composition is applied to a dermal area, for dermal administration or topical application of the drugs. Such a dermal composition may comprise a polymer matrix with the one or more drugs contained therein. The polymer matrix may be a pressure-sensitive adhesive for direct attachment to a user's (e.g., a patient's) skin. Alternatively, the polymer matrix may be non-adhesive and may be provided with separate adhesion means (such as a separate adhesive layer) for adhering the composition to the user's skin.

As used herein, the term "solubilized" is intended to mean that in the dermal composition there is an intimate dispersion or dissolution of the active agent (e.g., drug) at the crystalline, molecular or ionic level. As such, the solubilized active agent is considered herein to be in "non-crystallized" form when in the compositions of the present invention.

As used herein, "matrix" is defined as a polymer composition which incorporates a therapeutically effective amount of the drug therein. The matrix may be monolithic and comprise a pressure-sensitive adhesive, or it may use separate attachment means for adhering or holding to the user's skin, such as a separate adhesive layer. A dermal drug delivery system comprising a matrix may optionally include additional drug supply means for continuously replenishing the drug supply in the matrix. "Monolithic" is defined as a device comprising a matrix composition which is adhesive, e.g., pressure-sensitive adhesive, bio-adhesive, or otherwise.

As used herein, a polymer is an "adhesive" if it has the properties of an adhesive per se, or if it functions as an adhesive by the addition of tackifiers, plasticizers, cross-linking agents or other additives.

In one embodiment, the transdermal systems contemplated for practicing the methods, kits and combined compositions described here are in the form of a flexible, finite system. The phrase "flexible, finite system" is intended to mean a substantially non-aqueous, solid form, capable of conforming to the surface with which it comes into contact, and which is capable of maintaining the contact in such solid form so as to facilitate topical application without adverse physiological response, and without being appreciably decomposed by aqueous contact during topical application to a patient. Many such devices are known in the art and commercially available, such as transdermal drug delivery patches. Examples of suitable flexible, finite systems include those in which the drug is solubilized directly in an adhesive matrix, such as a pressure-sensitive adhesive, that also serves as the means for attaching the system to the skin or mucosa of a patient.

The flexible finite systems also may include a drug impermeable backing layer or film on one side of the adhesive layer, and a release liner on the other side. When present, the backing layer protects the adhesive layer of the flexible finite system or transdermal patch from the environment and prevents loss of the drug and/or release of other adhesive layer components to the environment. When present, the release liner is removed from the system to expose the adhesive layer prior to topical application. Materials suitable for use as release liners and backing layers are well-known known in the art.

It should be noted that the term "skin" as used herein means the air-contacting part of the human body, to a depth of about 7 mm from the air interface; as such, it also includes the nails.

In preferred embodiments, the administration of the metal complexes of the invention for the treatment of skin disorders, specifically psoriasis, is by topical dressing. The term "dressing" means a covering for a wound or surgical site, typically composed of a cloth, fabric, synthetic membrane, gauze, or the like. It is usually a polymer-containing matrix covering an area of the skin. The dressing may or may not be in intimate contact with the skin. It can be, for example, a cloth or gauze, or it can be a polymer solution painted or sprayed on the skin, the polymer solidifying on the skin when the solvent dries off and/or when the polymer crosslinks. Dressings also include gels, typically cross-linked hydrogels, which are intended principally to cover and protect wounds, surgical sites, and the like.

In further preferred embodiments, the concentration of the active metal-DFO complex and any combinations thereof in an oil-based, preferably vaseline-based ointment may range from 0.05% w/v to 5% w/v, more preferably from 0.1% w/v to 1.0% w/v, specifically, 0.1, 0.2, 0.3, 0.4, 0.5, 0.6, 0.7, 0.8, 0.9 and 1.0% w/v, and particularly 0.1% w/v to 0.4% w/v, as shown in the Examples herein.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

For applications to the external tissues, for example the mouth and skin, the formulations are preferably applied as a topical ointment or cream. When formulated in an ointment, the active ingredient may be employed with either paraffin or a water-miscible ointment base. Alternatively, the active ingredient may be formulated in a cream with an oil-in-water cream base or a water-in-oil base.

For the treatment of skin injuries, the DFO-metal complex, preferably Zn-DFO, Ga-DFO, any combinations thereof, combined compositions or compositions thereof, may be applied as a cream, an ointment, a liquid, or even as sustained-release patches, in all of which said DFO-metal or said composition shall be a component thereof.

Pharmaceutical formulations adapted for transdermal administration may be presented as discrete patches intended to remain in intimate contact with the epidermis of the recipient for a prolonged period of time.

It should be noted that topical treatment of skin damages may be combined with systemic treatment, e.g. injection of the DFO-metal complex and combinations thereof. Injection may be intra-peritoneal, subcutaneous, intra-lesional, intra-osseous and other suitable modes of administration, preferably intra-peritoneal.

Generally, use of either systemic or topical treatments (i.p. injections and i.n. instillations as described or application of ointment containing 0.5% (w/v) of a combination of gallium DFO (0.1%) and zinc DFO (0.4%) in a fatty carrier) proved protective.

Pharmaceutical formulations adapted for topical administration in the mouth include lozenges, pastilles and mouth washes.

The administration of the metal-DFO complexes and combinations thereof according to the invention for the treatment, amelioration or prophylaxis of psoriasis may be any one of sublingual, buccal, rectal, vaginal, parenteral, intravenous, intramuscular, intraperitoneal, subcutaneous, intramedullary, transdermal, via oral or nasal inhalation, however, topical and transdermal applications are preferred. Metal-DFO complexes of the invention may be administered to a subject suffering from psoriasis at least once a year, more preferably, at least once every 6 months, more preferably, at least once every 3 months, more preferably, at least once every 2 months, more preferably, at least once every one month, more preferably, at least once every 2 weeks, more preferably, at least once every week, more preferably, at least twice every week, more preferably, at least once every other day, most preferably, at least twice every other day. According to one embodiment, the metal-DFO complexes of the invention may be administered twice daily, more specifically, once daily, once every other day, once every week, once every two weeks, once every month, for several days to several months. Typically, three times a week for a period of two weeks.

Certain embodiments of the invention concern combined compositions comprising combinations of the DFO-metal complexes of the invention for use in preventing, treating, ameliorating or inhibiting immune-related disorders such as inflammatory respiratory conditions, specifically, asthma. The metal-complexes of the invention thus may be applied in immune-related disorders, which disorders also comprise some respiratory disorders. With regards to respiratory disorders, the terms "amelioration" or "treatment" refers to any of the following: treatment of an existing disease which includes curing the disease; improving the condition of a diseases individual (alleviating disease manifestations); decreasing the number, duration or severity of acute diseases attacks (such as acute asthmatic or allergic attacks). The term "preventing" refers to preventing the occurrence or reoccurrence of the acute disease attacks (such as prevention of asthma attacks or allergic attacks or prevention of, re-growth of nasal polyps, after their removal). It should be emphasized that the method of the invention is also prophylactic, especially for the treatment of asthma, and includes the administration of the desferrioxamine-metal complex in order to prevent asthma attacks either on a regular basis or according to need.

Pulmonary administration is considered a preferred administration method for the treatment of respiratory disorders according to some embodiments.

The term "administration" when relating to treatment of respiratory disorders is preferably pulmonary delivery by oral inhalation, such as by using liquid nebulizers, aerosol-based metered dose inhalers (MDIs), or dry powder dispersion devices, or by intraperitoneal injection. Alternatively, the administration may be any one of sublingual, buccal, parenteral, intravenous, intramuscular, subcutaneous, intramedullary, or transdermal.

Specifically, asthma may be treated by pulmonary administration of the metal-complexes of the invention, e.g., by inhalation or insufflation of powders or aerosols, including by nebulizer; intratracheal, intranasal, epidermal and transdermal.

Furthermore, metal-DFO complexes of the invention may be administered to a subject suffering from respiratory disorders at least once every 2 months, more preferably, at least once every one month, more preferably, at least once every 2 weeks, more preferably, at least once every week, most preferably, at least twice or three times every week.

According to some embodiments, doses particularly suitable for treatment of human subjects suffering from asthma or other respiratory disorders may range between 0.001 mg/kg body weight to about 2.5 mg/kg body weight, more specifically, between 0.003 mg/kg body weight to about 1.0 mg/kg body weight, more specifically, between 0.006 mg/kg body weight to about 0.6 mg/kg body weight, more specifically, between 0.009 mg/kg body weight to about 0.5 mg/kg body weight, more specifically, between 0.012 mg/kg body weight to about 0.4 mg/kg body weight, more specifically, between 0.015 mg/kg body weight to about 0.3 mg/kg body weight, more specifically, between 0.018 mg/kg body weight to about 0.2 mg/kg body weight, most specifically, between 0.02 mg/kg body weight to about 0.2 mg/kg body weight.

In particular embodiments, the active metal-DFO complex of the invention is particularly effective when administered a subject suffering from asthma in a dose corresponding to about 0.03 to 10 mg/kg body weight of the treated subject, more specifically, about 0.03 to 10 mg/kg, more specifically, about 0.06 to 9 mg/kg, more specifically, about 0.09 to 8 mg/kg, more specifically, about 0.12 to 7 mg/kg, more specifically, about 0.15 to 6 mg/kg, more specifically, about 0.18 to 5 mg/kg, more specifically, about 0.21 to 4 mg/kg, more specifically, about 0.24 to 3 mg/kg, more specifically, about 0.27 to 2 mg/kg, most specifically, about 0.3 to 1 mg/kg body weight of the treated subject.

For administration by nasal inhalation, the active ingredients for use according to the present invention, which are the DFO-metal-complexes of the invention and combinations thereof, may conveniently be delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient. According to some embodiments, the DFO-metal complex according to the invention can be applied to a subject in need as nasal drops, ophthalmic gel, ophthalmic ointment, spray or patches.

As shown by the Examples, for the treatment of respiratory disorders, preferably asthma, pre-conditioning (initiating treatment shortly before potential exposure) may provide further benefit.

As indicated above, certain embodiments of the invention concern combined compositions comprising combinations of the DFO-metal complexes of the invention for use in preventing, treating, ameliorating or inhibiting immune-related disorders, specifically autoimmune disorders such as diabetes, specifically, diabetes type I, II, or any related disorders. The terms "treatment" or "prevention", in the context of diabetes, include the prevention or postponement of development of the disease, prevention or postponement of development of symptoms such as, for example, hyperglycemia or glucosuria and/or a reduction in the severity of such symptoms that will or are expected to develop. These further include ameliorating existing symptoms, preventing additional symptoms and ameliorating or preventing the underlying metabolic causes of symptoms.

Examples of undesired side effects and diabetes related disorders include: eye related complications (cataract, glaucoma, retinopathy), neuropathy, atherosclerosis, cardiomyopathy, cardiac dysrhythmia, nephropathy, stroke, hypertension, peripheral arterial disease and sores. In accordance with the present invention the undesired side effect treated or prevented is preferably an undesired side effect related to the eye and/or vision such as cataract.

A stroke (sometimes called a cerebrovascular accident (CVA)) is the rapidly developing loss of brain function(s) due to disturbance in the blood supply to the brain. This can be due to ischemia (lack of blood flow) caused by blockage (thrombosis, arterial embolism), or a hemorrhage (leakage of blood). A stroke is a medical emergency and can cause permanent neurological damage, complications, and even death.

The administration of the metal-DFO complexes and combinations thereof according to the invention for the treatment, amelioration or prophylaxis of diabetes may be any one of sublingual, buccal, rectal, vaginal, parenteral, intravenous, intramuscular, intraperitoneal, subcutaneous, intramedullary, transdermal, via oral or nasal inhalation, preferably intraperitoneal. It should be noted that oral, transmucosal, intestinal or parenteral delivery, including intramuscular, subcutaneous and intramedullary injections as well as rectal, intrathecal, direct intraventricular, intravenous, intraocular injections or any other medically acceptable methods of administration can be considered as well.

Furthermore, metal-DFO complexes and combinations of the invention may be administered to a subject suffering from diabetes at least once a year, more preferably, at least once every 6 months, more preferably, at least once every 3 months, more preferably, at least once every 2 months, more preferably, at least once every one month, more preferably, at least once every 2 weeks, more preferably, at least once every week, most preferably, at least twice or three times every week.

According to some embodiments, doses particularly suitable for treatment of human subjects suffering from diabetes are between 0.04 mg/kg body weight to about 4 mg/kg body weight, more specifically, between 0.08 mg/kg body weight to about 3.5 mg/kg body weight, more specifically, between 0.12 mg/kg body weight to about 3 mg/kg body weight, more specifically, between 0.16 mg/kg body weight to about 2.5 mg/kg body weight, more specifically, between 0.2 mg/kg body weight to about 2 mg/kg body weight, more specifically, between 0.24 mg/kg body weight to about 1.5 mg/kg body weight, more specifically, between 0.28 mg/kg body weight to about 1 mg/kg body weight, more specifically, between 0.32 mg/kg body weight to about 0.8 mg/kg body weight, most specifically, between 0.36 mg/kg body weight to about 0.6 mg/kg body weight.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

Pharmaceutical compositions used to treat subjects in need thereof according to the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

In various embodiments, the final solution may be adjusted to have a pH between about 4 and about 9, between about 5 and about 7, between about 5.5 and about 6.5, or about 6. The pH of the composition may be adjusted with a pharmacologically acceptable acid, base or buffer.

As indicated above, in addition to the intraperitoneal, intranasal and transdermal routes, the compositions used in the uses, methods and kits of the invention may be adapted for administration by any other appropriate route, for example by the parenteral, oral (including buccal or sublingual), rectal, topical (including buccal or sublingual) or vaginal route. Such formulations may be prepared by any method known in the art of pharmacy, for example by bringing into association the active ingredient with the carrier(s) or excipient(s).

Pharmaceutical formulations adapted for rectal administration may be presented as suppositories or enemas.

Pharmaceutical formulations adapted for vaginal administration may be presented as pessaries, tampons, creams, gels, pastes, foams or spray formulations.

Compositions and formulations for oral administration include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

Pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose or methyl cellulose or a heteropolysaccharide polymer, for example, gelan gum, may be incorporated together with a preservative, such as benzalkonium chloride. Such formulations may also be delivered by iontophoresis.

Formulations for ocular and aural administration may be formulated to be immediate and/or modified release. Modified release includes delayed, sustained, pulsed, controlled, targeted, and programmed release.

Preferred unit dosage formulations are those containing a daily dose or sub-dose, as herein above recited, or an appropriate fraction thereof, of an active ingredient.

Still further, the compositions used in the uses, methods and kits of the invention may be presented in unit dose forms containing a predetermined amount of each active ingredient per dose, which is a therapeutically effective amount. Such a unit may be adapted to provide 0.1-100 mg/Kg of body weight of the metal-DFO complexes of the invention or any combinations thereof. Specifically, between 0.01 to 100 mg/Kg may be used, specifically, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80 90 and 100 mg/Kg. More specifically, either 0.05-3.0 mg/Kg, 0.1-5 mg/Kg, 1.0-8 mg/Kg, 2.5-10 mg/Kg 40-80 mg/Kg or 60-100 mg/Kg. Such doses can be provided in a single dose or as a number of discrete doses. The ultimate dose will of course depend on the condition being treated, the route of administration and the age, weight and condition of the patient and will be at the doctor's discretion.

The term "effective amount" as used herein is that determined by such considerations as are known to the man of skill in the art. The amount must be sufficient to prevent or ameliorate tissue damage caused by immune-, inflammation- and oxidative stress related disorders treated, specifically, psoriasis, asthma and diabetes. Dosing is dependent on the severity of the symptoms and on the responsiveness of the subject to the active drug. Medically trained professionals can easily determine the optimum dosage, dosing methodology and repetition rates. In any case, the attending physician, taking into consideration the age, sex, weight and state of the disease of the subject to be treated, will determine the dose.

It will be appreciated that the human dosages described herein are estimated by converting mouse or rat dosages according to the Examples, using the conversion rules set forth by [Reagan-Shaw S et al., (2007) FASEB J, Vol. 22 March].

The present invention involves different metal complexes that may be administered through different routes, dosages and combinations. More specifically, the treatment of diseases and conditions with a combination of active ingredients may involve separate administration of each active ingredient. Therefore, a kit providing a convenient modular format of the different constituents of the complexes and related components required for treatment would allow the required flexibility in the above parameters.

Thus, in another aspect, the invention provides a kit. In some embodiments the kit of the invention may includes at least two separate pharmaceutical compositions that are required for at least one metal-DFO complex formation. For example, the compounds for Zn-DFO complex formation may include: (i) desferrioxamine, optionally in a first dosage form; (ii) a metal ion that may be zinc or gallium or any zinc or gallium salts, esters or amides thereof, in a second dosage form. For example, zinc chloride ($ZnCl_2$), gallium chloride ($GaCl_3$), zinc acetate, gallium gluconate, gallium citrate and zinc histidinate. Optionally, the kit of the invention may further comprise (iii) solutions, buffers and components which provide suitable conditions for complex formation, for extension of the shelf-life of the preparations. For example, an acidifying compound, avoiding contact with $CO_2$ or bi-carbonate or carbonate, and maintaining low pH values and titrating solutions such as HCl or NaOH. In certain embodiments, the kit of the invention may comprise separate ingredients required for formation of one DFO-metal complex. In other embodiments, the kit of the invention may comprise compounds required for different DFO-metal complexes, for example, compounds required for formation of the Zn-DFO complexes and also compounds required for the formation of the Ga-DFO complex, or any other metal-DFO complex.

According to certain embodiments, the invention provides a kit for achieving a therapeutic effect in a subject in need thereof comprising at least one of:
(I) compounds for Zn-DFO complex formation comprising:
  (i) Zinc ions (Zn(II)) in any form of salts, esters and amides thereof, or a pharmaceutically acceptable derivative thereof and a pharmaceutically acceptable carrier or diluent, optionally, in a first unit dosage form;
  (ii) DFO, or a pharmaceutically acceptable derivative thereof and a pharmaceutically acceptable carrier or diluent, optionally, in a second unit dosage form; and
  (iii) optionally solutions, buffers and components which provide suitable conditions for complex formation; and/or compounds required for extension of the shelf-life of the preparations;
(II) compounds for Ga-DFO complex formation comprising:
  (i) Gallium ions (Ga(III)) in any form of salts, esters and amides thereof, or a pharmaceutically acceptable derivative thereof and a pharmaceutically acceptable carrier or diluent, optionally, in a third unit dosage form;
  (ii) DFO, or a pharmaceutically acceptable derivative thereof and a pharmaceutically acceptable carrier or diluent, optionally, in a fourth unit dosage form; and
  (iii) optionally solutions, buffers and components which provide suitable conditions for complex formation and/or for extension of the shelf-life of the preparations;
(III) compounds for Mn-DFO complex formation comprising:
  (i) Manganese ions, in any valecy state, including but not limited to Mn(II), Mn(III) and Mn(IV), in any form of salts, esters and amides thereof, or a pharmaceutically acceptable derivative thereof and a pharmaceutically acceptable carrier or diluent, optionally, in a fifth unit dosage form;
  (ii) DFO, or a pharmaceutically acceptable derivative thereof and a pharmaceutically acceptable carrier or diluent, optionally, in a sixth unit dosage form; and
  (iii) optionally solutions, buffers and components which provide suitable conditions for complex formation and/or for extension of the shelf-life of the preparations;
(IV) container means for containing the unit dosage forms.

According to specific embodiments, the kit of the invention comprises:
(I) compounds for Zn-DFO complex formation comprising:
  (i) Zinc ions (Zn(II) in any form of salts, esters and amides thereof, for example, $ZnCl_2$, or a pharmaceutically acceptable derivative thereof and a pharmaceutically acceptable carrier or diluent, optionally, in a first unit dosage form
  (ii) DFO, or a pharmaceutically acceptable derivative thereof and a pharmaceutically acceptable carrier or diluent, optionally, in a second unit dosage form; and
  (iii) optionally solutions, buffers and components which provide suitable conditions for complex formation and/or for extension of the shelf-life of the preparations;
(II) compounds for Ga-DFO complex formation comprising:
  (i) Gallium ions (III) in any form of salts, esters and amides thereof, for example, $GaCl_3$, or a pharmaceutically acceptable derivative thereof and a pharmaceutically acceptable carrier or diluent, optionally, in a third unit dosage form;
  (ii) DFO, or a pharmaceutically acceptable derivative thereof and a pharmaceutically acceptable carrier or diluent, optionally, in a fourth unit dosage form; and
  (iii) optionally solutions, buffers and components which provide suitable conditions for complex formation; and
(III) container means for containing said unit dosage forms.

It should be noted that Zinc chloride and Gallium chloride are highly acidic, and they do not remain in solution at neutral pH. Therefore, other salts including zinc acetate, gallium gluconate, gallium citrate, zinc histidinate, and zinc and gallium esters and amides may be used by the present invention.

More specifically, the kit includes container means for containing separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

According to one embodiment, the kit of the invention is intended for achieving a therapeutic effect in a subject suffering from an immune-related disorder.

Achieving a therapeutic effect is meant for example, where the kit is intended for the treatment of a specific disorder, such as psoriasis, asthma and diabetes, the therapeutic effect may be for example slowing the progression of the treated condition.

The invention further provides a method of treating, ameliorating, preventing or delaying the onset of an immune-related disorder in a subject in need thereof comprising the step of administering to said subject a therapeutically effective amount of the unit dosage forms comprised in a kit according to the invention. In certain embodiments, the immune-related disorder is any one of an inflammatory disease and an autoimmune disease. According to more specific embodiments, such inflammatory disease is any one of a chronic or acute inflammatory-related skin pathologic condition, a respiratory diseases, and wherein said autoimmune disease is diabetes type II, diabetes type I or any diabetes related condition.

It should be appreciated that each of the multiple components of the kit may be administered simultaneously.

Alternatively, each of said multiple dosage forms may be administered sequentially in either order.

More specifically, the kits described herein can include a composition as described, or in separate multiple dosage unit forms, as an already prepared liquid topical, nasal or oral dosage form ready for administration or, alternatively, can include the composition as described as a solid pharmaceutical composition that can be reconstituted with a solvent to provide a liquid oral dosage form. When the kit includes a solid pharmaceutical composition that can be reconstituted with a solvent to provide a liquid dosage form (e.g., for oral administration), the kit may optionally include a reconstituting solvent. In this case, the constituting or reconstituting solvent is combined with the active ingredient to provide liquid oral dosage forms of each of the active ingredients or of a combination thereof. Typically, the active ingredients are soluble in so the solvent and forms a solution. The solvent can be, e.g., water, a non-aqueous liquid, or a combination of a non-aqueous component and an aqueous component. Suitable non-aqueous components include, but are not limited to oils, alcohols, such as ethanol, glycerin, and glycols, such as polyethylene glycol and propylene glycol. In some embodiments, the solvent is phosphate buffered saline (PBS).

As mentioned herein before, the inventors have previously used metal-DFO complexes, specifically, Zn-DFO and Ga-DFO in reducing ocular and skin damage following exposure to nitrogen and other mustard gases. These complexes were prepared by titrating the solutions to pH 5, using bi-carbonate or carbonate, for example, $NaHCO_3$ and then titrating with NaOH (1M) to pH 7.4. Surprisingly, the inventors have now found that at pH-values higher then 6.1, the solution reacts with air-containing $CO_2$ and leads to a marked loss of the biological activities of the complex used by the methods, compositions, kits and combinations of the invention. Therefore, to avoid exposure to $CO_2$ and oxygen, HCl was used for titration and the use of bi-carbonate or carbonate was excluded. Moreover, compositions comprising the DFO-metal complexes of the invention are now having a pH rage of between about 5.0 to 6.5. The invention therefore further provides a composition comprising a therapeutically effective amount of at least one desferrioxamine-metal complex (DFO-metal complex), wherein said composition is having a pH of between about 5.0 to 6.5, specifically, any one of 5, 5.1, 5.2, 5.3, 5.4, 5.5, 5.6, 5.7, 5.8, 5.9, 6.0, 6.1, 6.2, 6.3, 6.4 and 6.5. The composition of the invention may optionally further comprise at least one pharmaceutically acceptable carrier, diluent, excipient and/or additive.

According to one embodiment, the DFO-metal complex may be zinc-desferrioxamine complex (Zn-DFO). In another embodiment, the DFO-metal complex may be gallium-desferrioxamine complex (Ga-DFO).

In certain embodiments, the composition of the invention may be used for preventing, treating, ameliorating or inhibiting an immune-related disorder.

It should be recognized that these compositions may be used by any of the methods and kits described by the present invention.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

Throughout this application various publications are referred to in parentheses. All of these publications, and publications referred to therein, are fully incorporated herein by reference. The list of references is given at the end of the description, immediately preceding the claims.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Materials
  Desferrioxamine B—Desferal® (DFO) USP grade was purchased from Novartis AG, Switzerland.
  Zinc and gallium—Zinc chloride (catalogue number 429430) and Gallium (III) chloride (catalogue number 427128) were purchased from Aldrich Chemical, St. Louis, Mo., USA.
  Ovalbumin (catalogue number 9006-59-1) was purchased from Sigma St. Louis, Mo., USA.
  N-flurane (catalogue number L17315) was purchased from Alfa Aesar, Ward Hill, Mass., USA.
  Lipoic acid USP grade.
Antibodies
  Goat anti-human L-ferritin antibody (a kind gift from Prof. A. Konijn, The Hebrew University-Hadassah Medical School).
  Secondary rabbit anti-human H-ferritin antibody was prepared from rat heart ferritin).

Patients

Asthma Patients

Thirty-four patients undergoing nasal or sinus surgery in the Department of Otolaryngology/Head & Neck Surgery, Hadassah-Hebrew University Hospital, in Jerusalem, between June 2007 and October 2008 were prospectively recruited. All patients suffered from perennial allergy, previously diagnosed at the Allergy Clinic (by patient history, skin prick and RAST testing). Non-allergic patients or patients suffering from seasonal allergy were excluded from the study. No patients suffered from any other systemic disease, none were hypersensitive to aspirin (according to patient history and to the data from the Allergy Clinic), none were smokers, and none had been treated by antihistamines or by systemic steroids during the six weeks prior to surgery. Each patient underwent a thorough medical interview, physical examination which included anterior rhinoscopy and nasal endoscopy, and a computerized tomography scan. Twenty-three patients suffered from CRS with NP according to the criteria established by the American Academy of Allergy, Asthma and Immunology and the Task Force on Rhinosinusitis; and the European Position Paper on Rhinosinusitis and Nasal Polyps (Meltzer E O et al. (2004) Otolaryngol Head Neck Surg; 131: S1-62).

These NP patients were operated on due to failure of medical treatment (including local and systemic steroids). All NP patients suffered from total or near-total obstruction of both nostrils by polyps originating from the middle and superior nasal meatus with involvement of all sinuses, thus receiving maximal endoscopic and Lund-Mackay scores (Kennedy D W (2000) Laryngoscope 110:29-31; Lund V J et al (1993) 31:183-4). In all NP patients the inferior turbinate, the inferior nasal meatus, the nasal floor and the nasal septum were not affected by the disease. Ten NP patients suffered from concomitant bronchial asthma (previously diagnosed by patient history, physical examination, and pulmonary function tests at the Pulmonology Clinic).

Eleven patients were operated on due to non-rhinologic diseases (endoscopic repair of a cerebrospinal fluid leak and endoscopic skull base surgery). Similar to previous studies, their inferior turbinates served as controls (Muluk N B et al (2007). J Otolaryngol 36:357-66). Based on patient history, none of them has suffered from asthma. Since the nose and sinuses were normal, all controls received the minimal endoscopic and Lund-Mackay scores.

Animals

Twelve-week-old Balb/c mice and three-week-old BALB/c mice, purchased from Harlan-Israel facilities were used for the asthma models.

Sand rat (*Psammonys obesus*), purchased from Harlan-Israel facilities, were used as a model for Type II diabetes.

Sprague-Dawley (SD) male rats, purchased from Harlan-Israel facilities, treated with streptozotocin (70 mg/kg) were used as diabetes type I model.

Experimental Procedures

Synthesis of Zn-DFO and Ga-DFO Complexes and Analysis of the Yield and Purity of the Solid Complexes Zn-DFO: One liter of doubly distilled water (DDW) is purged with high purity $N_2$ gas, followed by thorough degassing and kept tightly closed to avoid exposure to $CO_2$ and oxygen. Three (3.00) grams of Desferal® is dissolved in 100 ml of the degassed DDW, and kept air-free. $ZnCl_2$, anhydrous, (623.2 mg) of highest purity available, (>98% pure, Aldrich Chemical Co., Inc.; WI, USA, Catalog #21, 127-3) is dissolved in 100 ml of the degassed DDW.

The two solutions are mixed, the pH is monitored, and brought down to pH=2.5, with HCl (1M), The solution containing all the components is heated to 35° C., with mixing, for 15 min. Using 1M solution NaOH, the pH is brought to 5.3-5.5, and then using 0.1M NaOH solution to pH=6.0-6.1. The pH should not be brought above 6.1. At higher pH-values the solution reacts with air-containing $CO_2$ and causing a marked loss of the biological activities of the complex.

The solution is frozen and freeze-dried (lyophilized). The residual sediment is collected and grinded to form a homogeneous white powder, which is kept sealed, in the dark in the freezer) (−18° C. until used.

The powder contains the Zn-DFO complex (Zinc: DFO=1.00:1.00), with additional sodium chloride, stemming from the titration of the HCl with NaOH. The concentration of sodium chloride is variable. For the analysis of the purity of the prepared powder a sample weighing ~15 mg is dissolved in degassed Tris Buffer (200 mM, pH 6/0) in DDW to make a solution of 0.4 mM (considering that the purity is 100.0%). This solution is step-wise titrated, spectrophotometrically (at 435 nm) with 4 μl aliquots of (standardized) 10 mM solution of ferric chloride, up to ferric concentration in the solution of 600 μM. A titration curve is plotted, and is comprised of two phases. Two straight lines are drawn, and the intersection point provides the exact concentration of the complex, and its degree of purity, which is calculated. Typically, the degree of purity is 78-85%.

Ga-DFO: One liter of doubly distilled water (DDW) is purged with high purity $N_2$ gas, followed by thorough degassing and kept tightly closed to avoid exposure to $CO_2$ and oxygen. Three (3.00) grams of Desferal® is dissolved in 100 ml of the degassed DDW, and kept air-free. $GaCl_3$, anhydrous (5 g ampoule) was dissolved in 500 ml of the degassed DDW, and 80.5 ml of solution was added to the DFO solution for the formation of Ga-DFO complex (805 mg, of highest purity available, 99.999+% pure, Aldrich Chemical Co., Inc.; WI, USA, Catalog #42, 712-8).

The pH of the mixed solution (~pH=2.5) is monitored. The mixed solution is heated to 35° C., with mixing, for 15 min. Using 1M solution NaOH, the pH is brought to 4.9-5.0, and then using 0.1M NaOH solution to pH=5.4-5.6. It should be noted that the pH should not be brought above 5.6. At higher pH-values the solution reacts with air-containing $CO_2$ and causing a marked loss of the biological activities of the complex.

The solution is frozen and freeze-dried (lyophilized). The residual sediment is collected and grinded to form a homogeneous white powder, which is kept sealed, in the dark in the freezer) (−18° C. until used.

The powder contains the Ga-DFO complex (gallium: DFO=1.00:1.00), with additional sodium chloride, stemming from the titration of the acid with NaOH. For the analysis of the purity of the prepared powder a sample weighing ~17 mg and dissolve in degassed Tris buffer, pH=5.6 in DDW to make a solution of 0.4 mM (considering that the purity is 100.0%). This solution is step-wise titrated, spectrophotometrically (at 435 nm) with 4 μl aliquots of (standardized) 10 mM solution of ferric chloride, up to ferric concentration of 600 μM. Each titration step takes >5 min to allow for the total exchange of gallium ion by ferric iron ion, in the complex. A titration curve is plotted, which is comprised of two phases. Two straight lines are drawn, and the intersection point provides the exact concentration of the complex, and the degree of purity of the complex is calculated. Typically, the degree of purity is 76-83%.

Collection of Human Nasal Polyps and Inferior Turbinates Samples

Thirty-four patients undergoing nasal or sinus surgery in the Department of Otolaryngology/Head & Neck Surgery, Hadassah-Hebrew University Hospital, in Jerusalem, between June 2007 and October 2008 were prospectively recruited. All patients suffered from perennial allergy, previously diagnosed at the Allergy Clinic (by patient history, skin prick and RAST testing). Non-allergic patients or patients suffering from seasonal allergy were excluded from the study. No patients suffered from any other systemic disease, none were hypersensitive to aspirin (according to patient history and to the data from the Allergy Clinic), none were smokers, and none had been treated by antihistamines or by systemic steroids during the six weeks prior to surgery. Each patient underwent a thorough medical interview, physical examination which included anterior rhinoscopy and nasal endoscopy, and a computerized tomography scan. Twenty-three patients suffered from Chronic Rhinosinusitis (CRS) with nasal polyps (NP) according to the criteria established by the American Academy of Allergy, Asthma and Immunology and the Task Force on Rhinosinusitis; and the European Position Paper on Rhinosinusitis and Nasal Polyps [Meltzer E O et al. (2004) Otolaryngol Head Neck Surg; 131: S1-62].

NP patients were operated on due to failure of medical treatment (including local and systemic steroids). All NP patients suffered from total or near-total obstruction of both nostrils by polyps originating from the middle and superior nasal meati with involvement of all sinuses, thus receiving maximal endoscopic and Lund-Mackay scores Kennedy D W et al (2000) Laryngoscope 110:29-31; Lund V J et al (1993) Rhinology 31:183-4. In all NP patients the inferior turbinate, the inferior nasal meatus, the nasal floor and the nasal septum were not affected by the disease.

Ten NP patients suffered from concomitant bronchial asthma previously diagnosed by patient history, physical examination, and pulmonary function tests at the Pulmonology Clinic.

Eleven patients were operated on due to non-rhinologic diseases (endoscopic repair of a cerebrospinal fluid leak and endoscopic skull base surgery). Their inferior turbinates served as controls [Muluk N B et al (2007). J Otolaryngol 36:357-66]. Based on patient history, none of them has suffered from asthma. Since the nose and sinuses were normal, all controls received the minimal endoscopic and Lund-Mackay scores.

Tissue samples removed during surgery were then analyzed. All assays were performed in a blinded fashion. Inferior turbinates from the control group (n=11), nasal polyps from non-asthmatic (n=15) and from asthmatic patients (n=10), were removed and immediately stored at −80° C. until used. Each sample was homogenized in a lysis buffer, using a Cole Parmer Teflon homogenizer. Protein concentrations in the lysate were determined using a Bicinchoninic Acid Kit (Pierce, USA) in accordance with the manufacturer's instruction.

Determination of Ferritin Concentration

Ferritin concentration was quantified using an indirect 'sandwich' ELISA assay in accordance with a procedure developed previously in our laboratory. Briefly, ELISA 96-well micro plates were pre-coated with goat anti-human L-ferritin antibody. Rabbit anti-human H-ferritin was used as the secondary antibody. Plates were treated with goat anti-rabbit IgG conjugated with β-galactosidase. Chlorophenol Red-β-D-Galactopyranoside was then added and the plates analyzed using a microplate reader with a test (570 nm) and reference (630 nm) filters.

Determination of Ferritin-bound Iron

For ferritin-bound iron measurement equal volumes of sample and anti-H and anti-L ferritin antibodies (diluted with lysis buffer) were mixed and incubated in a cold room for a period of 72 h. The samples were then centrifuged at 20,000×g for 20 min, the supernatant was disposed of, and the pellet was dissolved with 32% $HNO_3$. The total amount of iron was measured spectrophotometrically with bathophenanthroline bi-sulphonate, using 535 nm filters, using Zeeman Atomic Absorption Spectrophotometer. The level of ferritin saturation by iron was calculated.

Induction of Asthma in Mice

Twelve-week-old Balb/c mice were administered 10 μg (100 μl) ovalbumin (OVA) dissolved with 3 mg $Al(OH)_3$ in 0.9% saline intraperitoneally (i.p.) on days 0, 7 and 14, and 10 μg (50 μl) OVA intranasally (i.n.) on days 20, 23, 25, 27, 29, 31, 34, 36, 37, 41, 43 and 45. For intranasal administration, mice were anesthetized with inhaled N-flurane and instilled with OVA i.n. with a micropipette.

Three-week-old BALB/c mice were sensitized (×3) with intra-peritoneal (i/p) injection (100 μl OVA solution, containing 0.3 mg OVA and 6.7 mg $Al(OH)_3$, in 1 ml PBS) on days 0, 7 and 14. On days 14, 15, 17, 21 and 23 the mice were further sensitized with intranasal sprinklings (50 μl, each) of OVA in PBS solution containing 2 mg/ml OVA, as following: mice were anesthetized with inhaled N-flurane and instilled with OVA intranasally using a micropipette. Twenty-four hours after the last administration of OVA, the mice were sacrificed.

Methacholine Challenge and Collection of Histologic Sections and Biochemical Samples Animals were anesthetized by a single injection of ketamine/xylazine mixture. Methacholine was administered [Renstrom A et al. (1995) Eur. Respir. J. Sep; 8(9):1514-9] in three consequent intra-nasal sprinklings of 10 μl 0.5 mg/ml methacholine every 5 minutes, preceded by 3 minutes of stabilization. The animals were then sacrificed by additional injection of ketamine/xylazine mixture. Bronchoalveolar lavage (BAL) with 1 ml of saline buffer was performed immediately after the last methacholine challenge. The amounts of eosinophils and neutrophils in the BAL fluid were calculated. Then the lungs were excised and histologically assayed, using peribronchial infiltrate measurement, Periodic Acid Schiff (PAS) staining for epithelial cells metaplasia, and Mason's trichrome staining for fibrous connective tissue. For the biochemical analyses the lungs were homogenized in lysis buffer using a Cole Parmer Teflon homogenizer.

Sand-rat Diabetes Mellitus Type-2 Model

Sand rats (*Psammomis Obesus*) were used as a model for Type 2 diabetes. The sand rats transferred onto high energy diet develop a severe form of Type 2 diabetes, including high blood glucose level, increase in body weight, and cataract development (eye lens opacification).

The sand rats were divided into groups. The animals from the Group I received the standard diet, serving as a control, whereas animals from the other indicated groups received high energy diet, leading to diabetes development. The high-energy diet ed mice were either untreated, or treated with intra-peritoneal injections of 2.5 mg/kg body weight Ga-DFO, Zn-DFO, DFO alone, Zn, Ga or lipoic acid (LA), either twice or three times per week, as indicated, for the duration of the experiment. The blood glucose and body weight of the animals were monitored throughout the experiment.

Sprague-Dawley Diabetes Mellitus Type-1 Model

Sprague-Dawley rats as a model for Type I diabetes. The rats were turned to diabetics by streptozotocin (STZ) injection and treated with Ga-DFO/Zn-DFO 1:3 mixtures.

Twenty four Sprague-Dawley (SD) male rats were separated into two groups, 12 animals in each. The first group was turned to diabetic (SD group) by single injection of streptozotocin 70 mg/kg i.p. The second group considered the control one and received a single injection of 0.25 ml saline i.p. The blood glucose level was measured twice a week. Three days after the injection the animals from the second group have demonstrated high level of blood glucose, showing the onset of diabetes. At the second week the treatment with Ga/Zn-DFO was started. Each group was separated into two subgroups, 6 rats in each one. The animals from one diabetic subgroup and one control subgroup have received the injections of the Ga-DFO/Zn-DFO mixture 0.25 mg/kg i.p twice a week, while their blood glucose and body weight were monitored. The untreated subgroups have received saline according to the same pattern.

2,3-DHBA Assay

To measure 2,3-DHBA the animals were injected i.p. with 100 mg/kg salicylate in saline buffer. As a product of salicylate hydroxylation, the 2,3-DHBA was quantified using HPLC coupled with electrochemical detection (HPLC-ECD), using a Varian 5000 liquid chromatograph (Varian Analytical Instruments, Walnut Creek, Calif., USA) equipped with a Rheodyne 7125 sample injector (20 μA loop; Rheodyne L. P., Rohnert Park, Calif., USA). The column used for separation of salicylate and DHBA was a 250×4 mm LiChrospher 100RP-18, 5 μm (Merck, Darmstadt, Germany). The chromatograms were recorded using a PC-based data acquisition and processing system (EZChrom Elite, San-Ramon, Calif., USA).

Msr Activity Assay

Quantification of the activity of methionine-sulfoxide reductase (Msr) was carried out by incubation the tissue lysates with dabsyl-methionine sulfoxide for 30 min at 37° C., followed by analysis of the reduced product (dabsyl methionine) by HPLC-spectrophotometric detection at 436 nm Assay: total volume 100 μl, including 200 μM Dabsyl-met (O) (as a substrate). The reaction mixture contained also 20 mM DTT, buffer, ~100 μg protein. The incubation (reaction) was stopped by adding 100 μl of acetonitrile, spinning down, and discarding the protein fraction. The chromatography was run on a 150 mm 3 μm C-18 column, using a gradient (A to B). A=19 g of sodium acetate, pH 6.0 plus 0.5 ml of triethylamine, in one liter of solution; B=acetonitrile (pure). The substrate, dabsyl-Met (O) was prepared as described [Moskovitz, J. et al. (2001) Proc Natl. Acad Sci USA, 98 (23): p. 12920-5; Moskowitz et al. (1997) Proc Natl Acad Sci USA, 94 (18): p. 9585-93].

Example 1

Ferritin and Ferritin-bound Iron Content of Asthmatic and Non-asthmatic Nasal-polyposis Patients The aim of the initial experiment was to examine and support the accumulation of iron in inflamed tissues of the airways, especially in nasal polyposis and asthma, and accumulation of ferritin in nasal polyps of asthmatic patients.

Thirty-four patients suffering from perennial allergy were prospectively recruited. Patients suffering from seasonal allergy were excluded from the study, as were patients suffering from any other systemic disease. Twenty-three patients suffered from CRS with nasal polyposis (NP), ten of these NP patients suffered from concomitant bronchial asthma. Eleven patients suffering from non-rhinologic diseases served as controls. The patients were divided into three groups: (i) NP asthmatic patients (n=10); (ii) NP non-asthmatic patients (n=13) and (iii) patients suffering from non-rhinologic diseases (control patients, n=11). Inferior turbinates samples were collected from control patients (suffering from non-rhinologic diseases) and nasal polyps were collected from asthmatic and non-asthmatic nasal-polyposis patients. The tissue levels of ferritin per mg protein and ferritin-bound iron were assayed.

As illustrated by FIG. 1A, the inventors found that the tissue level of ferritin from NP asthmatic patients was 1.9-fold higher than the control level assayed (1.34±0.36 versus 0.69±0.24 μg ferritin per mg protein, respectively). No significant difference was found in tissue ferritin between non-asthmatic nasal polyps and controls. FIG. 1B depicts the amount of ferritin-bound iron (FBI) in NP from controls, non-asthmatic NP patients and asthmatic NP patients. FBI was 1.6-fold in non asthmatic NP patients than in controls, and 4.0-fold higher in asthmatic NP patients.

Example 2

Treatment of Asthma in an Animal Model by Metal-DFO Complexes

The inventors postulated that the compositions of the invention may be beneficial for the treatment of reactive oxygen species (ROS)-related disorders, since the zinc and gallium desferrioxamines and their combinations (metal-DFO complexes herein) inhibit the labile-iron-catalyzed production of said radicals. Asthma is known to be associated with a significant increase in ROS production and an aggravation of inflammatory condition. The inventors set about investigating the potential beneficial effects of zinc and gallium desferrioxamines and their combinations on asthma.

Two animal models of ovalbumin-induced asthma were used, simulating either prophylactic treatment or treatment of chronic asthma condition [Kung T T et al (1994) Int Arch Allergy Immunol 1994 September; 105(1):83-90].

For a model of prophylactic treatment, twelve-week-old BALB/c mice were divided into 3 treatment groups, 4 animals in each. The animals were sensitized to ovalbumin (OVA) as described in the Experimental Procedures.

Either Zn-DFO, Ga-DFO, Zn-DFO and Ga-DFO 1:1 combination (herein metal complexes) or saline were administered as follows: on days −5, −1, 7 and 14, 1 mg/kg body weight metal complexes or saline were administered intraperitoneally (i.p.). On days 0, 6, 8, 13 and 15, 0.3 mg/kg body weight metal complexes or saline were administered i.p. On days 20, 23, 25, 27, 29, 31, 34, 36, 37, 41, 43 and 45, 0.3 mg/kg body weight metal complexes or saline were administered intranasally (i.n.). Twenty-four hours after the last sensitization, mice were anesthetized with urethane and the lungs were lavaged 4 times with 0.5 ml sterile PBS. Animals in the "control" group (non-asthmatic—saline treated, but not sensitized) (n=6) received saline injections and instillations, using the same regime as the asthmatic and treated animals. Animals of the "asthmatic" group (sensitized and saline-treated, rather than complex-treated) (n=6) received saline instead of the respective complex, under the same regime.

For the treatment of chronic asthma model, a similar experimental protocol was followed, with the following modifications: 1 mg/kg body weight metal complexes or saline were administered i.p. on day 0 (instead of days −5 and −1) and a further 0.3 mg/kg complexes or saline were administered on day 1. In this model, the effects of the complexes were investigated further by histological examination of lung sections stained with either haematoxylin-eosine or PAS/AB (periodic acid-Schiff/alcan blue).

To estimate the anti-asthmatic effect of the complexes the following parameters were measured: the concentration of ferritin in the lungs, the presence of inflammatory cells infiltration into the lungs, and the amounts of macrophages, eosinophils, lymphocytes and neutrophils in bronchoalveolar lavages (BALs).

In the prophylactic treatment model, the concentration of lung ferritin from normal non-treated BALB/c mice was 0.4±0.1 µg ferritin per mg protein. Induction of asthma by OVA and treatment with saline induced a 3.5-fold increase to 1.4±0.4 µg ferritin/mg protein. In lungs of asthmatic mice treated with Zn-DFO, Ga-DFO or their (1:1) combination, a sizeable decrease in ferritin levels, to 0.6±0.2, 0.5±0/3 and 0.5±0.2 µg/mg, respectively, was observed.

Likewise, in the treatment of the chronic asthma inflammation model, the presence of infiltration of inflammatory cells, with or without treatment, was monitored. As presented by Table 1, haematoxylin-eosine stained lung sections showed that sensitization to OVA has increased the numbers of eosinophils and lymphocytes in the lung tissue sections when compared to lungs of control animals. Furthermore, structural damage to the airway epithelium and goblet cell metaplasia and hyperplasia, with a mucus overproduction was observed in the sensitized lungs, when stained with PAS/AB. Treatment of OVA-sensitized mice with the complex significantly reduced the number of eosinophils and lymphocytes in the peribronchial and alveolar regions, and attenuated the damage to the airway epithelium and mucus overproduction. Treatment with saline had no effect on the appearance of eosinophils and lymphocytes in lung tissue, damage to the airway epithelium, or mucus hyper-secretion.

Table 1 also illustrates that the total cell numbers in bronchoalveolar lavages (BALs) of chronic asthma-simulating mice (mice sensitized and saline-treated, rather than complex-treated) significantly increased, at 24 h after last sensitization, compared with saline instillation (non-sensitized mice). The increase of total cell numbers was associated with macrophages, eosinophils, lymphocytes and neutrophils. As compared with control group, treatment of OVA-sensitized mice with the complex significantly inhibited the increase in total cell numbers in BAL. Eosinophils and lymphocytes decreased after treatment with the complex, whereas treatment with saline had no effect on the BAL eosinophilia.

on asthma. To that end, three-week-old BALB/c mice were sensitized to ovalbumin (OVA) as described in the Experimental Procedures, and either not treated (Group 1) or treated (Group 2) with the combination of Zn-DFO/Ga-DFO in a 1:1 ratio, administered both i.p. and i.n. Twenty-four hours after the last administration of OVA, the mice were sacrificed.

Treated mice (Group 2) received three 1 mg/kg body weight Zn-DFO/Ga-DFO i.p. on days −5, −1 and days 0, 7, 14. Mice were further treated with 0.3 mg/kg body weight Zn-DFO/Ga-DFO i.p. on days 1, 6, 8 and 13. On days 15, 17 21 and 23 mice were treated i.n. with 1 mg/kg body weight Zn-DFO/Ga-DFO, and on days 16, 18, 20, 22 and 24 mice received i.n. 0.3 mg/kg body weight Zn-DFO/Ga-DFO.

The mice from group 2 have received prophylactic treatment by two i.p. injections (100 µl each) containing 1 mg of Zn/Ga-DFO in PBS, per kg body weight 5 days and 1 day before their first OVA sensitization. Subsequently, the i.p. injections contained only ⅓ of the dose (0.3 mg of Zn-DFO/Ga-DFO in PBS, per kg body weight), were performed on one day before and one day after the OVA sensitization, while a dose of 1 mg of Zn-DFO/Ga-DFO in saline per kg body weight was given at the day of OVA sensitization. Starting from day 15 Zn-DFO/Ga-DFO was given intra-nasally.

Animals in the "control" group (non-asthmatic—saline treated, but not sensitized) received saline injections and instillations, using the same regime as the treated asthmatic animals.

Twenty-four hours after the last administration of OVA, the animals were anesthetized and subjected to acute challenge by methacholine as described in Experimental procedures, after which they were sacrificed. Bronchoalveolar lavages were carried out immediately, and lung sections were taken for histological analyses. The biochemical analyses for ferritin concentration and its saturation with iron were performed as previously described.

The density of eosinophils measured in the BAL fluid of unsensitized and untreated control mice lungs, was $2.0±0.6×10^4$ cells per ml. Asthma (sensitization with OVA) caused ~5.5 fold increase in this parameter, to $11.0±0.2×10^4$ cells per ml. No differences were found between the lungs of the

TABLE 1

Cells populations in mice BAL fluid

| | Total WBC | Macrophages | Eosinophils | Lymphocytes | Neutrophils |
|---|---|---|---|---|---|
| Control | 2.0 ± 0.5 | 1.8 ± 0.5 | 0.01 ± 0.01 | 0.03 ± 0.02 | 0.01 ± 0.01 |
| Asthma | 8.0 ± 1.0* | 4.0 ± 0.5* | 2.2 ± 0.4* | 1.2 ± 0.5* | 0.4 ± 0.1* |
| Asthma + -Zn-DFO | 4.0 ± 0.3# | 3.0 ± 0.2# | 0.3 ± 0.05# | 0.2 ± 0.05# | 0.2 ± 0.05# |
| Asthma + Ga-DFO | 4.5 ± 0.6# | 3.3 ± 0.2# | 0.2 ± 0.02# | 0.3 ± 0.06# | 0.3 ± 0.07# |
| Asthma + Zn-DFO + Ga-DFO | 4.6 ± 0.5# | 3.4 ± 0.9# | 0.3 ± 0.08# | 0.4 ± 0.01# | 0.3 ± 0.09# |

Mean ± SE are shown;
All the values are given in $10^4$ cells/ml.
Abbreviations:
Control (non-sensitized and non-treated);
WBC (white blood cells).
*denotes $p < 0.05$ between the asthmatic group and the control;
denotes $p < 0.05$ between the asthmatic (not treated) and treated groups.

Example 3

Effects of Zn-DFO and Ga-DFO Combination on Asthma

The inventors next set out to characterize the beneficial effects exerted by the combination of Zn-DFO and Ga-DFO asthmatic mice (OVA-sensitized, but untreated mice) and the lungs of the group treated by Zn/Ga-DFO i.p. and i.n.

Figure 2:
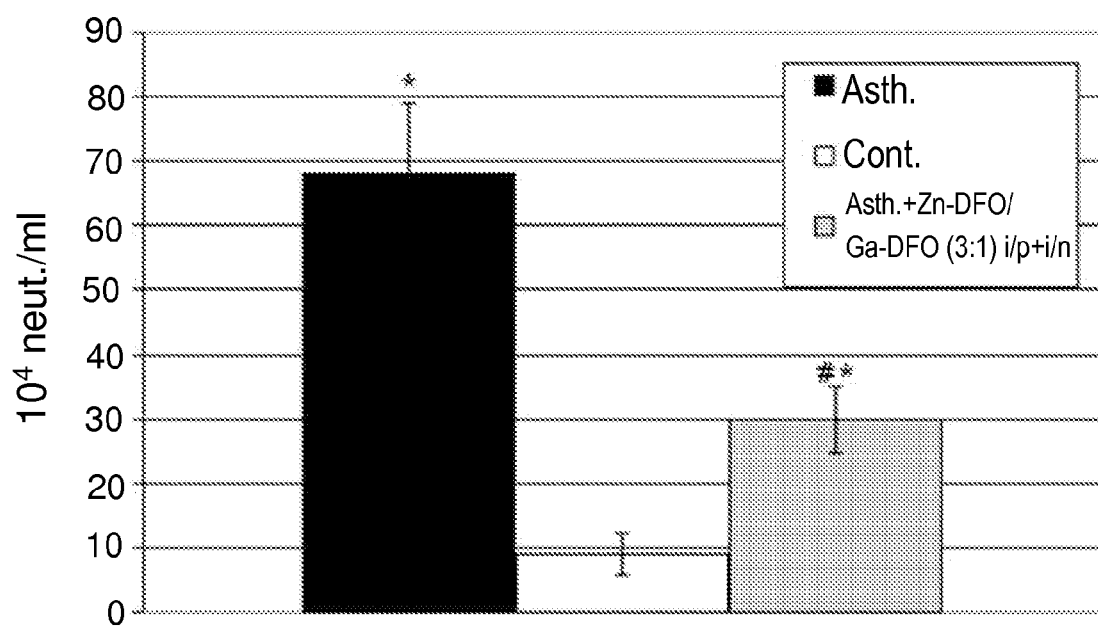

As shown by FIG. 2, the density of neutrophils measured in the BAL of control mice was $9.0±3.2×10^4$ cells per ml. In the asthmatic mice lungs, a 7.6-fold increase was detected, reaching 68.0±11.0×10$^4$ cells per ml. The value for the Zn/Ga-DFO treatment via both i.p. and i.n. decreased by 2.3-fold, to 30.0±5.1×10$^4$ cells per ml.

FIG. 3 demonstrates lung histological scores based on integer values scale from 0 to 3. Generally, in peribronchial infiltrate (PI) analysis (FIG. 3A), PAS staining for epithelial cells metaplasia (FIG. 3B) and Mason's trichrome staining for fibrous connective tissue (FIG. 3C), the same pattern was observed. In the asthmatic non-treated group the highest average value of approximately 2.5 was demonstrated, while in the control group the level was 0. The Zn/Ga-DFO i.p.- and i.n.-treated group the value of all three parameters was below 1.5, demonstrating an efficient anti-asthmatic effect of the complexes.

FIG. 4A presents the measured ferritin concentrations in the lungs of mice from the experimental groups. The baseline amount, found in the control group was 0.18±0.05 μg ferritin per mg protein; in the asthmatic lungs the level increased significantly to 0.50±0.13 μg/mg protein, and in lungs from asthmatic mice treated with Zn/Ga-DFO via i.p. and i.n. the value observed was 0.19±0.06 μg ferritin/mg protein.

The levels of ferritin saturation with iron in lungs from the same groups were measured, and presented by FIG. 4B. In the treated lungs, the value of ferritin-bound iron (FBI-value) decreased below the control level.

Example 4

Intra-nasal Versus Sequential Intra-peritoneal and Intra-nasal Administration of Zn-DFO and Ga-DFO Combination To determine whether i.n. or sequential i.n.-i.p. administration of the combined metal complexes of the invention produces better results, three-week-old BALB/c mice were sensitized to ovalbumin (OVA) as described in the Experimental Procedures. Asthmatic mice were divided into three groups: (1) untreated, (2) treated, sequentially by i.p. (2 weeks) and i.n., (2 weeks) with the combination of Zn-DFO/Ga-DFO (3:1); and (3) treated with the combination of Zn-DFO/Ga-DFO i.n. only.

Mice from group 2 have received three 1 mg/kg body weight Zn-DFO/Ga-DFO i.p. on days −5, −1 and days 0, 7, 14. These mice were further treated with 0.3 mg/kg body weight Zn-DFO/Ga-DFO i.p. on days 1, 6, 8 and 13. On days 15, 17 21 and 23 mice were treated i.n. with 1 mg/kg body weight Zn-DFO/Ga-DFO, and on days 16, 18, 20, 22 and 24 mice received i.n. 0.3 mg/kg body weight Zn-DFO/Ga-DFO.

Group 3 received 5 mg of Zn/Ga-DFO in saline buffer per kg body weight intra-nasally only, according to the same pattern:
Mice treated by intranasal instillations (Group 3) received three 5 mg/kg body weight Zn-DFO/Ga-DFO i.p. on days −5, −1 and days 0, 7, 14. Mice were further treated with 1.66 mg/kg body weight Zn-DFO/Ga-DFO i.p. on days 1, 6, 8 and 13. On days 15, 17 21 and 23 mice were treated i.n. with 5 mg/kg body weight Zn-DFO/Ga-DFO, and on days 16, 18, 20, 22 and 24 mice received i.n. 1.66 mg/kg body weight Zn-DFO/Ga-DFO.

Animals in the control group (non-asthmatic—saline treated, but not sensitized) received saline injections and instillations using the same regime as the asthmatic and treated animals.

Twenty-four hours after the last administration of OVA, the animals were anesthetized and subjected to acute challenge by methacholine as described above, after which they were sacrificed. Bronchoalveolar lavages were carried out immediately, and lung sections were taken for histological analyses. The biochemical analyses for ferritin concentration and its saturation with iron were performed as previously described.

FIG. 5 shows the density of eosinophils and neutrophils in BAL fluid. FIG. 5A demonstrates that the eosinophils density observed in the BAL fluid from the control group, was the lowest one, 2.0±0.6×10$^4$ cells per ml. Asthma caused ~5.5 fold increase in this parameter. Continuing the trend, demonstrated in the previous experiment, no differences were found between the asthmatic mice lungs and the lungs from the group that received combined Zn-DFO/Ga-DFO i.p. and i.n. (group 2). However, the intra-nasal sprinklings only of combined Zn-DFO/Ga-DFO (Group 3) have led to a decrease to the baseline level.

FIG. 5B shows the density of neutrophils in BAL. The level in control mice lungs was 6.8±2.6×10$^4$ cells per ml. In the non-treated but asthmatic mice lungs a 6.3-fold increase was detected. In the asthmatic-treated group (given combined Zn-DFO/Ga-DFO, i.p. and i.n.; group 2) the value decreased to 29.8±4.3×10$^4$ cells per ml, a value above the control, while in i.n. only treated mice (group 3) the amount of neutrophils in BAL decreased to a value below the baseline, 2.0±0.6×10$^4$ cells per ml.

A comparison of the mucus content values presented in Table 2, the inventors found that both methods of treatment were able to reduce it to the baseline.

TABLE 2

Mucus content in the lungs of mice

| Group | Mucus content value |
| --- | --- |
| Asthma | 0.8 ± 0.2 |
| Control | 0 |
| Asthma + Zn-DFO/Ga-DFO i.p. | 0 |
| Asthma + Zn-DFO/Ga-DFO i.p. + i.n. | 0 |

Histological analysis of peribroncheal infiltrate, PAS and Mason's trichrome staining was scored on integer values scale from 0 to 3 and the resulting averages are presented in FIG. 6.

In general, the patterns of the results of peri-bronchial infiltrate (PI) (FIG. 6A), PAS staining for epithelial cells metaplasia (FIG. 6B) and Mason's trichrome staining for fibrous connective tissue (FIG. 6C), for the various experimental groups, were similar to each other. As already shown in the previous experiment, the asthmatic group received the highest average score value (approximately 2.5), while the control level was 0. Both modes of treatment succeeded in decreasing the asthma-associated parameters at least 1.5-fold, while the i.n. treatment alone has shown more profound effect than i.p. injections combined with i.n. sprinklings.

The concentrations of ferritin in lungs of mice from the four experimental groups were measured and are presented in FIG. 7A. The baseline ferritin concentration, observed in the control lungs, was 0.17±0.02 μg ferritin/mg protein. A significant increase was found in the asthmatic (non-treated) lungs—0.45±0.06 μg/mg protein. In i.n.-treated lungs, a value of 0.28±0.04 μg ferritin/mg protein was observed. In the lungs treated by both i.p. and i.n., a treatment that appears highly successful, ferritin concentration was down-regulated to almost the control level—to 0.21±0.04 μg ferritin/mg protein.

Although the levels of ferritin iron saturation with in the lungs of asthmatic and control mice were similar, as can be seen in FIG. 7B, the total amount of ferritin-bound iron (FBI) in asthmatic mice lungs was 2.7 times higher, due to higher ferritin concentration. The treatment, with Zn/Ga-DFO either i.p. and i.n. or i.n. only, was able to decrease not only the general amount of ferritin, but also the level of its saturation with iron. However, no significant differences in FBI between both treated groups were found.

Example 5

Treatment with Ga-DFO Yields Normal Blood Glucose Level in Diabetic Sand Rats

Encouraged by the beneficial effect of the complexes of the invention on an inflammatory condition demonstrated using the asthma model, the inventors next examined the potential beneficial effect of the complexes of the invention on another immune-related disorder, using type II diabetes models. Thus, the possible use of Ga-DFO in prophylaxis and/or amelioration of diabetes type II was next examined. The experiment was performed using the sand rat (*Psammomis obesus*) as a model for Type II diabetes.

The sand rats were divided into four groups (6 animals in each). Animals from Group I received the standard diet, serving as a control. The animals from the Groups II, III and IV received high energy diet, leading to diabetes development, while Groups III and IV were treated with Ga-DFO and lipoic acid (LA), respectively. The intra-peritoneal injections of 2.5 mg Ga-DFO or LA per kg body weight were performed twice a week, for 61 days. The blood glucose and body weight of the animals were monitored during all the experiment.

Table 3 demonstrates that the initial blood glucose values of all the 4 groups were almost equal. After a month of high energy diet the animals from Group II have developed severe form of diabetes, demonstrating an increase in blood glucose level from 96±4 up to 284±27 mg/dl. This level slightly decreased for the next week to 221±36 mg/dl, remaining high until the end of experiment (252±22 mg/dl). The blood glucose level of the animals from Group IV, treated with LA, has increased after the third week up to 259±49 mg/dl, but later decreased to 168±33 mg/dl. The Group III animals that received Ga-DFO demonstrated a more modest increase on day 21 to 176±46 mg/dl. Moreover, later, the normal level of blood glucose (98±29 mg/dl) was restored.

Example 6

Ga-DFO and Zn-DFO Ameliorate High Blood Glucose Levels and Prevent Cataract Development in a High-energy Diet-induced Diabetes Type II Model The inventors next tested whether Zn-DFO, as well as Ga-DFO, imparts similar beneficial effects in a diabetes type II model, and whether they protect from development of cataract, a known diabetes complication.

Forty two sand rats were divided into seven groups, six animals in each. The animals from Group I received the standard diet and used as a control. The animals from the Groups II, III, IV, V, VI and VII received high energy diet, leading to diabetes development, while Groups III, IV and VII were treated with Zn-DFO, Ga-DFO and DFO alone, respectively. The Groups V and VI received Zn and Ga, in their chloride salt form, alone respectively. Administration of the different treatments was as described, and the experiment lasted for 53 days. Glucose tolerance test was performed at the end of experiment. The cataract formation was tested as well.

Figure 8:
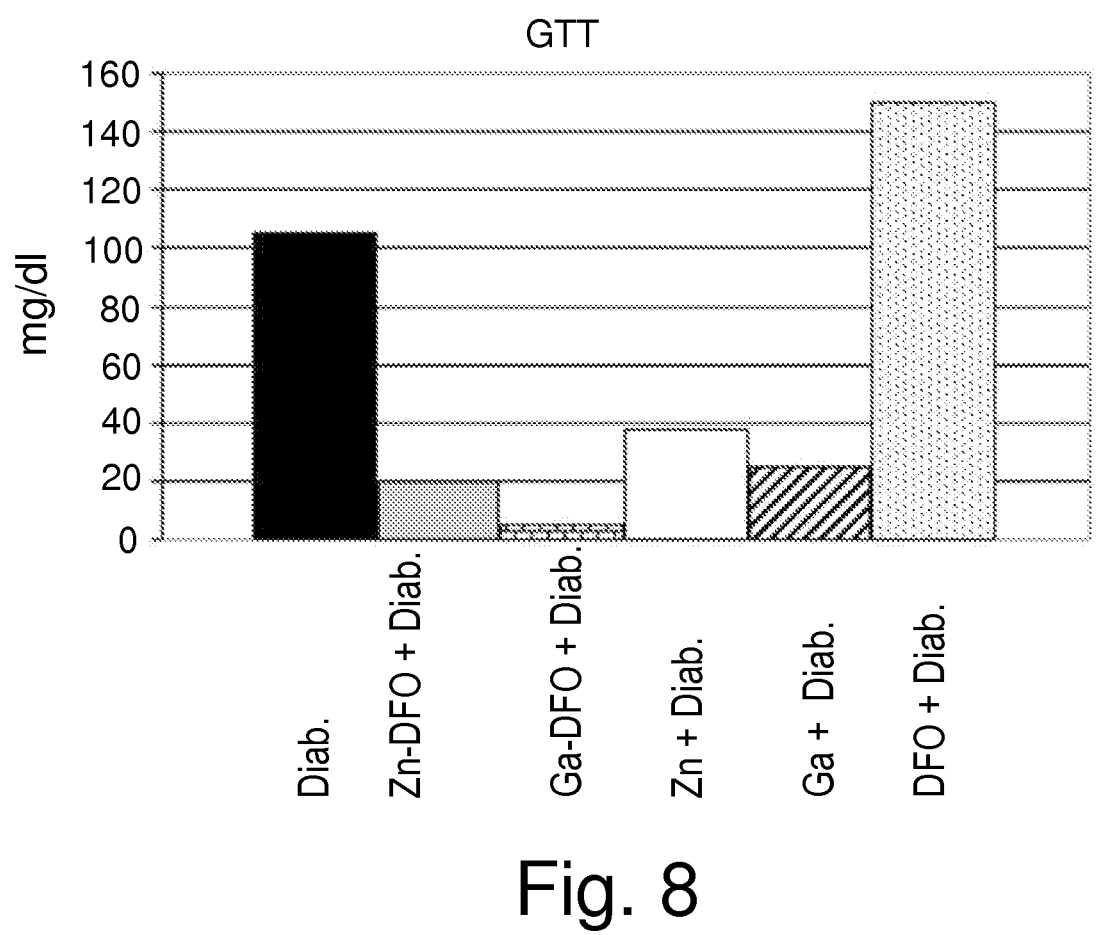

FIG. 8 presents the three hours response to an orally-administered dose of 200 mg glucose per 100 g body weight. The result of the standard diet Group I was considered as zero

TABLE 3

Blood glucose level in the treated and non-treated sand rats

| | Day 0 | Day 7 | Day 21 | Day 32 | Day 42 | Day 49 | Day 56 | Day 61 |
|---|---|---|---|---|---|---|---|---|
| Group I: Normal control | 99.2 ± 5.1 | 95.0 ± 3.2 | 94.4 ± 3.6 | 103.0 ± 6.2 | 89.4 ± 2.9 | 93.0 ± 7.6 | 68.6 ± 4.1 | 97.4 ± 4.9 |
| Group II: Diabetes | 96.2 ± 4.5 | 95.6 ± 4.2 | 98.4 ± 7.7 | 283.6 ± 26.7 | 221.4 ± 35.9 | 212.4 ± 43.2 | 242.2 ± 50.0 | 251.8 ± 22.5 |
| Group III: Diabetes + Ga-DFO | 91.8 ± 4.9 | 94.6 ± 4.7 | 176.4 ± 45.9 | 81.2 ± 2.6 | 89.0 ± 4.2 | 122.0 ± 43.2 | 129.2 ± 34.5 | 97.8 ± 29.3 |
| Group IV: Diabetes + LA | 92.8 ± 2.3 | 97.4 ± 7.8 | 259.4 ± 48.6 | 176.4 ± 47.2 | 196.4 ± 42.5 | 185.2 ± 44.7 | 220.6 ± 37.0 | 167.8 ± 32.6 |

Mean values ± SD are shown.

Table 4 presents a comparison of the body weight of treated and untreated animals. As can be seen, although the animals from all the groups have gained body weight, the increase in diabetic Group II was much more sizeable than in controls. However, animals treated with Ga-DFO demonstrated a significant improvement in blood glucose, gaining weight in a similar manner to the untreated diabetic animals.

(baseline) value. The high energy diet Group II has demonstrated the value of 105 mg/dl above the zero value. The Zn-DFO-treated animals displayed a value of 20 mg/dl above the zero, with the Ga-DFO treatment even more successful, showing a value of 5 mg/dl above the zero. Zn alone and Ga alone were useful as well, showing the values of 38 and 25 mg/dl above the zero respectively. In contrast, DFO alone

TABLE 4

Body weight in the treated and non-treated sand rats

| | Day 0 | Day 7 | Day 21 | Day 32 | Day 42 | Day 49 | Day 56 | Day 61 |
|---|---|---|---|---|---|---|---|---|
| Group I: Normal control | 129.0 ± 3.2 | 146.6 ± 12.7 | 160.2 ± 14.3 | 173.8 ± 13.2 | 179.0 ± 15.1 | 182.4 ± 14.4 | 183.2 ± 14.7 | 187.2 ± 14.8 |
| Group II: Diabetes | 143.4 ± 12.6 | 149.4 ± 11.8 | 159.2 ± 12.5 | 184.0 ± 12.4 | 197.0 ± 14.5 | 203.0 ± 14.7 | 210.4 ± 16.1 | 220.5 ± 19.9 |
| Group III: Diabetes + Ga-DFO | 131.6 ± 4.3 | 154.0 ± 1.9 | 173.2 ± 3.2 | 180.4 ± 2.9 | 192.4 ± 1.6 | 204.0 ± 0.7 | 212.4 ± 1.5 | 214.4 ± 2.6 |
| Group IV: Diabetes + LA | 113.4 ± 5.9 | 137.0 ± 6.3 | 160.4 ± 4.2 | 170.2 ± 4.9 | 189.2 ± 3.4 | 201.4 ± 6.1 | 211.8 ± 9.9 | 218.0 ± 9.2 |

Mean values (g) ± SD are shown.

produced a deleterious effect, increasing the blood glucose level, at three hours response even above the Group II value, to 150 mg/dl.

Table 5 presents a comparison of cataract formation in all the experimental groups. No cataractous eyes were observed in the control Group I. In 67% of the Group II animals, cataract was observed. Zn-DFO and Ga-DFO treatment have decreased the incidence of cataract formation to 22% and 11% respectively. Zn only and Ga only treated groups developed cataract in 22% and 36% of the animals, respectively. In Group VII (DFO alone) 25% of the animals developed cataract.

TABLE 5

Formation of diabetes-induced cataract in the treated and non-treated sand rats

| Group | Control | High energy diet (HE) | HE + Zn-DFO | HE + Ga-DFO | HE + Zn | HE + Ga | HE + DFO |
| --- | --- | --- | --- | --- | --- | --- | --- |
| Cataract (%) | 0 | 67 | 22 | 11 | 22 | 36 | 25 |

Cataract formation in the sand rats' eyes (%) is shown; HE (high energy diet) animals developed diabetes.

Example 7

Zn-DFO Protects Sand Rats Lens Proteins from Oxidation and Degradation in a High-energy Diet-induced Diabetes Type II Since diabetes induces increased oxidation, diabetic cataract development is associated with protein oxidation, decrease in activity and degradation. As a further indication for the anti-oxidative and protective effects exerted by the metal-DFO complexes of the invention, the inventors investigated protein content and activity in untreated and treated diabetic sand rats lens. Thus, the specific parameters related to diabetes-induced vision diseases were monitored.

Nineteen sand rats were divided into three groups. Group I (n=4) received a standard diet and was used as a control. Groups II (n=7) and III (n=8) received a high energy diet, leading to diabetes development. Group III was treated with 2.5 mg Zn-DFO i.p. per kg body weight three times a week, while Group II was injected with saline according to the same pattern. After the blood glucose and body weight monitoring for 63 days, glucose tolerance test was performed and blood level of 2,3-DHBA and catechols was also measured. As previously done, cataract formation was tested as well. The retina and lens were collected for biochemical analysis of the concentration of ferritin, thioredoxin-1 (Trx) and thioredoxin reductase-1 (TrxR), total lens protein and methionine sulfoxide reductase (Msr) activity. The concentration of actin, Trx and TrxR were measured by Western Blotting, and the activity of Msr was analyzed by HPLC as described.

Figure 9:
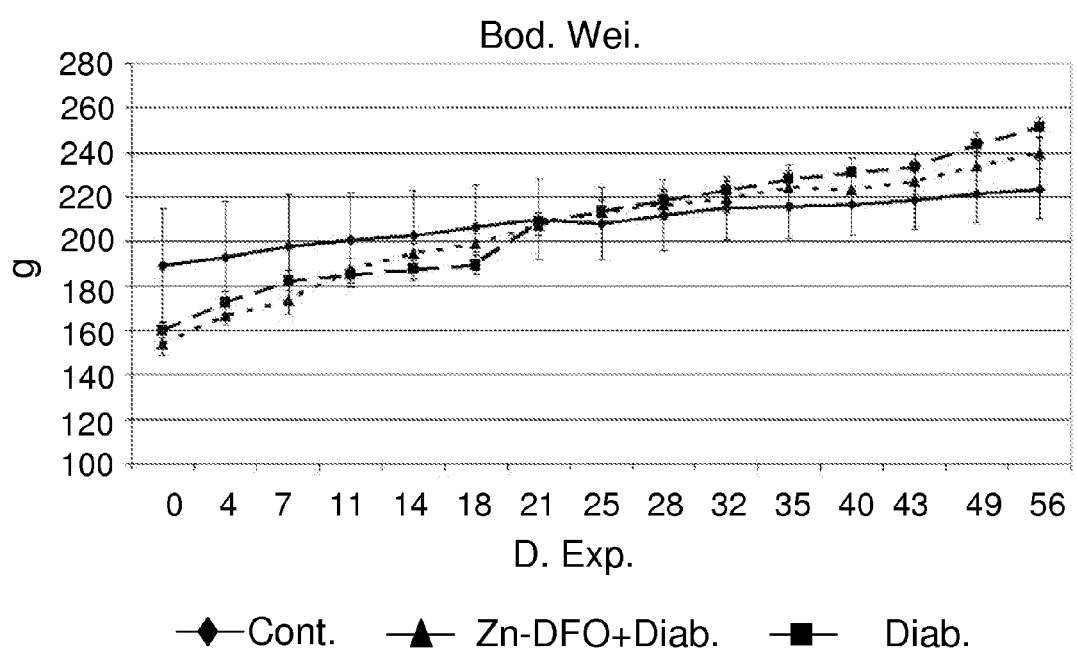

FIG. 9 shows that, consistent with the previous results, the diabetic animals have gained much more body weight than the control ones while the treated group gained weight moderately.

As shown by FIG. 10A, the initial blood glucose level in all the groups was approximately 70 mg/dl. The blood glucose level in the control animals (Group I) remained stable through all the experiment. The animals on high energy diet (Group II) demonstrated a continuous increase of blood glucose level, reaching 300 mg/dl on day 56, decreasing to 250 mg/dl toward the end of the experiment. The blood glucose value of animals from the Group III (Zn-DFO-treated) reached 200 mg/dl on day 28 and then decreased to 110 mg/dl toward the end of experiment.

FIG. 10B presents the results of the glucose tolerance test (in the form of an integration of total glucose levels after glucose administration). The Zn-DFO-treated animals demonstrated an insignificantly higher value than Group I, while the diabetic animals' value (Group II) was markedly higher.

FIG. 11 depicts the measured 2,3-DHBA blood concentration. Whereas the development of diabetes induced a 3.2-fold increase in this parameter in comparison with control values, Zn-DFO-treated animals maintained almost baseline values.

Figure 12:
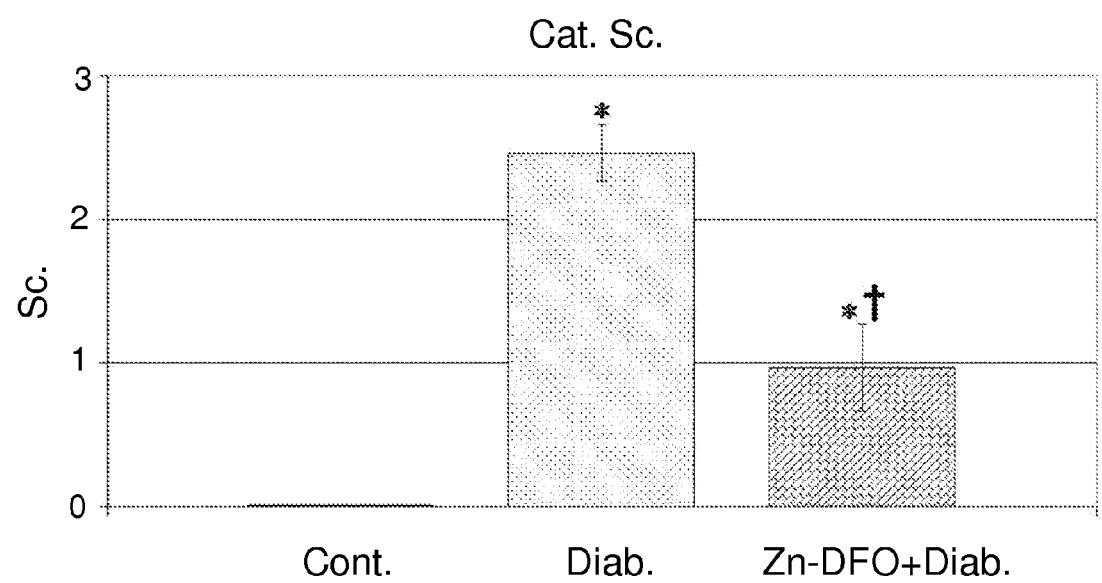

The formation of diabetes-induced cataract was next examined. As shown by FIG. 12, control animals (Group I) did not develop cataract. In Group II, five of total of seven animals presented severe (grade 3) cataract. Two other animals had grade 1-2 cataract. Among the animals from the treated group (Group III), four did not develop cataract. Severe (grade 3) cataract was developed in one animal that had high blood glucose level as well. Two other animals showed grade 1-2 cataract in both eyes.

Measuring total lens protein using Bradford assay, the inventors found that diabetes led to more than 4.5-fold decrease in lens protein concentration compared to the control values as shown by FIG. 13. Zn-DFO treatment partly prevented this decrease. The same trend was demonstrated in the parameters of methionine-centered redox cycle (MCRC) and actin, as shown by FIGS. 14 and 15. Diabetes caused a significant decrease in the concentration of Trx (FIG. 14A), TrxR (FIG. 14B) and actin (FIG. 15A), and Msr (FIG. 15B) activity in the lens, in comparison to the control animals. Zn-DFO treatment led to its partial, but statistically significant restoration. Since cataract formation is associated with a sizeable increase in proteins oxidation, followed by decrease in its activity and, finally, degradation, these findings demonstrate an increase in protection against ROS.

On the other hand, FIG. 16 shows that a sizeable 10-fold increase in the ferritin content was observed in the diabetic animals compared to control animals. This is in accord with line of evidence, showing an association between ferritin accumulation and cataract formation in dogs and humans. Following the previously demonstrated trend, Zn-DFO treatment induced a 3.8-fold decrease in ferritin level.

Example 8

Ga-DFO/Zn-DFO Combination Cannot Restore Normal Blood Glucose Levels in Streptozotocin-induced Diabetes Type I, but Improves General Health State Thus far, the inventors investigated the beneficial effects imparted by the metal complexes and combined complexes of the invention in diabetes type II model, where insulin producing pancreatic cells are intact and insulin production is existent. Next, the inventors explored the effects the complexes have on diabetes type I, where the insulin-secreting pancreatic cells are eliminated, and therefore insulin in unavailable. The experiment was performed using Sprague-Dawley rats as a model, as described in the Experimental Procedures. The rats were turned to diabetics by streptozotocin (STZ) injection and treated with a Ga-DFO/Zn-DFO in a 1:3 ratio mixture. The influence of the complex on the STZ-induced model of diabetes (which resembles Type I diabetes) was examined.

Sprague-Dawley (SD) male rats were separated into two groups. Diabetes was induced in the first group (SD group) by streptozotocin. Blood glucose level was measured twice a week throughout the experiment. Three days after the injection the animals from the second group have demonstrated high level of blood glucose, showing the onset of diabetes. At the second week the treatment with Ga-DFO/Zn-DFO was started. Each group was separated into two subgroups, and animals from one diabetic subgroup and one control subgroup received injections of Ga-DFO/Zn-DFO mixture 0.25 mg/kg i.p twice a week, while their blood glucose and body weight were monitored. The untreated subgroups received saline according to the same pattern.

Comparing appearance of the treated and untreated non-diabetic animals, no differences were found. On the other hand, in a contrast with the untreated diabetic rats, the complex-treated animals looked physically better throughout the duration of the experiment, displaying no pink spots on the head, neck and shoulders. The treated rats showed less frequent urination, decreased sweating, had less expressed ketone odor, characteristic for the diabetic animals, and displayed markedly decreased mortality. Table 6 demonstrates that no bodyweight loss occurred in treated animals, and, moreover, the animals from both groups have even gained weight, an uncommon event in a case of severe diabetics.

However, as Table 7 illustrates, complex treatment had no influence on blood glucose level, since STZ destroys pancreatic cells, physically eliminating its ability to secrete insulin and decreasing, therefore, blood glucose level. Still, the inventors overall impression was that in spite of an irreversibly cytotoxic effect of STZ on the pancreas of the animals, Ga-DFO/Zn-DFO markedly improved their condition, albeit without restoring their normal blood glucose level.

TABLE 6

Body weight in treated and non-treated SD rats

| Subgroup | Week 1 | 2 | 3 | 4 |
|---|---|---|---|---|
| Control non-diabetic | 245 ± 10 | 266 ± 8 | 272 ± 7 | 279 ± 11 |
| Diabetic | 253 ± 10 | 245 ± 8 | 250 ± 9 | 240 ± 12 |
| Control non-diabetic - Ga-DFO/Zn-DFO | 228 ± 6 | 252 ± 5 | 262 ± 3 | 273 ± 2 |
| Diabetes - Ga-DFO/Zn-DFO | 230 ± 3 | 281 ± 5* | 270 ± 9* | 256 ± 10* |

Mean values (g) ± SE are shown;
*denotes p < 0.05 vs. the respective subgroup at the same time period;

TABLE 7

Blood glucose levels in treated and non-treated SD rats

| Subgroup | Week 1 | 2 | 3 | 4 |
|---|---|---|---|---|
| Control non-diabetic | 79 ± 9 | 77 ± 9 | 80 ± 8 | 78 ± 8 |
| Diabetic | 81 ± 10 | 358 ± 44* | 376 ± 45* | 438 ± 56* |
| Control non-diabetic - Ga-DFO/Zn-DFO | 80 ± 7 | 82 ± 9 | 81 ± 6 | 77 ± 9 |
| Diabetic - Ga-DFO/Zn-DFO | 80 ± 4 | 371 ± 24* | 384 ± 22* | 442 ± 31* |

Mean values (g) ± SE are shown;
*denotes p < 0.05 vs. the respective subgroup at the same time period;

None of treated diabetic animals died during the experiment, in contrast with previously published data, where the mortality of 17-48% was observed [Bar-On H et al. Diabetes 1976; 25 (6): 509-515; Wei M et al. Heart Lung Circ. 2003; 12(1):44-50]. Furthermore, no cataract developed and the smell of acetone was markedly weaker, indicating, presumably, less ketone formation.

Example 9

Preparation of Zinc-Desferrioxamine (Zn-DFO) and Vaseline-based Zn-DFO/Ga-DFO Ointment for Dermal Application Zinc-DFO was prepared from highest purity available zinc chloride solid powder which was purchased from Aldrich Chemical, St. Louis, Mo. Desferal® (DFO) USP grade was purchased from Novartis AG, Switzerland, and dissolved in DDW. The complex was prepared as described in Experimental procedures. A Vaseline-based ointment containing 0.5% (w/v) of a combination of gallium DFO (0.1%) and zinc DFO (0.4%) was prepared by mixing the aqueous concentrated solutions of the complexes with Tween 80, and subsequently mixing this mixture with pre-heated Vaseline (to 60° C.).

Example 10

The Combination of Gallium DFO and Zinc DFO is not Dermatoxic

The inventors were also interested in exploring the possible uses of metal-DFO complexes in the treatment of psoriasis. Since psoriasis is an adverse inflammation of the skin which involves local excess of free radicals and other reactive oxygen-derived and nitrogen-derived species, the removal of labile iron from affected sites in the skin by the complexes might inhibit local free radicals production and alleviate the disease symptoms. To assess these effects, a skin-permeable ointment containing gallium DFO and zinc DFO was produced.

The Vaseline-based ointment containing a combination of gallium DFO and zinc DFO was prepared as described in Example 9. A thin layer of the ointment was applied to three areas of 50 cm$^2$, each, of three healthy male volunteers and one female volunteer, for three days, twice daily. The treated areas were exposed to air without any special shield. The color of the skin was persistently maintained normal: it did not wash off and could not be rubbed off. The natural color of the skin remained unchanged during the experiment and during the subsequent seven days, while the skin was observed. There was no scarring, hair loss or other change in appearance of the skin. The subjects treated did not experience itching or pain of the skin or of any part of his arm either during the 3 day test or at any time after the test. Thus, the inventors surmised that the Zn-DFO and Ga-DFO combination did not irritate or induce other toxic effects in the skin.

Example 11

Clearance of Symptoms of Persistent Psoriasis

Having verified that Zn-DFO and Ga-DFO were not dermatoxic, the inventors investigated the beneficial properties of these complexes for the treatment of psoriasis.

In a first test, a 45 year old male subject (DC) who suffered from severe psoriasis of the skin around the elbows and knees for more than 5 years was treated. His informed consent was obtained. His left arm and knee were treated with ointment containing 0.5% Zn-DFO complex, while the other elbow and knee were treated with a common corticosteroid containing cream (Dovonex 0.005%, Leo® Laboratories Inc., Dublin, Ireland). The Zn-DFO was applied once daily, on days 1, 3, 6 and 9. The corticosteroid ointment was applied once daily. On day 11, both sides were examined. The skin of the left elbow and knee (Zn-DFO complex-treated) looked normal and with light healthy pink color. The skin of the right side was devoid of lesions but looked un-smooth and slightly inflamed However, about two months after the treatment the subject developed again the symptoms of psoriasis, due to sporadic use of the ointment. The patient was offered a regular treatment, for achieving complete recovery.

In a second test, a 66 year old male subject (DG) who suffered from severe psoriasis of the skin around the elbows and the back of the hands palms for more than 25 years was treated. His informed consent was obtained. Both elbows and back of the hands palms were treated with ointment containing 0.4% Zn-DFO complex together with 0.1% Ga-DFO. The patient was instructed to wash the affected areas with warm soap water and then apply a thin layer of the ointment as follows: twice on day 1, twice on day 2, once on days 4, 6 and 8. On day 4 the patient stopped the treatment since, according to him, his hands looked normal, and the color of his skin changed to pink. During the week without treatment the affected areas became un-smooth. On day 9, the patient continued with 3 additional daily treatments, when all symptoms disappeared.

In a third test, a 63 year old female subject (LV) who suffered from two 0.7×0.3 cm in diameter lesions of seborrheal dermatitis on the face. She was treated twice weekly for 2 weeks, by applying a thin layer of ointment containing Zn-DFO/Ga-DFO (0.5%; 4:1 ratio).

Her informed consent was obtained. One of the lesions completed healed, and did not re-occur for the next 10 weeks, while the second lesion lost its redish color, but persisted.

Example 12

Effects of Zn-DFO, Ga-DFO and their Combination on Wound Healing, Heat Burns and Sun Burns The inventor's next wish to ascertain whether Zn-DFO, Ga-DFO and their combination impart a positive effect on wound, sun burn and heat burn healing processes. Upon injury, wounds and burns undergo a process of initial local inflammation and later repair. The inflammation phase involves increased production of ROS, which may slow or, in some cases, prevent resolution of the injured tissue.

Informed consent for experimental treatment is obtained from patients suffering from hand superficial (skin-deep) wounds, sun burns and heat burns, including all burn degrees. In the case of superficial wounds and first degree burns, the patients are divided into three groups. Group 1 is left untreated; Group 2 is treated with the Vaseline vehicle (without the active complexes); and Group 3 is treated with the Vaseline-based ointment (0.5%, 4:1 ratio of Zn-DFO and Ga-DFO. A thin layer of the ointment applied once daily. The wound or burn diameter is measured using a caliper. Skin biopsies are collected after 2 and 5 days into treatment. Biopsies are sectioned and stained with Mason's trichrome staining for fibrous connective tissue or haematoxylin-eosine. The presence of inflammatory infiltrating cells and deposition of protein fibers in scar tissue is assessed.

Treatment of heat-induced skin burn, with blisters with the ointment containing Zn-DFO/Ga-DFO (4:1; 0.5%) is performed by application of thin layer, twice daily. The rate of healing and disappearance of blisters and scarring is monitored.

Treatment of sun-induced skin burn, with the ointment containing Zn-DFO/Ga-DFO (4:1; 0.5%) is performed by application of thin layer, twice daily. The rate of healing and recovery of the natural color of the skin is monitored.

The invention claimed is:

1. A method of treating, ameliorating, inhibiting or reducing the risk of occurrence or recurrence of a chronic or acute inflammatory-related skin pathologic condition selected from the group consisting of psoriasis, dermatitis, acne, vitiligo and wounds, comprising the step of administering to a subject in need thereof a therapeutically effective amount of at least one desferrioxamine-metal complex (DFO-metal complex), or any combination thereof or any pharmaceutical composition comprising the same.

2. The method according to claim 1, wherein said method comprises the step of administering to a subject in need thereof a therapeutically effective amount of at least one of zinc-desferrioxamine complex (Zn-DFO), gallium-desferrioxamine complex (Ga-DFO), any combination thereof or any composition comprising the same.

3. The method according to claim 1, wherein said chronic or acute inflammatory related skin pathologic condition is psoriasis.

4. A method of treating, ameliorating, inhibiting or reducing the risk of occurrence or recurrence of a chronic or acute inflammatory-related skin pathologic condition, wherein the condition is wound and the method results in healing of said wound.

* * * * *